United States Patent
Bao et al.

(10) Patent No.: US 9,445,916 B2
(45) Date of Patent: Sep. 20, 2016

(54) JOINT ARTHROPLASTY DEVICES HAVING ARTICULATING MEMBERS

(75) Inventors: Qi-Bin Bao, Marquette, MI (US); Tim Brown, Negaunee, MI (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 1468 days.

(21) Appl. No.: 11/856,565

(22) Filed: Sep. 17, 2007

(65) Prior Publication Data

US 2008/0109081 A1  May 8, 2008

Related U.S. Application Data

(63) Continuation-in-part of application No. 10/692,468, filed on Oct. 22, 2003, now Pat. No. 8,388,684, and a continuation-in-part of application No. 10/971,734, filed on Oct. 22, 2004, now Pat. No. 8,241,360.

(60) Provisional application No. 60/825,865, filed on Sep. 15, 2006, provisional application No. 60/916,734, filed on May 8, 2007.

(51) Int. Cl.
*A61F 2/44* (2006.01)
*A61F 2/32* (2006.01)
(Continued)

(52) U.S. Cl.
CPC ............. *A61F 2/4425* (2013.01); *A61F 2/32* (2013.01); *A61F 2/38* (2013.01); *A61F 2/4202* (2013.01); *A61F 2/4405* (2013.01); *A61L 27/18* (2013.01); *A61L 27/34* (2013.01); *A61B 17/86* (2013.01); *A61F 2/30767* (2013.01); *A61F 2/34* (2013.01); *A61F 2/36* (2013.01); *A61F 2/389* (2013.01); *A61F 2/3859* (2013.01); *A61F 2/468* (2013.01); *A61F 2002/3008* (2013.01); *A61F 2002/3085* (2013.01); *A61F 2002/30383* (2013.01); *A61F 2002/30387* (2013.01);
(Continued)

(58) Field of Classification Search
CPC .................... A61F 2002/443; A61F 2002/444
USPC ............................................ 623/17.11–17.16
See application file for complete search history.

(56) References Cited

U.S. PATENT DOCUMENTS 3,867,728 A  2/1975  Stubstad et al.
3,875,595 A  4/1975  Froning
(Continued)

FOREIGN PATENT DOCUMENTS

CA      2395609     2/2001
CA      2482403     9/2003
(Continued)

OTHER PUBLICATIONS

Depuy Spine, Inc., Charite Artificial Disc Centreline TDR Instrumentation, Surgical Technique, Dec. 2004, 21 pp.
(Continued)

*Primary Examiner* — Matthew Lawson
(74) *Attorney, Agent, or Firm* — Fitch, Even, Tabin & Flannery LLP

(57) ABSTRACT

Articulating devices for replacing damaged or degenerated weight bearing joints are provided. The devices may have two or more surfaces that articulate against one another that are coated or fully formed of PEEK or similar materials to provide improved wear capabilities while maintaining sufficient strength to operate in a weight bearing capacity.

25 Claims, 27 Drawing Sheets

(51) Int. Cl.

| | | |
|---|---|---|
| *A61F 2/38* | (2006.01) | |
| *A61F 2/42* | (2006.01) | |
| *A61L 27/18* | (2006.01) | |
| *A61L 27/34* | (2006.01) | |
| *A61B 17/86* | (2006.01) | |
| *A61F 2/30* | (2006.01) | |
| *A61F 2/34* | (2006.01) | |
| *A61F 2/36* | (2006.01) | |
| *A61F 2/46* | (2006.01) | |

(52) U.S. Cl.
CPC .......... *A61F 2002/30487* (2013.01); *A61F 2002/30604* (2013.01); *A61F 2002/30685* (2013.01); *A61F 2002/30772* (2013.01); *A61F 2002/30787* (2013.01); *A61F 2002/30841* (2013.01); *A61F 2002/30843* (2013.01); *A61F 2002/30892* (2013.01); *A61F 2002/30894* (2013.01); *A61F 2002/30904* (2013.01); *A61F 2002/30934* (2013.01); *A61F 2002/3401* (2013.01); *A61F 2002/3411* (2013.01); *A61F 2002/3429* (2013.01); *A61F 2002/3493* (2013.01); *A61F 2002/365* (2013.01); *A61F 2002/3611* (2013.01); *A61F 2002/4205* (2013.01); *A61F 2002/4207* (2013.01); *A61F 2002/444* (2013.01); *A61F 2002/4631* (2013.01); *A61F 2220/0025* (2013.01); *A61F 2250/0098* (2013.01); *A61F 2310/00005* (2013.01); *A61F 2310/00011* (2013.01); *A61F 2310/00389* (2013.01); *A61F 2310/00407* (2013.01); *A61F 2310/00796* (2013.01)

(56) References Cited

U.S. PATENT DOCUMENTS

| | | |
|---|---|---|
| 3,975,778 A | 8/1976 | Newton, III |
| 4,021,382 A | 5/1977 | Stoy et al. |
| 4,081,402 A | 3/1978 | Levy et al. |
| 4,147,764 A | 4/1979 | Levy et al. |
| 4,309,777 A | 1/1982 | Patil |
| 4,349,921 A | 9/1982 | Kuntz |
| 4,454,612 A | 6/1984 | McDaniel et al. |
| 4,650,490 A | 3/1987 | Figgie, III |
| 4,714,469 A | 12/1987 | Kenna |
| 4,728,561 A | 3/1988 | Crocker |
| 4,759,766 A | 7/1988 | Buettner-Janz et al. |
| 4,759,769 A | 7/1988 | Hedman et al. |
| 4,863,476 A | 9/1989 | Shepperd |
| 4,863,477 A | 9/1989 | Monson |
| 4,917,704 A | 4/1990 | Frey et al. |
| 4,932,969 A | 6/1990 | Frey et al. |
| 4,936,848 A | 6/1990 | Bagby |
| 4,946,378 A | 8/1990 | Hirayama et al. |
| 4,997,432 A | 3/1991 | Keller |
| 5,002,576 A | 3/1991 | Fuhrmann et al. |
| 5,035,716 A | 7/1991 | Downey |
| 5,047,055 A | 9/1991 | Bao et al. |
| 5,071,437 A | 12/1991 | Steffee |
| 5,108,438 A | 4/1992 | Stone |
| 5,127,920 A | 7/1992 | MacArthur |
| 5,133,759 A | 7/1992 | Turner |
| 5,133,772 A | 7/1992 | Hack et al. |
| 5,147,404 A | 9/1992 | Downey |
| 5,171,281 A | 12/1992 | Parsons et al. |
| 5,176,710 A | 1/1993 | Hahn et al. |
| 5,192,326 A | 3/1993 | Bao et al. |
| 5,258,031 A | 11/1993 | Salib et al. |
| 5,258,043 A | 11/1993 | Stone |
| 5,273,742 A | 12/1993 | Gould et al. |
| 5,306,308 A | 4/1994 | Gross et al. |
| 5,306,309 A | 4/1994 | Wagner et al. |
| 5,314,477 A | 5/1994 | Marnay |
| 5,320,625 A | 6/1994 | Bertin |
| 5,320,644 A | 6/1994 | Baumgartner |
| 5,401,269 A | 3/1995 | Buettner-Janz et al. |
| 5,425,773 A | 6/1995 | Boyd et al. |
| 5,443,512 A | 8/1995 | Parr et al. |
| 5,458,642 A | 10/1995 | Beer et al. |
| 5,458,643 A | 10/1995 | Oka et al. |
| 5,462,362 A | 10/1995 | Yuhta et al. |
| 5,480,449 A | 1/1996 | Hamilton et al. |
| 5,507,816 A | 4/1996 | Bullivant |
| 5,514,180 A | 5/1996 | Heggeness et al. |
| 5,522,899 A | 6/1996 | Michelson |
| 5,534,028 A | 7/1996 | Bao et al. |
| 5,549,679 A | 8/1996 | Kuslich |
| 5,556,431 A | 9/1996 | Buettner-Janz |
| 5,556,433 A | 9/1996 | Gabriel et al. |
| 5,562,736 A | 10/1996 | Ray et al. |
| 5,562,738 A | 10/1996 | Boyd et al. |
| 5,571,189 A | 11/1996 | Kuslich |
| 5,595,563 A | 1/1997 | Moisdon |
| 5,609,643 A | 3/1997 | Colleran et al. |
| 5,645,596 A | 7/1997 | Kim et al. |
| 5,645,597 A | 7/1997 | Krapiva |
| 5,658,336 A | 8/1997 | Pisharodi |
| 5,665,122 A | 9/1997 | Kambin |
| 5,674,295 A | 10/1997 | Ray et al. |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,693,100 A | 12/1997 | Pisharodi |
| 5,702,450 A | 12/1997 | Bisserie |
| 5,716,416 A | 2/1998 | Lin |
| 5,728,762 A | 3/1998 | Reich et al. |
| 5,755,797 A | 5/1998 | Baumgartner |
| 5,755,798 A | 5/1998 | Papavero et al. |
| 5,782,832 A | 7/1998 | Larsen et al. |
| 5,824,093 A | 10/1998 | Ray et al. |
| 5,824,094 A | 10/1998 | Serhan et al. |
| 5,860,980 A | 1/1999 | Axelson, Jr. et al. |
| 5,865,845 A | 2/1999 | Thalgott |
| 5,865,846 A | 2/1999 | Bryan et al. |
| 5,888,223 A | 3/1999 | Bray, Jr. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima et al. |
| 5,919,235 A | 7/1999 | Husson et al. |
| 5,964,807 A | 10/1999 | Gan et al. |
| 5,969,020 A | 10/1999 | Shalaby et al. |
| 5,976,186 A | 11/1999 | Bao et al. |
| 5,980,572 A | 11/1999 | Kim et al. |
| 6,001,130 A | 12/1999 | Bryan et al. |
| 6,019,793 A | 2/2000 | Perren et al. |
| 6,022,376 A | 2/2000 | Assell et al. |
| 6,039,763 A | 3/2000 | Shelokov |
| RE36,758 E | 6/2000 | Fitz |
| 6,074,390 A | 6/2000 | Zucherman et al. |
| 6,093,205 A | 7/2000 | McLeod et al. |
| 6,093,207 A | 7/2000 | Pisharodi |
| 6,110,210 A | 8/2000 | Norton et al. |
| 6,127,597 A | 10/2000 | Beyar et al. |
| 6,132,465 A | 10/2000 | Ray et al. |
| 6,136,031 A | 10/2000 | Middleton |
| 6,139,579 A | 10/2000 | Steffee et al. |
| 6,143,031 A | 11/2000 | Knothe et al. |
| 6,146,422 A | 11/2000 | Lawson |
| 6,156,067 A | 12/2000 | Bryan et al. |
| 6,162,252 A | 12/2000 | Kuras et al. |
| 6,179,874 B1 | 1/2001 | Cauthen |
| 6,183,518 B1 | 2/2001 | Ross et al. |
| 6,187,048 B1 | 2/2001 | Milner et al. |
| 6,190,387 B1 | 2/2001 | Zucherman et al. |
| 6,206,924 B1 | 3/2001 | Timm |
| 6,224,630 B1 | 5/2001 | Bao et al. |
| 6,240,926 B1 | 6/2001 | Chin Gan et al. |
| 6,251,140 B1 | 6/2001 | Marino et al. |
| 6,264,695 B1 | 7/2001 | Stoy |
| 6,280,475 B1 | 8/2001 | Bao et al. |

(56) References Cited

U.S. PATENT DOCUMENTS

| | | |
|---|---|---|
| 6,283,968 B1 | 9/2001 | Mehdizadeh |
| 6,283,998 B1 | 9/2001 | Eaton |
| 6,315,795 B1 | 11/2001 | Scarborough et al. |
| 6,315,797 B1 | 11/2001 | Middleton |
| 6,348,071 B1 | 2/2002 | Steffee et al. |
| 6,352,557 B1 | 3/2002 | Ferree |
| 6,368,350 B1 * | 4/2002 | Erickson et al. .......... 623/17.14 |
| 6,371,990 B1 | 4/2002 | Ferree |
| 6,375,682 B1 | 4/2002 | Fleischmann et al. |
| 6,395,032 B1 | 5/2002 | Gauchet |
| 6,402,784 B1 | 6/2002 | Wardlaw |
| 6,402,785 B1 | 6/2002 | Zdeblick et al. |
| 6,419,704 B1 | 7/2002 | Ferree |
| 6,428,544 B1 | 8/2002 | Ralph et al. |
| 6,428,575 B2 | 8/2002 | Koo et al. |
| 6,428,579 B1 | 8/2002 | Valentini |
| 6,432,106 B1 | 8/2002 | Fraser |
| 6,432,107 B1 | 8/2002 | Ferree |
| 6,432,140 B1 | 8/2002 | Lin |
| 6,436,098 B1 | 8/2002 | Michelson |
| 6,436,101 B1 | 8/2002 | Hamada |
| 6,436,102 B1 | 8/2002 | Ralph et al. |
| 6,436,140 B1 | 8/2002 | Liu et al. |
| 6,436,141 B2 | 8/2002 | Castro et al. |
| 6,436,142 B1 | 8/2002 | Paes et al. |
| 6,436,146 B1 | 8/2002 | Hassler et al. |
| 6,440,168 B1 | 8/2002 | Cauthen |
| 6,440,170 B1 | 8/2002 | Jackson |
| 6,478,822 B1 | 11/2002 | Leroux et al. |
| 6,488,716 B1 | 12/2002 | Huang |
| 6,508,839 B1 | 1/2003 | Lambrecht et al. |
| 6,517,580 B1 | 2/2003 | Ramadan et al. |
| 6,527,804 B1 | 3/2003 | Gauchet et al. |
| 6,540,785 B1 | 4/2003 | Gill et al. |
| 6,547,823 B2 | 4/2003 | Scarborough et al. |
| 6,562,047 B2 | 5/2003 | Ralph et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,592,624 B1 | 7/2003 | Fraser et al. |
| 6,602,291 B1 | 8/2003 | Ray et al. |
| 6,610,091 B1 | 8/2003 | Reiley |
| 6,679,915 B1 | 1/2004 | Cauthen |
| 6,682,562 B2 | 1/2004 | Viart et al. |
| 6,743,257 B2 | 6/2004 | Castro |
| 6,770,095 B2 | 8/2004 | Grinberg et al. |
| 6,783,550 B2 | 8/2004 | MacArthur |
| 6,793,678 B2 | 9/2004 | Hawkins |
| 6,899,716 B2 | 5/2005 | Cragg |
| 6,936,071 B1 | 8/2005 | Marnay et al. |
| 7,001,433 B2 | 2/2006 | Songer et al. |
| 7,156,876 B2 | 1/2007 | Moumene et al. |
| 8,303,660 B1 * | 11/2012 | Abdou ................. 623/17.14 |
| 2001/0010021 A1 | 7/2001 | Boyd et al. |
| 2001/0012938 A1 | 8/2001 | Zucherman et al. |
| 2001/0016772 A1 | 8/2001 | Lee et al. |
| 2001/0016773 A1 | 8/2001 | Serhan et al. |
| 2001/0016776 A1 | 8/2001 | Zucherman et al. |
| 2001/0020476 A1 | 9/2001 | Gan et al. |
| 2001/0027343 A1 | 10/2001 | Keller |
| 2001/0032019 A1 | 10/2001 | Van Dyke et al. |
| 2001/0032020 A1 | 10/2001 | Besselink |
| 2001/0047208 A1 | 11/2001 | Michelson |
| 2001/0051829 A1 | 12/2001 | Middleton |
| 2002/0013600 A1 | 1/2002 | Scribner et al. |
| 2002/0022883 A1 | 2/2002 | Burg |
| 2002/0022888 A1 | 2/2002 | Serhan et al. |
| 2002/0026244 A1 | 2/2002 | Trieu |
| 2002/0029082 A1 | 3/2002 | Muhanna |
| 2002/0029083 A1 | 3/2002 | Zucherman et al. |
| 2002/0035400 A1 | 3/2002 | Bryan et al. |
| 2002/0045942 A1 | 4/2002 | Ham |
| 2002/0045944 A1 | 4/2002 | Muhanna et al. |
| 2002/0049498 A1 | 4/2002 | Yuksel et al. |
| 2002/0082608 A1 | 6/2002 | Reiley et al. |
| 2002/0082701 A1 | 6/2002 | Zdeblick et al. |
| 2002/0087480 A1 | 7/2002 | Sauriol et al. |
| 2002/0099444 A1 | 7/2002 | Boyd et al. |
| 2002/0106393 A1 | 8/2002 | Bianchi et al. |
| 2002/0107571 A1 | 8/2002 | Foley |
| 2002/0107572 A1 | 8/2002 | Foley et al. |
| 2002/0107573 A1 | 8/2002 | Steinberg |
| 2002/0120269 A1 | 8/2002 | Lange |
| 2002/0120270 A1 | 8/2002 | Trieu et al. |
| 2002/0120334 A1 | 8/2002 | Crozet |
| 2002/0120336 A1 | 8/2002 | Santilli |
| 2002/0156528 A1 | 10/2002 | Gau |
| 2002/0165612 A1 | 11/2002 | Gerber et al. |
| 2003/0009226 A1 | 1/2003 | Graf |
| 2003/0023311 A1 | 1/2003 | Trieu |
| 2003/0028197 A1 | 2/2003 | Hanson et al. |
| 2003/0028251 A1 | 2/2003 | Mathews |
| 2003/0040799 A1 | 2/2003 | Boyd et al. |
| 2003/0045939 A1 | 3/2003 | Casutt |
| 2003/0055427 A1 | 3/2003 | Graf |
| 2003/0074076 A1 | 4/2003 | Ferree et al. |
| 2003/0100950 A1 * | 5/2003 | Moret ................. 623/17.16 |
| 2003/0100951 A1 | 5/2003 | Serhan et al. |
| 2003/0135276 A1 | 7/2003 | Eckman |
| 2003/0135277 A1 | 7/2003 | Bryan et al. |
| 2003/0135278 A1 | 7/2003 | Eckman |
| 2003/0176921 A1 | 9/2003 | Lawson |
| 2003/0204260 A1 | 10/2003 | Ferree |
| 2003/0204261 A1 | 10/2003 | Eisermann et al. |
| 2003/0220691 A1 | 11/2003 | Songer et al. |
| 2004/0024462 A1 | 2/2004 | Ferree et al. |
| 2004/0030391 A1 | 2/2004 | Ferree |
| 2004/0044410 A1 | 3/2004 | Ferree et al. |
| 2004/0082999 A1 | 4/2004 | Mathys, Jr. et al. |
| 2004/0093082 A1 | 5/2004 | Ferree |
| 2004/0102846 A1 | 5/2004 | Keller et al. |
| 2004/0117019 A1 | 6/2004 | Trieu et al. |
| 2004/0117022 A1 | 6/2004 | Marnay et al. |
| 2004/0133278 A1 * | 7/2004 | Marino et al. ............. 623/17.14 |
| 2004/0143332 A1 * | 7/2004 | Krueger et al. ........... 623/17.14 |
| 2004/0153157 A1 | 8/2004 | Keller |
| 2004/0204760 A1 | 10/2004 | Fitz et al. |
| 2004/0220670 A1 * | 11/2004 | Eisermann et al. ....... 623/17.14 |
| 2005/0021042 A1 | 1/2005 | Marnay et al. |
| 2005/0021143 A1 | 1/2005 | Keller |
| 2005/0021149 A1 | 1/2005 | Borruto et al. |
| 2005/0033437 A1 | 2/2005 | Bao et al. |
| 2005/0071011 A1 | 3/2005 | Ralph et al. |
| 2005/0085911 A1 | 4/2005 | Link |
| 2005/0085917 A1 | 4/2005 | Marnay et al. |
| 2005/0165485 A1 | 7/2005 | Trieu |
| 2005/0192671 A1 | 9/2005 | Bao et al. |
| 2005/0209698 A1 * | 9/2005 | Gordon et al. ............. 623/17.15 |
| 2005/0256581 A1 | 11/2005 | Songer et al. |
| 2006/0004453 A1 | 1/2006 | Bartish, Jr. et al. |
| 2006/0020342 A1 | 1/2006 | Ferree et al. |
| 2006/0041314 A1 | 2/2006 | Millard et al. |
| 2006/0212122 A1 * | 9/2006 | Perera .................. A61F 2/4425 623/17.14 |
| 2006/0235527 A1 | 10/2006 | Buettner-Janz et al. |
| 2006/0235528 A1 | 10/2006 | Buettner-Janz |
| 2006/0235531 A1 | 10/2006 | Buettner-Janz |
| 2007/0027547 A1 | 2/2007 | Rydell et al. |
| 2007/0100454 A1 | 5/2007 | Burgess et al. |
| 2008/0288081 A1 | 11/2008 | Scrafton et al. |
| 2009/0043390 A1 | 2/2009 | Meisel |
| 2009/0164023 A1 | 6/2009 | Devine |
| 2009/0185904 A1 | 7/2009 | Landberg |

FOREIGN PATENT DOCUMENTS

| | | |
|---|---|---|
| CA | 2548780 | 7/2005 |
| CN | 1697633 | 11/2005 |
| DE | 9000094 U1 | 1/1991 |
| DE | 29911422 U1 | 8/1999 |
| DE | 10130825 | 3/2002 |
| EP | 0179695 | 4/1986 |
| EP | 0346129 A1 | 12/1989 |
| EP | 0773008 A1 | 5/1997 |

(56) References Cited

FOREIGN PATENT DOCUMENTS

| | | |
|---|---|---|
| EP | 0919209 A1 | 6/1999 |
| EP | 1104665 A1 | 6/2001 |
| FR | 2372622 | 6/1978 |
| FR | 2723841 | 3/1996 |
| FR | 2787014 | 6/2000 |
| FR | 2797179 | 2/2001 |
| FR | 2799116 | 4/2001 |
| FR | 2805985 | 9/2001 |
| FR | 2824261 | 11/2002 |
| JP | 63300758 A2 | 12/1988 |
| JP | 1308557 A2 | 12/1989 |
| JP | 2111358 | 4/1990 |
| JP | 2215461 A2 | 8/1990 |
| JP | 2224659 A2 | 9/1990 |
| JP | 2224660 A2 | 9/1990 |
| JP | 03275055 A | 5/1991 |
| JP | 03275056 A | 5/1991 |
| JP | 04303444 A | 10/1992 |
| JP | 05277141 A | 10/1993 |
| JP | 06285099 | 10/1994 |
| JP | 08098850 A | 4/1996 |
| JP | 08098851 A | 4/1996 |
| JP | 11137585 A | 5/1999 |
| JP | 11009618 A | 10/1999 |
| JP | 2008-284348 A | 11/2008 |
| WO | 9011740 | 10/1990 |
| WO | 9105521 | 5/1991 |
| WO | 9116867 | 11/1991 |
| WO | 9316664 | 9/1993 |
| WO | 9500082 | 5/1995 |
| WO | 9601598 | 1/1996 |
| WO | 9611642 | 4/1996 |
| WO | 9627339 | 9/1996 |
| WO | 9805274 | 2/1998 |
| WO | 9855053 | 12/1998 |
| WO | 9911203 | 3/1999 |
| WO | 9922675 | 5/1999 |
| WO | 9930651 | 6/1999 |
| WO | 0013619 | 3/2000 |
| WO | 0132100 | 5/2001 |
| WO | 02115638 A1 | 8/2001 |
| WO | 0168003 | 9/2001 |
| WO | 02087480 | 11/2002 |
| WO | 2005009298 | 2/2005 |
| WO | 2006016384 | 2/2006 |
| WO | 2006061114 | 6/2006 |

OTHER PUBLICATIONS

Depuy Spine, Inc., Charite Artificial Disc Product Catalog, Dec. 2004, 17 pp.
Feder, B., When F.D.A. Says Yes, But Insurers Say No, The New York Times, Jul. 6, 2005, 2 pp.
Bao, Q. et al, Artificial Disc Technology, Nerosurg. Focus, vol. 9, Oct. 2000, 7 pp.
Zdeblick, T. et al, Cervical Interbody Cages, An Animal Mode With and Without Bone Morphogenetic Protein, Spine, 1998, vol. 23, No. 7, 11 pp.
The State Intellectual Property Office of China, First Notification of Office Action, Dec. 15, 2010, 9 pp.

* cited by examiner

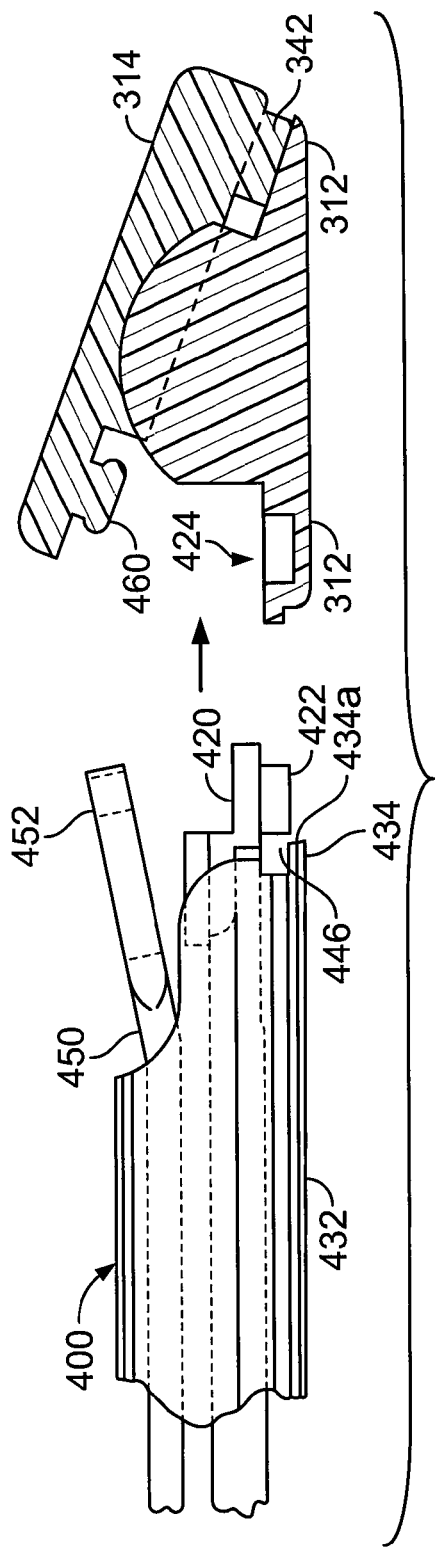

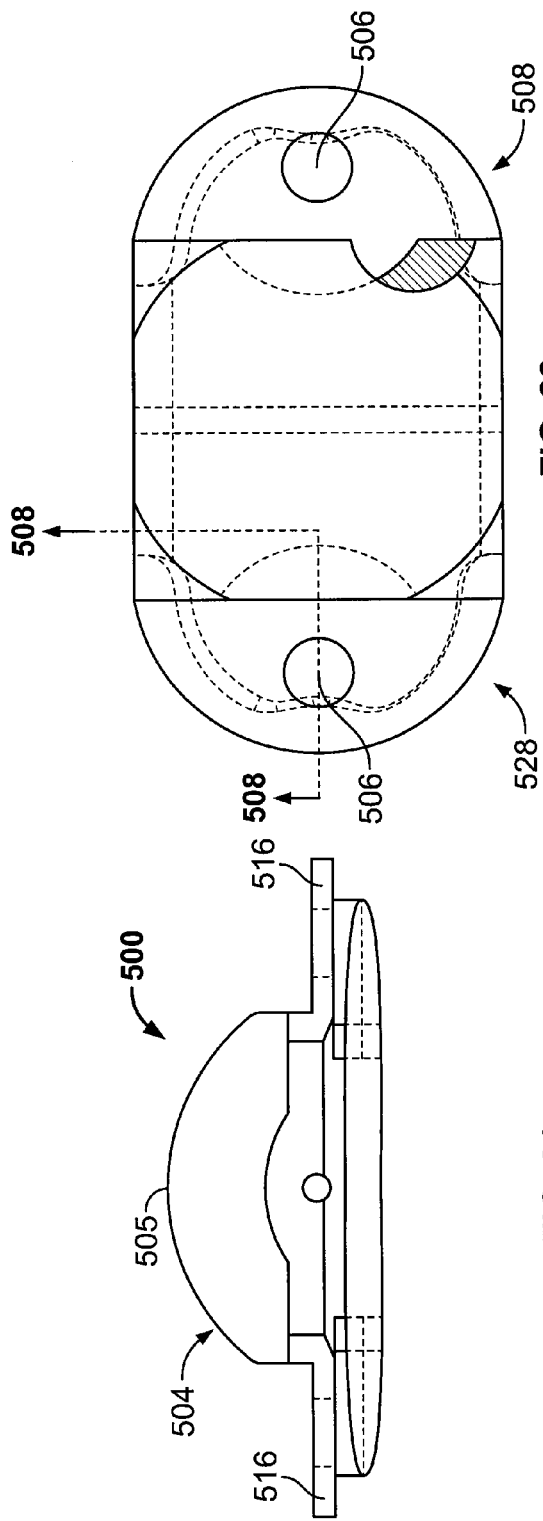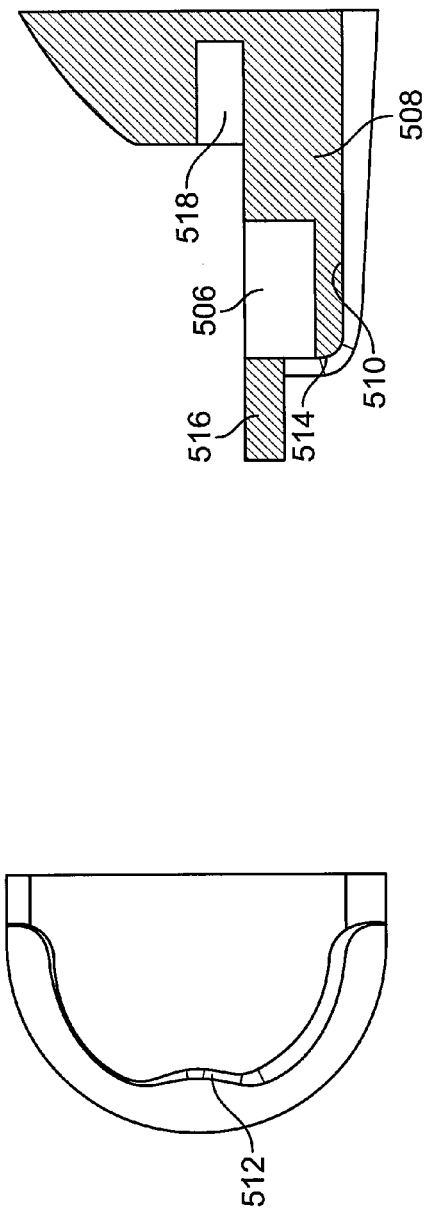

JOINT ARTHROPLASTY DEVICES HAVING ARTICULATING MEMBERS

CROSS-REFERENCE TO RELATED APPLICATION

This application claims the benefit of U.S. Provisional Applications 60/825,865 and 60/916,734, and is a continuation-in-part of U.S. patent application Ser. No. 10/971,734, filed Oct. 22, 2004, entitled "Artificial Disc Device," which is a continuation-in-part of U.S. patent application Ser. No. 10/692,468, filed Oct. 22, 2003, entitled "Artificial Disc Device," the specifications of which are incorporated herein in their entirety.

FIELD OF THE INVENTION

The present invention relates to artificial implants for replacing damaged or degenerated weight bearing joints, and in particular, to multiple component implants that permit rotational and/or sliding articulation of the multiple components.

BACKGROUND OF THE INVENTION

There are several types of joints in the human body. These can be categorized into weight bearing and non-weight bearing joints. The hip, knee, ankle and intervertebral disc in the spine are considered load-bearing joints, while the finger and toe are considered non-weight bearing joints. The hip, knee, and ankle are further categorized as synovial joints, while the intervertebral disc is a cartilaginous joint. These joints, especially the weight bearing joints, can undergo degenerative changes due to disease, age, trauma, repetitive loading and/or genetics.

For synovial joints, these degenerative changes come in the form of arthritis, or inflammation of the joint, leading to damage of the articular cartilage. Osteoarthritis mainly damages the joint cartilage, but there is often some inflammation as well. Rheumatoid arthritis is mainly inflammatory, and can eventually destroy the joint cartilage and adjacent bone. Fracture and other forms of trauma may also lead to degenerative changes. Osteonecrosis is a condition in which either the bone of the femoral head or femoral condyles dies. The dead bone cannot withstand the stresses of walking and as a consequence, the femoral head or condyles then collapse, become irregular in shape, and cause pain in the hip or knee joints.

The spinal intervertebral disc, which is situated between the vertebral bodies, is also subject to degenerative changes. The spinal disc is comprised of a tough outer ring call the annulus, and a jelly-like filling call the nucleus. Degeneration of the intervertebral disc can occur at a relatively young age, and is believed to be the major cause of low-back pain. It often begins with a structural change in which the nucleus loses its water-binding capacity and the disc consequently loses height. Typically this is manifested by desiccation of the nucleus. After this happens, more compressive loading shifts to the annulus, rendering this structure more susceptible to delamination and damage. This in turn can lead to fissures in the annulus with the possibility of a corresponding herniation of nucleus material. This leads to a decrease in the intervertebral disc height, encroachment upon the nerve roots and/or spinal canal and degeneration of other surrounding tissues.

The individual whose joints undergo such changes may incur significant discomfort, pain and even disability. Initially, the only option for the patient with degenerative changes to these joints was to undergo arthrodesis, or fusion, of the effected joint. Although this can effectively relieve pain and lead to an increase in the quality of life, fusion can significantly alter the normal biomechanical function of the effected joints. Treatment options have since advanced to include motion preserving implants, known as arthroplasty devices. These joint replacement devices usually comprise a pair of endplates with some type of intermediate components or articulating bearing surfaces to facilitate motion between the adjacent vertebral bodies.

Artificial knee joints have been provided which comprise a femoral component having a pair of metal condyles at the distal end and a tibial baseplate including a plastic articulation component mounted to the baseplate. The condyles articulate against the tibial articulation component to provide joint mobility. Known artificial hip joints typically include a stem inserted into the proximal femur, a generally spherical head mounted to the stem, and an acetabular cup housing a plastic wear liner. This creates a ball and socket type connection mimicking that of the natural hip.

In the spine as well, a primary surgical treatment for disc degeneration has been fusion. However, spinal fusion has proved to cause an increase in degeneration at other vertebral levels that must compensate for the loss of motion at the fused level, commonly causing the patient to relapse into more pain and limited mobility. Further advances have included the development of motion preservation intervertebral disc replacement devices. Such devices typically comprise a pair of biocompatible metal plates having outer surfaces for engaging the inferior and superior vertebral surfaces, and opposed inner articulating surfaces to support multi-axial motion. The inner surfaces of the plates may be lined with a hard polymer articulating core, or the plates may house an elastomeric core. Other known devices comprise a pair of metal plates with inner metal-on-metal articulating surfaces.

A key challenge for arthroplasty devices, whether for the hip, knee, ankle or spine, is selecting the proper materials for the various components thereof. Biocompatibility—the suitability of a material for exposure to the body or bodily fluids—and biodurability—the ability of a material to maintain its physical and chemical integrity after implantation in to living tissue—are essential for permanent medical implants. Materials chosen should avoid cytotoxicity, systemic toxicity, irritation, macroscopic or allergic reactions, muscle degeneration, or other adverse response. The biocompatibility and biodurability requirements significantly limit the selection of materials available for weight bearing devices.

The implant components must also exhibit sufficient strength and excellent fatigue performance to avoid mechanical failure over a long life under physiological loadings and kinematics. Properties such as yield strength, break strength, flexural strength, shear strength, and compressive strength of the implant components can significantly impact the success of the implant in weight bearing joint arthroplasty. Hard and stiff materials, such as ceramics or metals, have favorable strength characteristics. However, such materials have substantially higher flexural modules than that of cortical bone. This can cause a phenomenon known as "stress shielding," which may cause bone loss and the loosening and eventual failure of the implants. Certain polymer materials, having a flexural modulus similar to cortical bone, are thought to minimize stress shielding and the associated adverse effects. However, many polymers do not have sufficient yield strength to be used in weight bearing joints. One proposal has attempted to address these considerations by providing an intervertebral implant having outer plates made of a softer polymeric material to interface with the vertebral bone faces, and a hard ceramic or metal material for the inner articulating components. However, such a design is more complex to manufacture and raises further challenges in the need to inhibit slight motion between the two dissimilar materials combined in a single component of the multiple component implant to minimize wear and ultimate separation at those interfaces.

The problem of stress shielding also exists in other implants such as knee and hip replacements. In an artificial hip, for example, stress shielding may occur where a metal acetabular shell is secured directly to bone, and where the femoral stem is retained in the proximal femur. In a knee implant, stress shielding may cause bone degradation where a metal femoral condyles meet the distal end of the femur.

As exemplified in the devices described above, known hip, knee and ankle arthroplasty devices, and the majority of disc arthroplasty devices, incorporate articulation in their design. The articulation can be conforming, such as the ball and socket arrangement of the hip joint, or non-conforming, which permits sliding motion such as in known knee arthroplasty designs. In both conforming and non-conforming designs, the motion of the articulation surfaces against each other generates wear particulate. The primary wear that occurs in a hip prosthesis is between the femoral head and the acetabular cup. In a knee prosthesis, wear occurs primarily between the distal femoral condyles and the articulation surface of the tibial tray. The generation of wear particulate is important not only from a device lifetime perspective, but also from a biological perspective. In some cases, the biological response will dictate the lifetime of the device. This is because the generation of wear particulate in sufficient amount and size may lead to an adverse cellular response, manifested by macrophage activation, giant cell formation and a cascade of cytokine release ultimately leading to an imbalance in osteoclast and osteoblast activity. This may lead to inflammation of the tissue around the reconstructed joint, osteolysis and failure of the implant.

The wear performance of such devices is a function of the mechanical design as well as the relative material properties of the articulating components. For example, the degree and types of motion permitted, the contours of the articulating surfaces, contact geometry, speeds, loads, micro-motion between integrated components, surface roughness and lubricant and other factors can significantly impact the amount and nature of the wear debris. The material selection and device design must result in acceptable wear performance of the device under expected physiological loadings and kinematic conditions.

Early attempts to evaluate the wear properties of these devices typically involved the use of small scale testing apparatuses such as pin-on-disc or pin-on-plate configurations. A pin-on-disk wear simulator consists of a disk that is mounted to and driven by a turntable at constant speed in an environmental chamber. The disc is made from the metal, ceramic or polymer representing the first bearing surface. Test pins formed of the second material of the bearing couple are loaded against the turntable by either static weights or a hydraulic system. The mass loss of the pins may be determined as a function of sliding distance, and a wear factor calculated. This type of simulator likely underestimates the amount of wear that can occur when evaluating materials for orthopedic weight bearing applications, since it does not depict the actual kinematics of the joints.

Reciprocating pin-on-plate testing machines may better approximate the oscillatory sliding motion of synovial joints. The pins in such devices are similar to those used in pin-on-disk testing. However, the pins rotate while being statically loaded against a plate that oscillates back and forth. The mass loss of the pins may be determined as a function of sliding distance and the wear factor calculated. This type of simulator is believed to provide a more accurate evaluation of the wear performance of biomaterials in weight bearing joint applications.

An even more realistic prediction of clinical wear performance may be obtained using hip, knee and spine simulators. Hip and knee simulators are able to apply the necessary dynamic loads and the complex motions experienced in the clinical setting. These devices can produce the multidirectional motion profiles necessary to generate wear rates and wear particle morphologies that are similar to in vivo experience. There are currently several published regulatory standards and guides known to those skilled in the art for properly evaluating material combinations to be used in orthopedic weight bearing environments. Simulator testing consists of mounting the femoral head and the acetabular shell of the hip prosthesis, or the femoral condyles and tibial tray of the knee prosthesis, on the simulator and bathing it in a protienacious solution that is thought to mimic the synovial environment to which it will be exposed to in vivo. The simulator generates the loadings and motions of a typical gait profile. The duration of the test is generally from 5 to 10 million cycles of gait simulation or until a steady state wear is observed. One million cycles of testing is thought to represent the amount of walking the average person undergoes in one year. The test is stopped at predefined intervals, and the mass loss of the articulating components is measured. The wear rate is then determinable from the mass loss in a known manner.

Simulators that attempt to mimic the loading and range of motion of the intervertebral disc are also known in the art. However, the intervertebral disc is a more complex joint than that of the hip and knee, and there is presently no established protocol for assessing the wear in such device. The intervertebral disc has a complex multidirectional motion profile including rotational movements in the fore-and-aft direction and the lateral direction as well as rotation about the vertical axis. However, the fore-and-aft rotary motion component of the multidirectional motion profile of the intervertebral disc is the predominant motion component. The hip joint has a similar motion profile it must be able to undertake. The knee joint undertakes substantially unidirectional motion as by pivoting or rotational movement in the fore-and-aft plane. Nevertheless, whereas total joint simulator testing for the hip and knee has evolved to the point where there are several published standards by regulatory bodies for evaluating material combinations for artificial hip and knee joints, as mentioned it is generally recognized that the intervertebral disc is a more complex joint than that of the hip and knee with the load and kinematic profiles not being well understood.

The materials of fabrication also impact other important aspects of total joint arthroplasty devices beyond wear performance. For example, metal surfaces tend to generate scatter which prevents a complete inspection of tissue and bone growth using conventional imaging techniques such as X-rays, MRI and Computer Tomography. Radiolucent materials, such as polymer materials, generally do not interfere with the imaging of the surrounding bone and tissue using these techniques. Material selection may also impact required sterilization techniques, as certain biopolymers are known to oxidize when sterilized using conventional techniques such as steam sterilization. This may adversely affect the strength and/or the wear performance of the material.

A number of attempts to utilize polymer against metal bearing couples in weight bearing joint replacement device have been reported in the art. The relatively harder metal components can provide strength and durability to such devices, while the relatively softer polymer provides for a low friction interface. The polymeric materials also wears before the metal to minimize the generation of potentially harmful metal ions. However, many of the biopolymers investigated have been found to have insufficient yield strengths, wear resistance and/or biocompatibility and biodurability to succeed in weight bearing joint applications. And the requirement of metallic structural components creates additional drawbacks, such as interference with imaging and the previously mentioned phenomenon of stress shielding. Nevertheless, the use of polymer on metal bearing interfaces in such devices has met with some success, as described in more detail below.

Early hip replacement implants used Polytetraflourethylene (PTFE) as a bearing material against metal. Such devices typically included a stainless steel femoral head articulating against an acetabular cup made of PTFE. The PTFE provided a low coefficient of friction at the bearing interface, but its low yield strength and lack of durability purportedly led to excessive wear and severe inflammation of the periprosthetic tissue in clinical use. The use of glass filled PTFE and a mica filled PTFE has been shown to improve the wear rates when evaluated on a pin-on-plate wear tester. However, it has been reported that this did not translate to reduced wear rates clinically, and resulted in severe wear like that of unfilled PTFE.

The use of ultra-high molecular weight polyethylene (UHMWPE) against metal in total joint replacements has a long clinical history dating back decades. UHMWPE was proposed as a counterface to stainless steel due to its greater biocompatibility and increased wear resistance over PTFE when evaluated on pin-on-plate wear testing simulators. UHMWPE also possesses superior mechanical toughness and wear resistance over most other polymers. UHMWPE on metal hip joints have succeeded clinically, with high rates of survivorship beyond 25 years in some cases. However, UHMWPE is also known to have certain drawbacks and limitations. These include the need for small diameter head sizes to reduce the frictional torque due to less than optimal lubrication, oxidation of the UHMWPE resulting from ionizing sterilization, and wear caused by third body debris such a bone particulate.

A significant drawback of UHMWPE is the accumulation of wear debris eliciting an adverse cellular response leading to inflammation and osteolysis of the surrounding bone. The literature suggests a threshold wear rate of 80 mm$^3$/year, above which particle induced osteolysis may lead to failure. The clinical wear rate of UHMWPE hip implants can potentially exceed this value. It has been suggested that the UHMWPE wear volume can be controlled below the indicated threshold for osteolysis by limiting the diameter of the femoral head. However, a smaller head decreases the range of motion of the joint and elevates the risk of the neck of the femoral stem impinging upon the cup causing dislocation of the femoral head.

Another potential drawback of devices utilizing UHMWPE on metal bearing interfaces is the potential oxidation of UHMWPE. This has been shown to occur as a result of using gamma radiation or electron beam radiation for sterilization in an oxygen rich environment, and the subsequent storage of the polymer in air or exposure in vivo. Oxidation of UHMWPE causes the polymer to become more brittle, decreases the fatigue strength fracture resistance of the material, and makes it less biocompatible. It is believed that UHMWPE oxidation also decreases the wear resistance of the material. To avoid these problems, sterilization of UHMWPE implants must be performed in an inert environment, such as nitrogen.

The performance of UHMWPE on metal joint implants may also be adversely impacted by third-body wear particulate. For example, cements such as Polymethylmethacrylate (PMMA) are commonly used to secure the metal femoral stem of a hip prostheses into the femoral canal or the metal backing of the tibial tray to the tibial canal. PMMA particles can become entrapped between the head and UHMWPE acetabular cup. Such third-body wear particulate can also comprise bone or metal particles. This may lead to accelerated wear of the UHMWPE in such bearing couplings, either as a result of the abrasive effect of the particulate on the UHMWPE surface and/or by roughening the surface of the metal head bearing surface.

Attempts have been made to improve the wear resistance of UHMWPE on metal bearing couples by reinforcing the UHMWPE with carbon fibers. It has been suggested that carbon fibers would increase the modulus and the ultimate tensile strength of the UHMWPE, and decrease its creep properties, resulting in improved wear performance. However, reported simulator testing has been inconclusive, with some studies reporting less wear than conventional UHMWPE and others showing high wear rates. Carbon fiber reinforced UHMWPE on metal knee implants have not achieved clinical success. The clinical failure of this bearing couple is thought to be due to the carbon fibers being mechanically but not chemically bonded to the UHMWPE, the poor creep resistance of the UHMWPE which promoted debonding of the carbon fibers from the matrix, the tendency of the carbon fibers to scratch the metal counterface, and the high stress loadings of the knee joint.

Another drawback of UHMWPE on metal weight bearing joint implants is the potential for increased wear over time as a consequence of a cross-shearing effect on the UHMWPE. Conventional UHMWPE undergoes a molecular re-organization process under both unidirectional and multidirectional motion.

Normally, the lamellar structure of UHMWPE is randomly arranged. Under unidirectional motion, the shear and tensile stress vectors applied to the polymer chains within the wear surface cause the polymer chains to become oriented in the direction of the stress vector. This results in a strain hardening of the polymer and an increase in the wear resistance in the direction of travel as this motion continues. However, the strain hardening of the polymer in one direction leads to weakening of the polymer in the perpendicular direction. Multidirectional motion, consisting of tensile and shear stresses in multiple directions, thus results in strain hardening in the primary flexion/extension direction and the subsequent softening of the polymer in an off axis direction. It is believed that strain hardening of UHMWPE increases the long term wear of implants subjected to the complex multidirectional motion of weight bearing joints, and particularly with motion preservation intervertebral implants. Strain hardening also creates further challenges by making it more difficult to predict the clinical performance of the device through joint simulator testing.

Significant reductions in wear rates against metal have been realized by crosslinking the polymer chains that comprise UHMWPE. Gamma or electron beam radiation is used in various doses and with different types of remelting or annealing thermal treatments to reduce or eliminate residual free radicals. Crosslinking may also be performed via peroxide or silane chemistry. These techniques require further processing steps, add cost, and make control of material properties more difficult. Crosslinking of UHMWPE may lead to undesirable material changes such as decreased tensile and ultimate strength, and also a decreased elongation to failure. The addition of thermal treatments can make the polymer still susceptible to oxidation and reduce its fatigue strength, which could adversely impact clinical performance.

Despite the above drawbacks, total weight bearing joint arthroplasty devices utilizing UHMWPE on metal articulation couples, which originated in the hip and knee applications, have enjoyed moderate clinical success and are well accepted in the art. It is believed that the development of disc arthroplasty devices has benefited greatly from the established clinical history and lessons learned from the technological evolutions in the hip and knee arthroplasty industry. Although osteolysis remains a major concern of using UHMWPE, it has been used in several available total disc replacement implants since it is a proven material combination supported by an extensive clinical history. These devices typically consist of a UHMWPE core that has been moderately crosslinked articulating against Cobolt-Chromium (CoCr) endplates. The wear resistance of UHMWPE and its overall durability remains a concern, with some published wear rates being similar to those seen for hip arthroplasty. The high wear rates are a source of concern because disc arthroplasty devices are indicated for a much younger population, and the goal is to have such a device last the patient lifetime. Nevertheless, these devices have been used clinically with relatively few reported complications related to the UHMWPE material reported to date. However, they nevertheless suffer from the potential drawbacks of stress shielding and interfering with imaging associated with metal components, as discussed above.

Other polymer on metal bearing couples in weight bearing joint replacements have also been investigated. Thus, for example, one known hip replacement device utilized polyacetal articulating against a stainless steel femoral head. This device also incorporated a sleeve of polyacetal between the neck of the femoral stem and the metal ball. This prosthesis suffered from a high failure rate due to excessive wear of the polyacetal components. Osteolysis was also more prevalent than observed in UHMWPE hip replacements. Friction in retrieved polyacetal acetabular cups has been shown to be significantly greater than in retrieved polyethylene acetabular cups. These frictional characteristics of polyacetal can change as the material ages in vivo, making the long term performance of the material uncertain.

PEEK, or polyetheretherketone, is an engineering thermoplastic used in certain medical implant applications. It is available from at least one manufacturer, Invibio Ltd. of Lancashire, UK, in pure form and also in other formulations containing additives such as carbon fiber, barium sulphate and glass fiber. Carbon fiber reinforced PEEK (CFR-PEEK) and glass fiber reinforced PEEK include short carbon or glass fibers that increase the strength of the polymer for higher stress demanding applications. The material is also available as a composite comprising PEEK as a matrix polymer in combination with continuous carbon fibers for applications requiring even greater strength and rigidity. As used herein, the terms "PEEK material," or "PEEK-type material" are intended to include all materials of the polyaryletherketone family such as PEEK (Polyetheretherketone), PAEK (polyaryletherketone), PEK (polyetherketone), PEKK (polyetherketoneketone), PEKEKK (polyetherketoneetherketoneketone), PEEKK (polyetheretherketoneketone), and PAEEK (polyaryletheretherketone). It should be noted that the material selected can also be filled. For example, other grades of PEEK are also available and contemplated, such as 30% glass-filled or 30% carbon filled, provided such materials are cleared for use in implantable devices by the FDA, or other regulatory body. Glass filled PEEK reduces the expansion rate and increases the flexural modulus of PEEK relative to that portion which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

As will be appreciated, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention.

PEEK has been used to fabricate medical implants for fusion applications, such as spinal fusion cages, and in bone screws, pins and other applications not involving joint articulation. PEEK, like other polymers such as UHMWPE, has also been proposed as a material for articulation surfaces in self-mating bearing couples for non weight bearing joints such as a finger joint.

The use carbon fiber reinforced PEEK as an alternative to UHMWPE for articulation against a metal counterface in weight bearing arthroplasty devices has also been investigated. An assessment of the wear characteristics for CFR-PEEK articulating against CoCr using hip simulators showed a wear rate significantly lower than that of conventional UHMWPE on CoCr. However, it has been suggested that this material is not suitable for high stress environments such as in the knee joint. Regardless of the suitability of CFR-PEEK against metal in such applications, this bearing coupling still carries the above-described drawbacks associated with the use of metal structural and articulation components.

Certain cervical disc replacements are known to utilize polyurethane articulating against titanium. However, the wear resistance of that coupling is questionable, considering that the load encountered in the cervical region is roughly an order of magnitude lower than that of the lumbar region and the device has been reported to exhibits wear rates higher than the traditional UHMWPE on CoCr and metal on metal devices.

Early total joint arthroplasty devices utilizing metal on metal articulation surfaces were considered unsuccessful. Later attempts utilized the more wear resistant CoCr in place of stainless steel. However, the initial success rate proved to be unsatisfactory for reasons such as poor manufacturing tolerances, inadequate clearances, early impingement, poor material selection and increased failure rates due to high torsional forces, leading to loosening and accelerated wear. The introduction of cementing of the femoral shaft led to a decrease in the rate of loosening, and the success rate improved. However, because of their high initial failure rates and occasional dark staining of the periprosthetic tissues by metallic wear debris, these devices were largely supplanted by the acceptance of the metal on UHMWPE designs as the primary choice for use in total joint arthroplasty.

Even so, a large number of metal on metal hip prostheses have reportedly functioned successfully for more than two decades. The average volumetric wear rates are reportedly on the order of 10 to 200 times less than that typically seen in conventional UHMWPE bearings, with little or no biologic response to the wear process. It therefore appears that the problems undermining the clinical success of the first generation implants were primarily from sub-optimal implant design and not the inherent wear resistance of the bearing couple itself. Given the potential for greatly improved wear performance, further investigation into metal on metal hip arthroplasty devices has led to improved manufacturing techniques and material selection resulting in improved metallurgy, sphericity, surface finish and clearances. Reported hip simulator testing and clinical retrieval data suggest that these advances have further reduced the volumetric wear and improved clinical survivorship rates.

Perhaps due to the low wear characteristics and longer expected lifetime, metal on metal disc arthroplasty devices have also been pursued in the art. Although decreased wear rates are reported for these metal on metal bearings in comparison to CoCr on UHMWPE, the metal particles generated are smaller and greater in number than in a conventional UHMWPE bearing, and may present an overall active surface area similar to that of UHMWPE. These soluble metal particulates lead to elevated chromium, nickel and molybdenum levels and may result in hypersensitivity and potential toxicity, carcinogenesis and mutagenicity. Therefore, metal on metal bearings in spinal disc arthroplasty continue to suffer from the perception of elevated ion exposure potentially leading to elevated health risks, in addition to other drawbacks such as stress shielding of adjacent bone and interference with imaging of the surrounding tissue.

Further attempts to reduce wear rates and potentially alleviate the problem of osteolysis have included the pairing of biopolymers and ceramics in weight bearing joint replacement devices. Ceramic materials generally have increased hardness, the potential for a smoother surface finish, and are less susceptible to scratching compared to metals. Ceramics also provide better wettability compared to metals and therefore offer improved lubrication. Simulator studies of an artificial hip comprising a ceramic femoral head articulating against a UHMWPE acetabular cup demonstrated a very low wear rate for this bearing couple. However, the same reduction in wear rates has not been consistently demonstrated clinically in reported radiographic studies.

Another attempt paired CFR-PEEK as an acetabular cup articulating against a ceramic femoral head in a hip prosthesis. It has been reported that optimization of the percent carbon reinforcement results in a wear rate of the acetabular cup that is significantly less than that of conventional UHMWPE when paired with CoCr, alumina or zirconia. However it has also been suggested that that CFR-PEEK should only be used in a conforming bearing surface, such as an acetabular cup for a hip joint for supporting a metallic or ceramic femoral ball, and would not perform well as in a high stress, non-conforming contact situation such as a tibial component in a knee joint.

Still other investigators have reported on total joint arthroplasty devices comprising ceramic on ceramic articulation interfaces. As mentioned, ceramics are much harder than metal, resulting in increased scratch resistance, and they can also be manufactured to a much smoother surface finish. They are also hydrophilic, permitting a better wettability of the articulating surface. The improved wettability and finish of the articulating surface results in a fluid film that offers a reduction in the coefficient of friction as compared to metal on metal.

Early reported attempts utilizing alumina ceramic on ceramic bearings in hip replacements resulted in poor clinical results, with high wear or fracture resulting in high failure rates. Improved manufacturing and design has resulted in much lower reported fracture rates for current generation alumina femoral heads. Other devices have utilized zirconia, which has a significantly greater fracture strength and toughness than alumina. The suitability of zirconia as a self mating bearing couple is a subject of considerable disagreement in the art, with some investigators reporting severe wear, possibly as a result of thermal instability, and others reporting very low wear. More recent efforts have led to the development of alumina-zirconia composite ceramics for joint arthroplasty devices. This combines the high strength of zirconia with the thermal stability of alumina.

Ceramic on ceramic bearings have demonstrated the lowest in vivo and in vitro wear rates to date of any bearing combination. Ceramic bearings do not share the same biological concerns from generated particulate debris as metal bearings, as they are considered to be relatively biologically inert. However, ceramics are prone to material failure when subjected to high mechanical stress, either in tensile or impact loading, which may limit their long term potential total weight bearing joint arthroplasty.

Other weight bearing joint replacement devices have been proposed that utilize compliant bearing surfaces provided as coatings of metal structural components. For example, one known attempt involved the use of a compliant material as a surface covering of a metal femoral ball articulating against the native cartilage of the acetabulum. Materials for use have included silicon rubbers, polyurethanes and olefin based synthetic rubbers. These devices have been shown to operate with very low friction because of the fluid-film lubrication that they exhibit, and therefore should produce lower wear than current prosthetic materials as the two surfaces of the joint are completely separated by a film of synovial fluid. They have been shown to possess a balance of physical strength, flexibility, dynamic flexural endurance, inherent chemical stability and physiological compatibility. The use of elastomers such as polyurethane as an articulating weight bearing material have not shown any benefit in terms of wear resistance over the more traditional bearing couples, and this may lead to questions regarding their biodurability and subsequent biocompatibility.

Thus, as detailed above, the stringent requirements for permanent articulating weight bearing arthroplasty devices have restricted the possible material selection, material treatments and surface designs that can be used in clinically viable products. Because of these significant limitations, the predominating material couplings for the weight bearing arthroplasty devices are metal on UHMWPE, metal on metal, and ceramic on ceramic. Cobalt chrome self-mating devices have been shown to have superior wear resistance over UHMWPE, but elevated metal ions and delayed type hypersensitivity has been seen as a potential clinical issue. The potential carcinogenicity due to metal ion exposure has not been resolved. Metallic components also cause stress shielding effects and interfere with imaging. Ceramic on ceramic couples also exhibit high wear resistance, but they suffer from limited design options and may potentially fracture under physiological loadings. Other combinations have also been studied and undergone various degrees of development and implementation. Some of these material combinations have shown promise when tested in the laboratory, but many have also failed laboratory testing, and few have translated into clinical success.

Solutions to the drawbacks associated with the design and material selection of previously proposed arthroplasty devices have remained elusive. Few attempts to provide polymer against polymer bearing surfaces in weight bearing total joint arthroplasty devices have been reported. One attempt involved the use of polyacetal articulating against UHMWPE. In vitro comparisons using hip simulators of polyacetal articulating against UHMWPE with UHMWPE articulating against CoCr showed lower friction and wear in the all polymer combination. Although formaldehyde, a product of the degradation of polyacetal degradation, was present in trace amounts in some lubricant samples, the initial study demonstrated the potential of this bearing couple for clinical applications. Reported results of a subsequent clinical trial using a knee prosthesis consisting of a polyacetal femoral component bearing against a conventional UHMWPE tibial tray suggested performance comparable to metal on conventional UHMWPE implants. Recovered implants demonstrated only minor signs of wear and biological activity. However, sterilization of polyacetal with gamma radiation in air results in a material change, manifested by a change in color. Also, cementless fixation of the polyacetal component has been reported to be inadequate, resulting in high rates of aseptic tibial loosening and infection. As a result, polyacetal has not been considered a viable alternative to using metal as the counter bearing material to UHMWPE.

The use of UHMWPE self-mating bearing couplings, i.e. where both articulating components have UHMWPE bearing surfaces, is also considered infeasible in weight bearing joints due to the low yield strength and high wear associated with this material. Instead, the use of polymeric self-mating bearing couples has been confined to non-load bearing joints such as the finger. In this regard, it has been noted that cross-linked polyethylene (XLPE) can be used as a self-mating bearing couple in the finger since the wear rate, although approximately six times greater than for non-cross linked UHMWPE against stainless steel bearing couple, still provides sufficient wear resistance for applications with low loading, such as the metacarpo-phalangeal joint of the finger.

Apparently due to the known limitations of common biopolymers discussed above, such as low yield strength leading to adhesion deformation, high wear caused by third body particulate, cross shearing and/or oxidation, the path of development of arthroplasty for weight bearing joints has largely bypassed polymer on polymer bearing couples. Indeed, many of the biopolymers investigated were found to have insufficient strength, wear resistance and/or biocompatibility to succeed in weight bearing joint applications when paired against metal or ceramic components. Devices that have incorporated polymer bearing materials with some success, namely UHMWPE or polyurethane, have also incorporated much harder metal or ceramic components to serve as the major structural members and as bearing counterface materials for mechanical strength and wear performance. Thus, all polymer combinations have generally been excluded as an acceptable self-articulating material combination for use in weight bearing joint replacements.

There is in particular an extensive history of failure when polymers articulate against polymers in weight bearing artificial joints. PEEK has been suggested as an appropriate structural material for use in medical implants due in large part to its strength, radiolucent nature, and biocompatibility. The primary applications of this material have been in structural implants having no articulating component. A PEEK on PEEK articulation interface for non-weight bearing joints such as in finger joints has been proposed by one investigator. This is consistent with the prior art teachings that self-mating polymeric bearing couples should not be employed in load bearing joints. However, the prior art lacks any suggestion of weight bearing joint arthroplasty devices comprising PEEK as a primary structural material and having PEEK on PEEK articulation interfaces to support the complex multidirectional motion required for such joints under physiological loadings. In view of the failure of polymer on polymer bearing couples to achieve clinical success in weight bearing joint arthroplasty devices, and the lack of knowledge of wear and other performance characteristics of PEEK on PEEK combinations under physiological loadings and kinematics, there has been no known motivation in the art to develop implants comprising PEEK on PEEK articulation interfaces for these rigorous applications. To this end, conventional approaches to bearing couplings teach that having surfaces of the same material bearing and articulating against one another, i.e. self-mating bearing couples, will not lead to acceptable performance. In particular, if the same metal material is used for both bearing surfaces galling of one or both of the metal surfaces is likely to occur under sustained loading. Similarly, where the bearing surfaces are of the same polymer material, there is the problem of surface adhesion under high loads, e.g. beyond the yield point of the polymer material, that has led to use of articulating load bearing members of different materials in artificial load bearing joints, such as metal on UHMWPE in artificial intervertebral joints.

Thus, there is a need for weight bearing total joint arthroplasty devices having excellent strength, biocompatibility, biodurability, friction and wear characteristics for high performance, longer life and lower risk of adverse responses such as particulate induced inflammation and osteolysis. There is also need for such devices having articulating surfaces that do not produce potentially harmful metallic wear particulate. Ideally, known problems of using polymeric articulation surfaces, such as higher failure rates and the increased wear associated with strain hardening caused by multidirectional motion, could also be overcome. Such devices are needed for applications requiring conforming bearing surface, such as an acetabular cup for a hip joint, and also for high stress, non-conforming contact applications such as in a knee joint.

There is also an unmet need for devices that meet these requirements while also being substantially radiolucent for improved imaging of the affected area. Ideally, such devices would also have a modulus of elasticity closer to the adjacent bone tissue to minimize the adverse effects of stress shielding on the adjacent bone. There is a further need to reduce the number of components in such total joint arthroplasty devices so as to provide fewer modes of failure, to reduce parts inventory and simplify manufacturing and assembly. Such devices should also be readily sterilized using conventional radiation or steam sterilization techniques without causing oxidation and associated adverse effects. Ideally such devices could be provided for the major weight bearing joints in a range of sizes required to serve the full patient populations for various degenerative joint conditions.

SUMMARY OF THE INVENTION

The present invention overcomes several drawbacks of the prior art by providing orthopedic weight bearing arthroplasty devices having opposed bearing or articulation surfaces both formed of the same polymeric material, and preferably of a PEEK material so that one PEEK material surface bears against another PEEK material surface (PEEK on PEEK material articulation surfaces). It has been found that articulating members having bodies including bearing surfaces thereof formed of the same polymeric material can provide optimized wear resistance comparable to that of metallic bearing couples even when subjected to extreme test conditions such as including coupled motion and load profiles that have mismatched or shifted frequencies. Similarly, the polymeric articulating members also avoid strength loss due to strain hardening even when subjected to these harsh testing conditions unlike UHMWPE, as previously discussed. Unexpectedly, it has been found that the wear rate of the implant herein having articulating members of the same polymeric material is not only better than that in conventional UHMWPE and metal bearing couples commonly used in intervertebral artificial disc and nucleus applications, but that the wear rate is an order of magnitude lower than these conventional bearing couples. This is true even where one of the bearing surfaces includes a thin arcuate wall portion on which it is formed. Even with a thin wall bearing portion, the polymeric articulating members still provide the optimized strength and wear resistance, as discussed above.

The PEEK material articulating members can be provided with relatively small features for being engaged by metallic components of an insertion tool for advancing the implant into the intervertebral spaces. These small features generally have relatively narrow dimensions so that during insertion they experience high concentrated forces thereon as applied by the metal engaging portions of the insertion tool. The features can include a post for being engaged by a metallic arm of the tool and/or arcuate surface portions for being engaged by a metallic tip of the tool with the post and arcuate surface portions being of the same polymeric material as the bodies of the polymeric articulating members. The increased strength of the polymeric bodies allows for the narrow and small features to have a secure, generally mating fit with the metallic insertion tool components that cooperate therewith during insertion and apply high loads thereto.

The invention has particular application in the replacement of hip, knee and ankle joints, as well as in intervertebral arthroplasty devices. In one aspect, the joint replacement implants of the invention have self-mating PEEK on PEEK articulation surfaces. In another aspect, the implants have self-mating carbon fiber reinforced CFR-PEEK on CFR-PEEK articulation. Still another aspect of the invention relates to orthopedic weight bearing arthroplasty devices having CFR-PEEK on PEEK articulation. The implants disclosed herein may include one or more surfaces that are coated with a bone ingrowth material such as hydroxyapatite to assist in securing the implants to adjacent bone tissue.

In one form of the invention, weight bearing total joint arthroplasty devices are provided in which both the opposed articulation surfaces and major load and stress bearing structural components are comprised substantially of PEEK and/or CFR PEEK. Devices provided in accordance with this aspect of the invention do not utilize metallic materials as primary structural or articulation components. For example, weight bearing total joint arthroplasty devices are provided comprising PEEK and/or CFR PEEK, and in which the only metal components are radiopaque markers used for detecting the position of the device via imaging techniques. The metallic markers in such embodiments are preferably displaced from the primary articulation and wear surfaces so as to avoid the generation of potentially harmful metallic wear particulate. The artificial joint implants in accordance with this aspect of the invention have fewer components because both structural and articulation requirements are met by use of the same material; whereas previous known designs utilized a plurality of materials to satisfy these constraints. As a consequence of having fewer components and/or avoiding layers of different materials, these devices offer the potential for fewer modes of failure, reduced inventory, and simplified lower cost manufacturing and assembly.

Due to the use of PEEK material, devices disclosed in accordance with this aspect of the invention are strong and durable, with high-impact strength and excellent flexural and tensile properties. The devices are substantially radiolucent so as to not interfere with imaging of the joint area. Because the implants disclosed herein have a modulus of elasticity closer to the bone tissue they are implanted in, they are less prone to damage the adjacent bone by stress shielding effects compared to more rigid materials. The disclosed devices are also highly biocompatible and biostable. They can be repeatedly steam and gamma sterilized with no detrimental effects on bulk material properties, and resist attack by a wide range of organic and inorganic chemicals and solvents.

The present invention further encompasses weight bearing implants which utilize metallic and/or ceramic materials as structural components with PEEK or CFR-PEEK on each articulating surface of the implant. Such designs may be appropriate in certain applications, although may be less preferred due to the increased number of material layers and/or components required and the drawbacks of using metallic components.

The joint implants disclosed herein have low coefficients of friction at the interface between opposed articulation surfaces of PEEK material, and can be designed to permit a full range of complex multidirectional motion in weight bearing joint applications. As disclosed further herein, embodiments of the present invention have been shown to have surprisingly favorable wear characteristics when evaluated by rigorous simulator testing protocols. The joint implants made in accordance with the invention offer the potential for low wear rates similar to metal on metal devices, while overcoming the known problems associated with the use of metallic structural and articulation components. These devices may also exhibit minimal strain hardening and cross shearing when subjected to complex multidirectional motion under physiological loadings, a phenomenon that has proved detrimental to other polymeric materials such as UHMWPE. These wear test results disclosed herein demonstrate that PEEK on PEEK articulation is a viable alternative for articulating orthopedic weight bearing arthroplasty devices, and that, in accordance with the principals of the present invention, clinically feasible arthroplasty devices comprising substantially all polymeric material can be provided.

The principles of the invention are particularly suited for providing intervertebral disc replacements for all or a portion of the natural intervertebral disc. Thus, multi-piece artificial disc and artificial nucleus replacement devices are provided comprising PEEK material in both structural and joint articulating components. In one form, a two-piece artificial nucleus device for insertion within the annulus is disclosed. The nucleus device comprises an upper shell having a substantially concave recess portion and the lower shell comprising a substantially convex portion. Each shell is fabricated from PEEK material, with the opposed convex and concave surfaces forming an inner or central articulation interface and the superior and inferior outer shell surfaces engaging the vertebral endplates.

In another aspect of the invention, improved total disc replacement devices are disclosed, which comprise upper and lower shells of PEEK material which form an internal convex-concave articulation interface. The artificial disc device may comprise one or more restraint structures located on one or both of the shell members to help keep the shells from becoming dislodged or migrating across the boney endplate of the vertebrae with the annulus removed. The restraining portions may provide, for example, in the form of directional teeth on the endplate facing surface of one or both of the opposed shells. Such an artificial disc offers benefits as a lumbar disc replacement, and is particularly well-suited as cervical disc replacement because it can be sized to fit the small space that the cervical disc occupies while still providing the necessary strength and wear resistance desired despite decreased contact area in such smaller artificial disc devices.

Also disclosed are improved artificial knee joints made in accordance with the invention. One embodiment of a knee joint may comprise a PEEK material femoral component that articulates directly on a PEEK material articular surface associated with a tibial baseplate. The PEEK material surface of the baseplate may be provided as an internal liner of a ceramic or metallic baseplate, or the baseplate itself may be formed of PEEK.

Improved artificial hip joints disclosed in accordance with the invention may comprise at least a femoral head of PEEK material for articulation against a PEEK material liner internal to the acetabular shell. Alternatively, the acetabular shell and the liner may be integrated into a single component formed of PEEK material. The stem and the femoral head may be integrated into a single component formed of PEEK material. Alternatively, they may be provided as separate but mechanically connected components of PEEK material. As a further alternative, a femoral head of PEEK material may be utilized in combination with a metallic stem and neck components. In each of these embodiments, the articulating joint surfaces have PEEK material articulating against PEEK material.

The radiolucent PEEK material implants of the invention may include one or more radiographic markers that are detectable by X-ray or other imaging techniques to assist the surgeon in positioning the implant during surgery and to monitor its location post-operatively. Typically these markers will be encased in predetermined locations in the implant at their periphery. Coatings which create subtle outline of the implant device during imaging may also be used, or additives such as Barrium Sulphate may be included to provide some radiopacity to the implant.

The implants disclosed herein may be fabricated using known techniques of machining predetermined sized blocks of PEEK material and, optionally, followed by surface polishing operations. Alternatively, the devices can be made by injection or compression molding of molten PEEK material in a conventional manner. In either case, it has been found that there is no need for additional processing of the PEEK material such as by cross-linking treatments to increase resistance to strain hardening as required with UHMWPE. Instead, pure PEEK material as provided by the manufacturer can be used to form the bearing components herein.

Implants disclosed herein may also include osteo-conductive or osteo-inductive surfaces or coatings in contact with adjacent bone or tissue to assist in securing the implant in a predetermined location. Examples of such coatings are hydroxyapatite, calcium phosphates such as tricalcium phosphate, or porous titanium spray.

BRIEF DESCRIPTION OF THE DRAWINGS

FIG. 3 is a partial cross-sectional view corresponding to FIG. 1 showing the members connected in the insertion configuration and an inserter tool for implanting the artificial disc device;

FIG. 4 is a partial cross-sectional view corresponding to FIG. 3 showing a grip member of the inserter tool extended relative to a grip shaft to grip the artificial disc device for implantation;

FIG. 21 is a side elevational view of a lower articulating member of another intervertebral implant in accordance with the present invention showing a convex, dome bearing portion thereof;

FIG. 22 is a plan view of the lower articulating implant member of FIG. 21;

FIG. 23 is a fragmentary, bottom plan view of one end of the lower articulating implant member showing an arcuate surface for engagement with an insertion tool;

FIG. 24 is a cross-sectional view taken along line 58-58 of FIG. 22 showing a lip projection overlying the arcuate surface, a recess adjacent to the lip projection, and an undercut recess in the dome bearing portion for cooperating with an insertion tool;

DETAILED DESCRIPTION OF THE PREFERRED EMBODIMENTS

Figure 1:
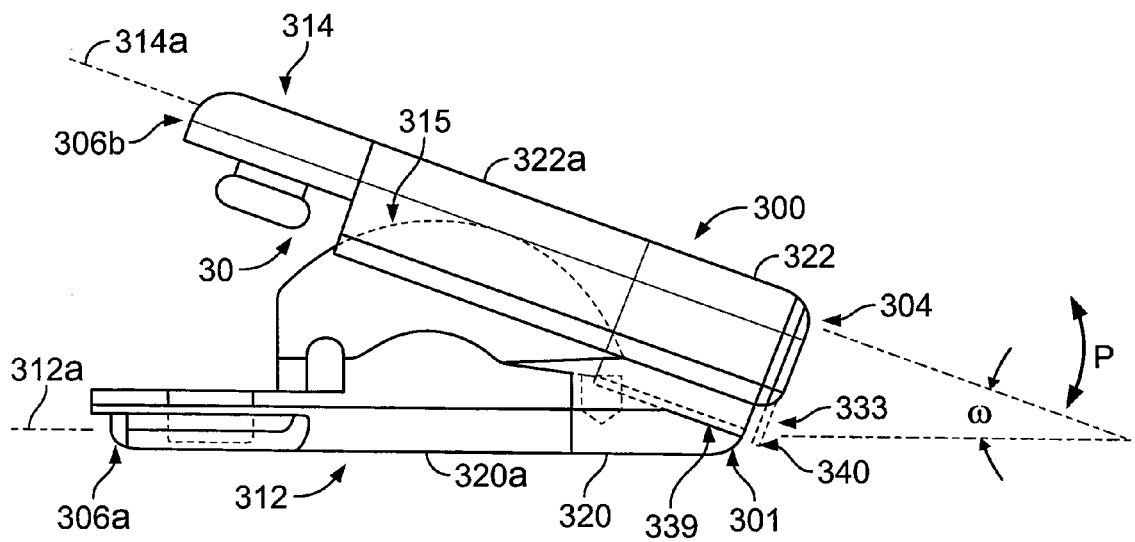
FIG. 1 is a side elevational view of an artificial disc device in accordance with the present invention showing upper and lower members releasably connected in an insertion configuration.

Referring now to FIGS. 1-16, embodiments of an artificial disc device 300, in the form of a nucleus replacement device, are illustrated. The implant 300 has a body 301 formed from two pieces including a lower member or shell 312 and an upper member or shell 314 having respective outer surfaces 320, 322 for contacting the endplates of adjacent vertebrae. The shells 312 and 314 are preferably both formed of a PEEK material, such as pure PEEK or CFR-PEEK. As such, the artificial disc device 300 is characterized by high strength, stiffness and toughness so as to provide favorable mechanical performance under the demanding conditions of the intervertebral joints, including both lumbar and cervical intervertebral discs. The disc device 300 is also highly biocompatible. The PEEK material shells 312 and 314 are radiolucent, and thus do not generate scatter or imaging artifacts during inspection of the joint tissue and bone growth using imaging techniques such as X-ray, MRI and Computer Tomography. The implant 300 is also readily sterilized using conventional techniques such as steam, ethylene oxide and gamma radiation without affecting the mechanical properties of the implant or its biocompatibility.

As illustrated in FIG. 1, to allow the members 312, 314 to shift relative to each other, a bearing interface 315 is formed between the opposed convex and concave PEEK material surfaces of the members 312, 314. More particularly, the lower member 312 has an arcuate or dome bearing portion 319 which articulates against recessed bearing portion 317 of the upper member 314. The recess 317 and dome portion 319 may be reversed to be formed on the lower member 312 and upper member 314, respectively. In one form, the dome portion 319 and recessed portion 317 have matching or approximately matching radii to maximize surface contact area. Alternatively, the dome bearing portion 319 may have a mismatched radius relative to the recessed bearing portion 317, such as to provide for additional sliding motion at the articulation interface. Matching the radii of the dome portion 319 and recessed portion 317 will typically provide improved wear characteristics. However, because the PEEK surfaces are somewhat resiliently deformable, the bearing surfaces may have mismatched radii while still providing an acceptable wear rate.

The respective articulating surfaces 319a and 317a of the dome portion 319 and the recessed portion 317 are preferably provided with a smooth surface finish of the PEEK material. A smooth finish on these surface will typically reduce the wear rate at the interface 315. The surface finish may have a particular impact on the amount of wear generated during the initial wear in period of the implant, which can be a significant portion of the total wear. In one embodiment, the surface roughness of the dome and recessed portion surfaces is less than about 120 Ra, more preferably less than about 60 Ra, and most preferably less than about 30 Ra. Surface finishes in these ranges may be achieved by conventional machining operations from blocks of PEEK material. Subsequent polishing operations may also be performed to achieve an even smoother finish. The appropriate surface finishes may alternatively be provided by fabricating the shells 312 and 314 from the PEEK material using conventional injection molding or compression molding techniques.

Due to the PEEK material surfaces 319a and 317a of the dome and recessed bearing portions 319 and 317, the bearing interface 315 provides for low friction pivoting, rotational and/or sliding articulation for complex multidirectional motion of the shells under physiological loadings and kinematics. The PEEK on PEEK interface 315 also results in the implant 300 having very favorable wear characteristics such that the mechanical properties of the device can be maintained over a long life time, while minimizing the risk of adverse effects such as osteolysis caused by excessive wear particulate.

The motion between the shells 312 and 314 could be limited to pivoting about a single axis or two axes by the use of motion limiters located on or between the members 312, 314.

The implant 300 is inserted between adjacent lower and upper vertebrae with the shell members 312 and 314 preferably connected to each other as will be described hereinafter. The convexity or concavity of the outer surfaces 320, 322 of the implant members 312, 314 may match or slightly mismatch the contours of the adjacent vertebrae. The outer surfaces 320, 322 may also be flat, and one or the other may be either flat, convex, or concave while the other is not. In one preferred embodiment, the surface 320 of the lower shell 312 is substantially flat and the surface 322 of the upper shell 314 has a convex profile approximating the concave surface of the upper vertebral endplate. Such an embodiment addresses the fact that the superior vertebral endplate of the lower vertebrae is often generally flat, while the inferior vertebral endplate of the upper vertebrae can be expected to have a more convex profile. This embodiment may thus provide greater contact between the surfaces 320 and 322 and the adjacent vertebral endplates with more even distribution of loads between the adjacent vertebrae and less potential for the implant to migrate within the annular space.

The mechanical properties of shells 312, 314 are preferably tailored for optimal performance in a given region of the spine, i.e. lumbar, cervical, etc., by selection of the specific formulation of PEEK material used to fabricate the shells. Material properties of several forms of PEEK material are available from the manufacturer, and this information may be used to select an appropriate grade of PEEK material required to achieve the desired mechanical performance. The tensile strength, flexural strength and flexural modulus of the shells 312, 314 increase as the amount of carbon fibers in the formulation increases. Thus, in one embodiment, the shells 312, 314 are each formulated from pure PEEK without reinforcing fibers. In another embodiment, the shells are formulated from CFR-PEEK containing about 30% by weight carbon fibers for greater strength and rigidity.

Pure PEEK, and carbon reinforced formulations can have a flexural modulus that is similar to the modulus of the cortical bone of the adjacent vertebral endplates. The flexural modulus of the shells 312, 314 is significantly less than that of metals such as cobalt chromium, stainless steel, titanium or alumina conventionally used in disc arthroplasty devices. As indicated above, metallic implants, with a substantially higher flexural modulus than cortical bone, can cause stress shielding leading to degradation of the adjacent bone tissue. Because the shells 312, 314 of implant 300 have a flexural modulus similar to that of the vertebral endplates, the adverse effects of stress shielding are mitigated.

The surfaces 320, 322 preferably lack any structure such as teeth, spikes or other structure that would penetrate and potentially damage the vertebral endplates. However, one or both surfaces may include osteo-conductive or osteo-inductive coatings to promote bony in-growth and thereby assist in securing the implant to adjacent bone tissue in a predetermined location. Examples of such coatings are hydroxyapatite, calcium phosphates such as tricalcium phosphate, or porous titanium spray. In some cases, a combination of coatings may be added. For instance, the adhesion of a hydroxyapatite layer may be enhanced by first coating a PEEK material implant with a thin layer of titanium and then applying the hydroxyapatite coating to the titanium layer over the PEEK material.

The implant 300 and the shells 312, 314 have a generally racetrack shape with an anterior-posterior length dimension D2 that is smaller than a lateral width dimension D1 including sides 303a and 303b. The implant 300 is inserted advantageously utilizing a narrower, leading or forward end 304 having the minor dimension D2. The implant 300 has a longitudinal axis 300a extending from the leading ends 304a, 304b to respective trailing ends 306a, 306b, and a lateral axis 300b extending between the substantially longer sides 303a, 303b. The longitudinal and lateral axes of the implant members 312, 314 define general planes in which each of the members 312, 314 generally extend. Consequently, the incision 308 in the annulus 309 need only have a length sufficient to accommodate the lateral width D2. During or after insertion, the implant 300 may be rotated so that the smaller, lateral dimension D2 is no longer exactly aligned with the incision 308 and inserted to bring the larger, lateral dimension D1 into at least partial alignment with the incision 308 after implantation. In this manner, the size of the incision 308 made in the annulus 309 for insertion is minimized. In addition, by turning the implant 300 in the nuclear space, it is captured in the space by the annulus 309 and is less prone to back out of the smaller incision 308 generally aligned with one of the longer sides 303a, 303b of the implant 300 adjacent thereto.

With the preferred oval or racetrack configuration, the leading end 304 of the implant 300, and specifically the ends 304a, 304b of the disc shell members 312, 314 are curved in the general plane of the members to ease insertion through the incision 308. On the other hand, once the implant 300 has been inserted and rotated such that the substantially longer sides 303a, 303b of the implant members 312 and 314, are aligned with the incision, the orientation of the substantially longer sides 303a, 303b make it highly unlikely that the members 312, 314 will back out through the incision 308 after implantation. Moreover, in the present preferred embodiment the substantially longer sides 303a, 303b are generally straight, further contributing to the resistance to backing out by the implant members 312, 314.

Figure 26:
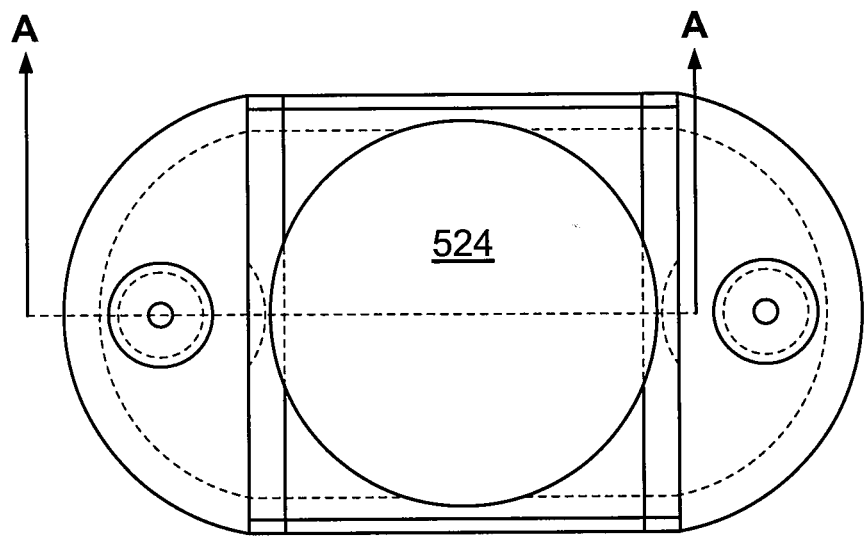
FIG. 26 is a plan view of the upper articulating implant member showing a recess bearing portion between the posts.
Figure 27:
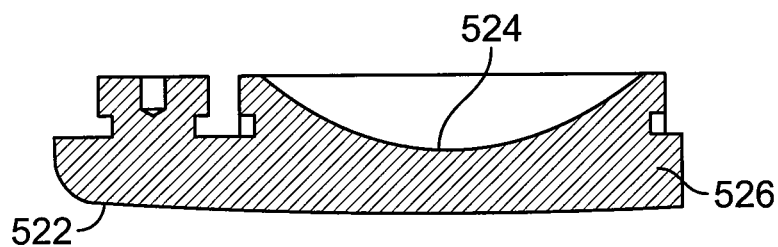
FIG. 27 is a cross-sectional view taken along line 61-61 of FIG. 26 showing a concave bearing surface and a thin walled portion of the recess bearing portion.

The artificial disc members 312, 314 are preferably connectable to each other so that the disc device 300 can be inserted as a single unit. To this end, the disc members 312, 314 can be connected so that they assume an insertion configuration that enables efficient implantation of the disc assembly 300 while minimizing the invasiveness thereof in terms of the incision size required therefor in the annulus 309. As shown in FIGS. 23 and 26, the insertion configuration of the disc unit 300 is preferably a wedge configuration so that a low profile, leading end 304 of the unit 300 is formed. At the trailing end 306 of the unit 300, the disc members 312, 314 are oriented away from each other so that the trailing end 306 has a larger profile than the leading end 304.

Thus, the insertion configuration for the artificial disc assembly 300 allows a surgeon to initially insert the leading end 304 through the narrow, slit incision 308 formed in the fibrous annulus material with resistance to the initial stage of the implant insertion kept to a minimum. Continued insertion of the unit 300 spreads the incision 308 apart to allow the entire implant 300 including the enlarged trailing end 305 to be inserted into the nuclear space 311. The bearing portion or interface 315 between the implant members 312, 314 acts as a fulcrum between the members 312, 314. During initial insertion, the force exerted on the top and bottom surfaces 322, 320 is toward the leading side of the fulcrum of the bearing portion 315. As the implant 300 continues to be advanced into the annulus 309, the force will shift rearwardly along the surfaces 320, 322 toward the trailing side of the bearing fulcrum. Eventually, the force exerted on the trailing side of the fulcrum of the implant members 312, 314 will exceed that on the leading side of the fulcrum to a sufficient extent that the implant members 312, 314 will be shifted to the operable configuration, as will be described below. As such, the wedge insertion configuration assists both in inserting the leading end 304 of the implant 300 and in enabling efficient shifting of the disc device 300 to the operable configuration in the nuclear space 311 between the adjacent upper and lower vertebrae 321 and, specifically, the end plates 313 thereof.

More particularly, the respective axes 312a and 314a of the disc members 312 and 314 form an insertion wedge angle ω which, along with the length of the disc members 312, 314, dictates the extent of the separation of the trailing member ends 306a and 306b. To maintain the insertion configuration of the disc unit 300, the disc members 312, 314 have a releasable connection 340 formed between the respective leading ends 304a and 304b thereof. The releasable connection 340 sets the disc members 312, 314 in their insertion configuration with the predetermined insertion wedge angle ω formed therebetween. In the preferred and illustrated form, the releasable connection 340 cooperates with the dome bearing portion 319 and the recess portion 317 of the respective members 312, 314 to form the insertion wedge angle ω of a particular disc unit 300.

Figure 7:
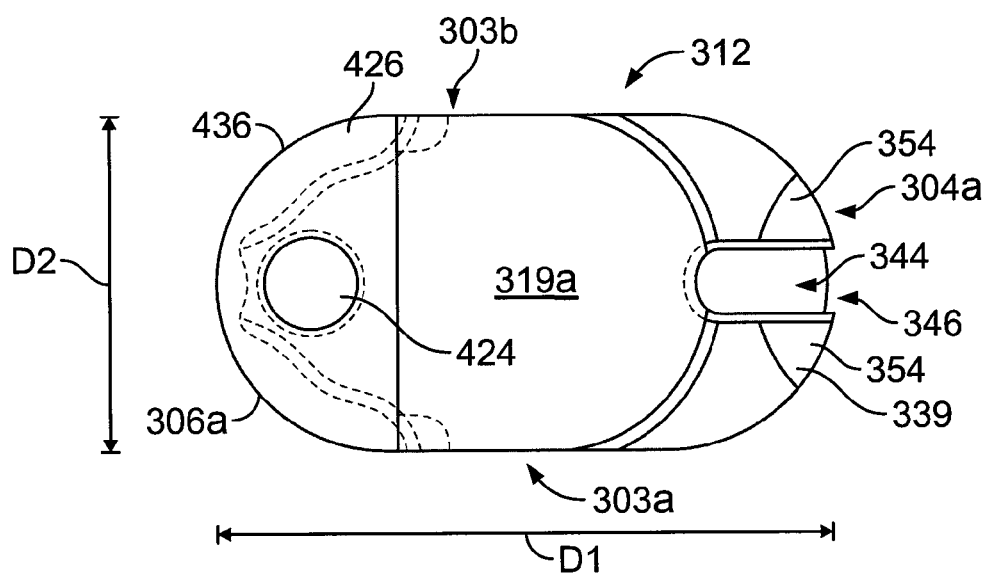
FIG. 7 is a top plan view of the lower member of the artificial disc device of FIGS. 1 and 2 showing a generally racetrack peripheral configuration and a recess at the leading edge of the lower member.
Figure 8:
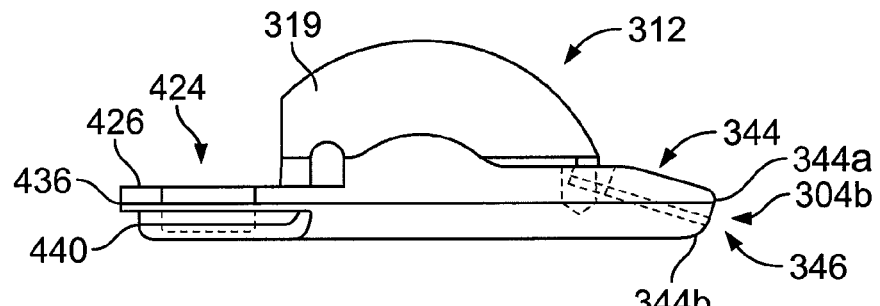
FIG. 8 is a side elevational view of the lower member showing a dome bearing portion thereof.
Figure 9:
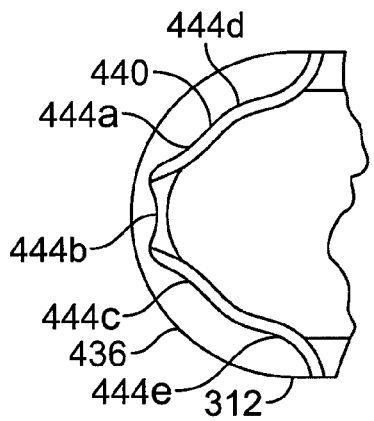
FIG. 9 is a fragmentary bottom plan view of the lower member showing the wall portion and wall for confronting the inserter tool during insertion.

Referring to FIGS. 7 and 8, it can be seen that the lower member 312 includes a recess 344 formed at the end 304a thereof with the recess 344 extending at an incline upwardly in a direction extending from the front end 304a toward the rear end 306a relative to the general plane of the disc member 312. A projection 342 that fits in the recess 344 is provided on the upper member 314, and it is configured to extend in or parallel to the general plane of the member 314. In this manner, with the disc members 312, 314 releasably attached via receipt of the projection 342 in the recess 344, the upper member 314 will be inclined or tilted upwardly relative to the plane of the lower member 312. Also, the bearing portions 317 and 319 cooperate so that the upper member 314 is engaged with and supported by the lower member 312 with the members 312, 314 releasably attached. In particular, rearward of the releasable connection 340 the recess bearing portion 317 of the upper member 314 will rest on the front side of the upper member bearing portion 319, as can be seen in FIG. 1.

The releasable connection 340 is of sufficient strength to keep the disc members 312, 314 attached together as the disc unit 300 is being pushed through the annulus incision 308 and for the initial stage of insertion into the vertebral disc space 311. As discussed, the shells 312, 314 are preferably provided with cooperating structure such as a projection 342 and recess 344 that releasably secures the shells 312, 314 in the desired wedge-angle orientation. In the preferred and illustrated form, the releasable connection 340 is in the form of an interference or snap-fit connection such as a dove-tail joint 340 located at the leading end portions 304a, 304b of the shells 312, 314. In this regard, the top shell 314 includes the projection in the form of a dove-tail projection 342, and the bottom shell 312 includes a mating recess 344 configured to substantially match the configuration of the dove-tail projection 342.

The leading and trailing ends 304a, 304b, 306a, 306b of the upper and lower members 312, 314 are sized so that, when implanted, the nucleus implant 300 provides the desired maximum physiological movement between the implant members 312, 314. The leading ends 304a, 304b may also include abutment surfaces 352, 354 so that the members 312, 314 may contact and abut along surfaces 352, 354 when in the insertion configuration. The members 312, 314 may be oriented so that the surfaces 352, 354 are in flush contact when the projection 342 and recess 344 are secured or snap-fit together. Towards this end, the upper shell member 314 includes a flat surface 352 from which the dove-tail projection 342 extends that abuts the raised flat surfaces 354 on either side of the recess 344 of the bottom member 312. The flat surfaces 354 are inclined upward in a direction from the front, or leading edge, toward the rear of the lower member 312. As illustrated, in one embodiment the top member surface 352 is not inclined, and the wedge-angle ω may correspond to the angle provided between the surfaces 354, 352 by the inclination of the surfaces 354 of the lower member 312. However, the angle of the surfaces 354, 352 may be reversed such that the surface 352 is angled inwardly from respective leading edges 304a, 304b, or the angle of the surfaces 354, 352 may each be angled inwardly, each configuration being such that the surfaces 354, 352 may be in a flush abutting relationship at the wedge-angle with the implant 300 releasably connected in the wedge insertion configuration thereof.

To secure the dove-tail 342 in the recess 344, the shells 312, 314 may be placed together such that the recess 344 is positioned in a confronting relationship to the dove-tail projection 342. The dove-tail projection 342 includes wings 343 angled outwardly from a base 345 of the projection 342 such that the projection 342 has a leading surface 342a with a dimension D3 greater than a dimension D4 at the base 345. The recess 344 is provided with a geometry for receiving the angled wings 343 of the projection 342 such that an upper portion 344a of the recess 344 is smaller in dimension than a lower portion 344b. In this manner, manual pressure may then be applied to the top and bottom surfaces 320, 322 of the shells 312, 314 so that the wings 343 of the dove-tail 342 are forced into the recess 344 and secured there in a snap-fit or interference fit. Alternatively, the dove-tail 342 may be secured in the recess 344 simply by aligning the dove-tail 342 with an opening 346 at the forward end of the recess 344 and sliding the dove-tail projection 342 therein.

At least a portion of the connection 340 is formed of material that is resiliently deformable such that either the projection 342, the surfaces about the recess 344, or both may resiliently deform to permit the projection 342 to be received with the recess 344 in the snap-fit or interference fit. In a preferred embodiment, the dove-tail projection 342 is formed as a relatively small, integral extension of the upper shell 314 via a machining or molding operation such that the projection 342 is also formed of PEEK material. It has been found that the PEEK material possesses sufficient strength and an appropriate degree of rigidity such that the projection 342 may have a reduced size profile while nevertheless functioning properly in the snap-fit connection 340. The recess 344 in the bottom shell 312 is also preferably provided as an integral recess in the flat surface 354 adjacent the recess. The recess 344 can be formed by machining a block of PEEK material, or in a molding operation. The recess 344 should be sized to provide sufficient PEEK material adjacent the recess so that the sidewalls of the recess 344 can firmly hold the dove-tail projection 342 in a snap-fit arrangement until the desired loading is imparted on the implant 300 during insertion. It has been found that the PEEK material of the bottom shell 312 possesses sufficient strength and rigidity such that the lower shell 312 and recess 344 can have a reduced size profile with the dove-tail joint 340 still securing the shells 312, 314 in the desired insertion orientation until the desired release loading is imparted by the vertebral endplates on the implant 300. The resiliently deformable PEEK material permits the connection 340 to be released during insertion due to the force of implantation and constraint of adjacent vertebrae, as will be discussed hereinafter. Surfaces of the projection 342 and recess 344 may be coated with a material that facilitates joining the projection 342 and recess to form the connection, and/or material that resists the separation of the connection 340 during implantation, as will be discussed below. Thus, the above described snap-fit connection may advantageously be provided as an integral structural feature of the implant 300 while avoiding the use of separate components formed of other high strength materials such as metals.

Figure 2:
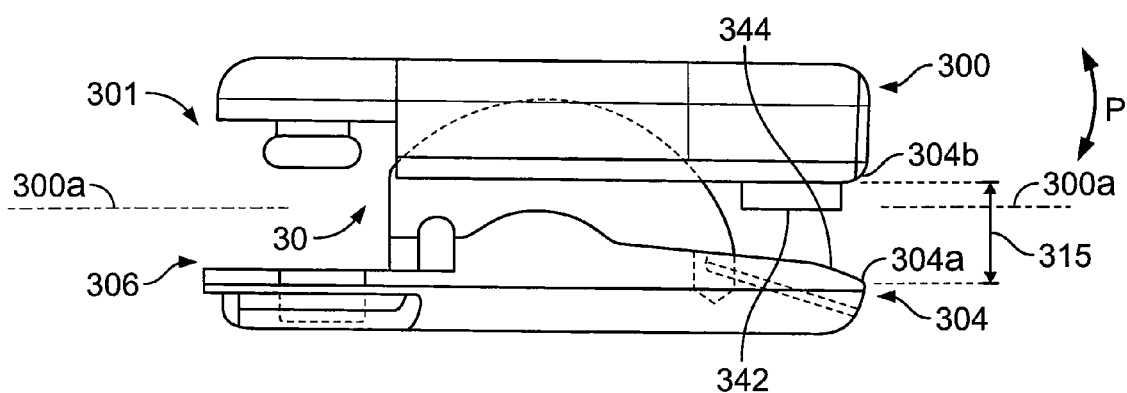
FIG. 2 is a side elevational view similar to FIG. 1 except with the connection between the members released with the members in an operable configuration.
Figure 5:
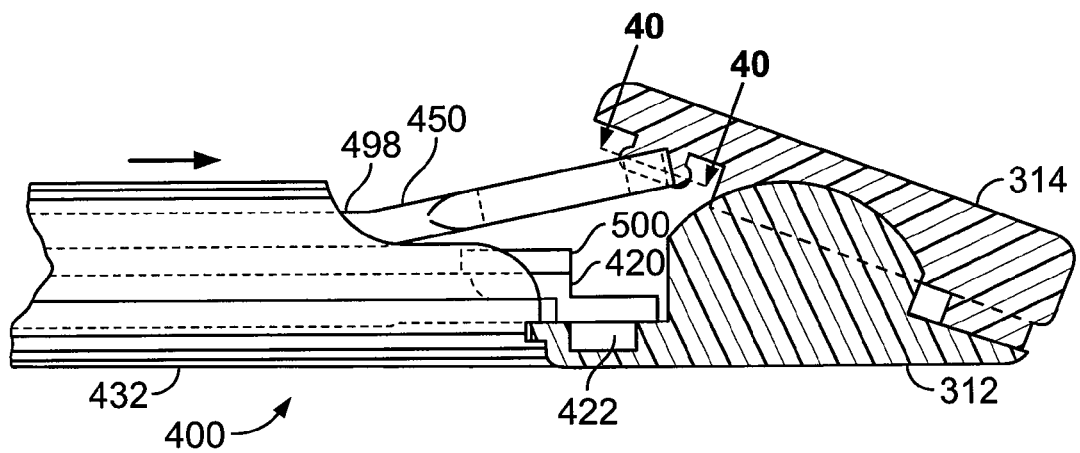
FIG. 5 is a partial cross-sectional view corresponding to FIG. 4 showing the inserter tool secured to the artificial disc device for implantation with the grip member advanced to hold the lower member.
Figure 6:
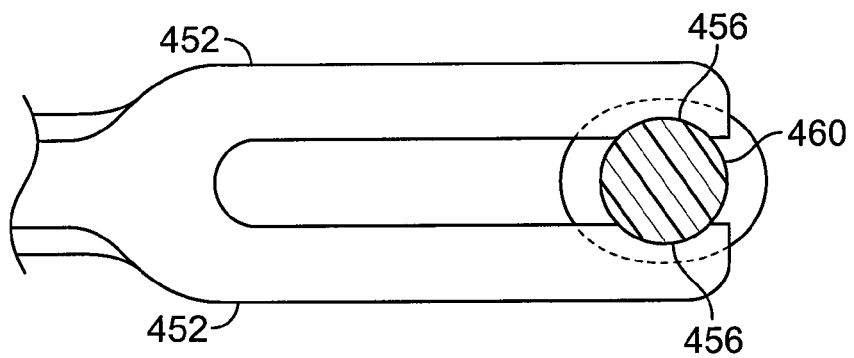
FIG. 6 is a partial cross-sectional view taken through the line 40-40 of FIG. 5 showing a grip post of the upper member secured in a yoke grip.

Accordingly, the interference fit provided between the connecting portions 342 and 344 provides a predetermined level of resistance against pivoting of the disc members 312, 314 relative to each other and, in particular, the upper member 314 at the forward end 304b thereof away from the lower member forward end 304a. On the other hand, with sufficient force applied to members 312, 314, the interference fit of the dove-tail connection 340 is overcome so that the disc members 312, 314 can assume an operable configuration where the members 312, 314 can shift relative to each other, as shown in FIG. 2. To this end, the disc device 300 is selected relative to the size of the vertebral or nuclear space into which it is to be inserted. The vertical distance between the trailing or rearward end portions 306a and 306b of the respective members 312, 314 in their attached insertion configuration should be slightly greater than the distance between the adjacent vertebrae 321, and specifically the end plates 313 thereof between which the disc device 300 is to be inserted.

Thus, as the disc device or unit 300 slides into the space as described further hereafter, the lower and upper trailing ends 306a, 306b will be brought into engagement with the corresponding end plates 313. Accordingly, in the preferred form herein, it is the top and bottom surfaces 322, 320 that serve as engagement portions of the disc body 301 during the implantation procedure. Continued pushing of the disc unit 300 into the vertebral disc space 311 causes the surfaces 322, 320 to engage or cam initially against the annulus, which becomes compressed, and then against the vertebrae and end plates 313 with progressively greater force. With a properly sized disc unit 300 relative to the vertebral disc space 311, this squeezing force at the opposing, spaced apart ends 306a, 306b eventually will become great enough to cause the releasable connection 340 to snap apart so that the members 312, 314 pivot relative to each other about the bearing interface 315 therebetween. With the connection 340 formed at the leading end portion 304 of the disc assembly 300, and the separation force applied on the top and bottom surfaces 322, 320 thereof, there is a lever arm advantage that is utilized to overcome the interference fit at the preferred connection 340 with the intermediate dome bearing portion 319 serving as a fulcrum for this purpose. This allows the strength of the attachment between the members 312, 314 as provided by the connection 340 to be maximized to ensure that the disc unit 300 maintains its connected insertion configuration during insertion until it is inserted into the annulus 309 a sufficient amount. On the other hand, it is also true that this wedge arrangement and utilizing the members as lever arms 312, 314 allows for relatively low force insertion of the disc assembly 300 into the vertebral disc space 311 and to achieve the operable configuration of the disc assembly 300. In addition, the small configuration of the leading end allows the assembly 300 to be easily aligned with the incision for initial insertion. Moreover, the separation force can be applied to the ends 306a and 306b as the disc unit 300 is being turned or rotated, as previously described, toward its fully seated position between the vertebrae in the nuclear space therebetween. In shifting between the insertion configuration and the operable configuration, the members 312, 314 have a pivoting direction, as represented by arrow P in FIGS. 1 and 2.

Figure 19:
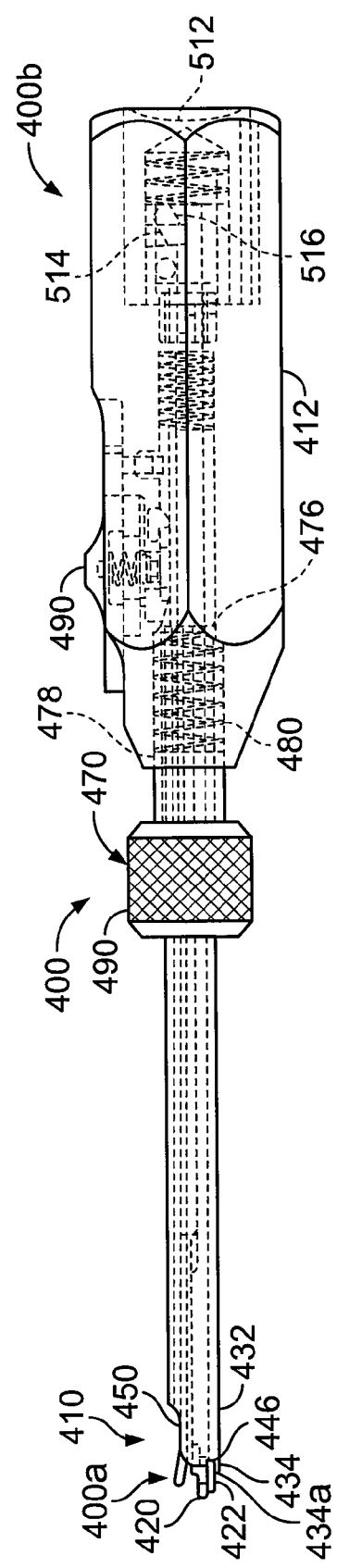
FIG. 19 is a side elevational view of the inserter tool in accordance with the present invention.
Figure 20:
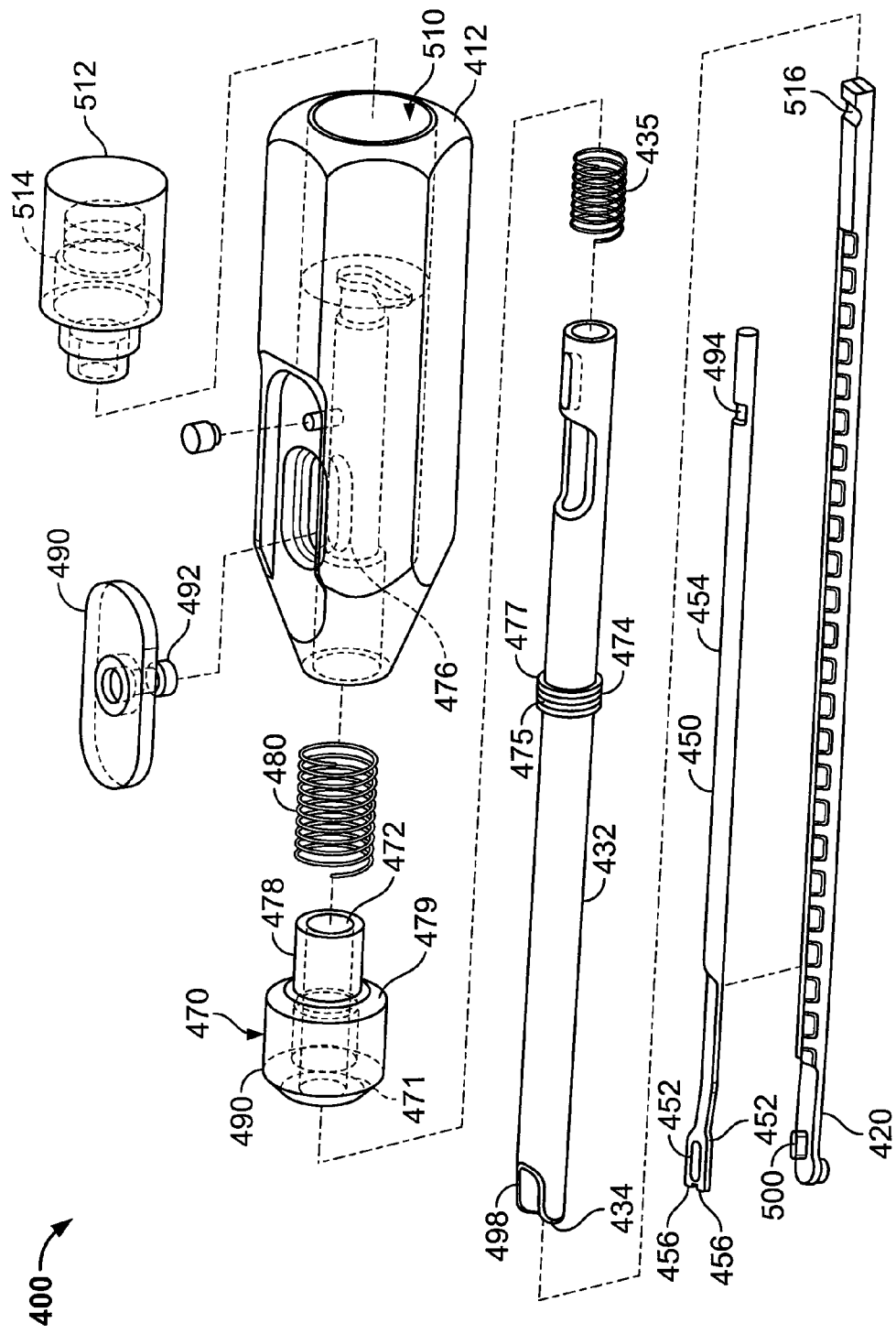
FIG. 20 is an exploded perspective view of the inserter tool of FIG. 19 showing grip members for securing the inserter tool to the artificial disc device.

An inserter instrument 400 for implanting an artificial disc device such as implant 300 is illustrated in FIGS. 19 and 20. The inserter 400 may grip or releasably secure the shells 312, 314 of the implant 300 for insertion and rotation into and within the nuclear cavity 311.

In order to initially grip the shells 312, 314, the inserter 400 is provided with grip members 410 of metallic material for retaining the shells 312, 314 on a distal end 400a of the inserter 400 while a surgeon, for instance, holds a handle 412 on a proximal end 400b. A first grip member in the form of an elongate, rod-like base grip 420 is generally fixed relative to the handle 412 and includes structure in the form of a boss 422 extending from the grip member 420, and the bottom shell 312 has engaging structure in the form of a recess 424 formed in a surface 426 thereof. The recess 424 is formed proximal a trailing end 306a of the bottom shell 312. The surface 426 is generally oriented towards and facing the top shell 314 when the implant 300 is assembled. Therefore, the boss 422 extends in a direction generally away from the top shell 314 when attached to the bottom shell 312.

The inserter 400 is further provided with a second grip member which may selectively reciprocate in a direction parallel with the base grip 420. Specifically, the second grip member is in the form of a metallic cylindrical grip shaft 432 generally surrounding the base grip 420, and the grip shaft 432 is biased towards the distal end 400a of the inserter 400 by, for instance, a spring 435. The grip shaft 432 includes a contoured tip 434 of metallic material for contacting the trailing end 306a of the bottom shell 312.

Figure 10:
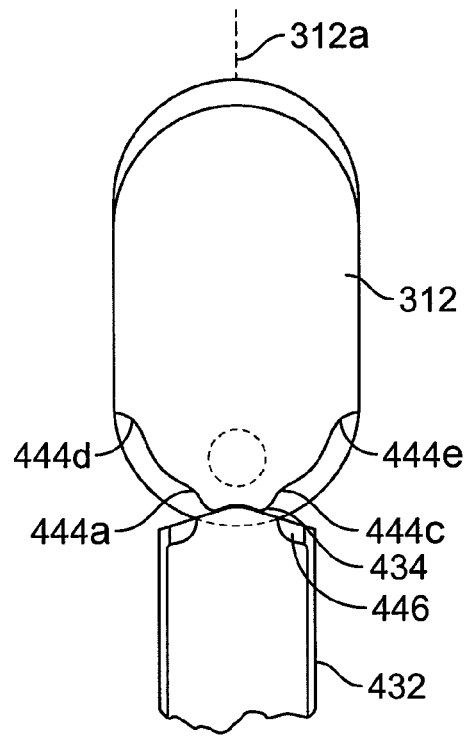
FIG. 10 is a bottom plan view of a grip member of the inserter tool secured to the lower member in the insertion orientation.
Figure 11:
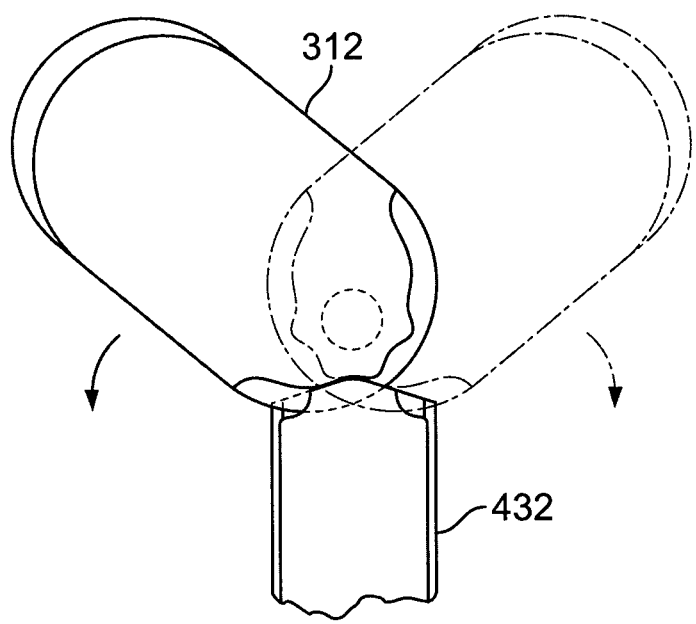
FIG. 11 is a bottom plan view of the grip member and lower member corresponding to FIG. 10 showing the lower member rotated relative to the grip member for positioning the lower member within the annulus.
Figure 12:
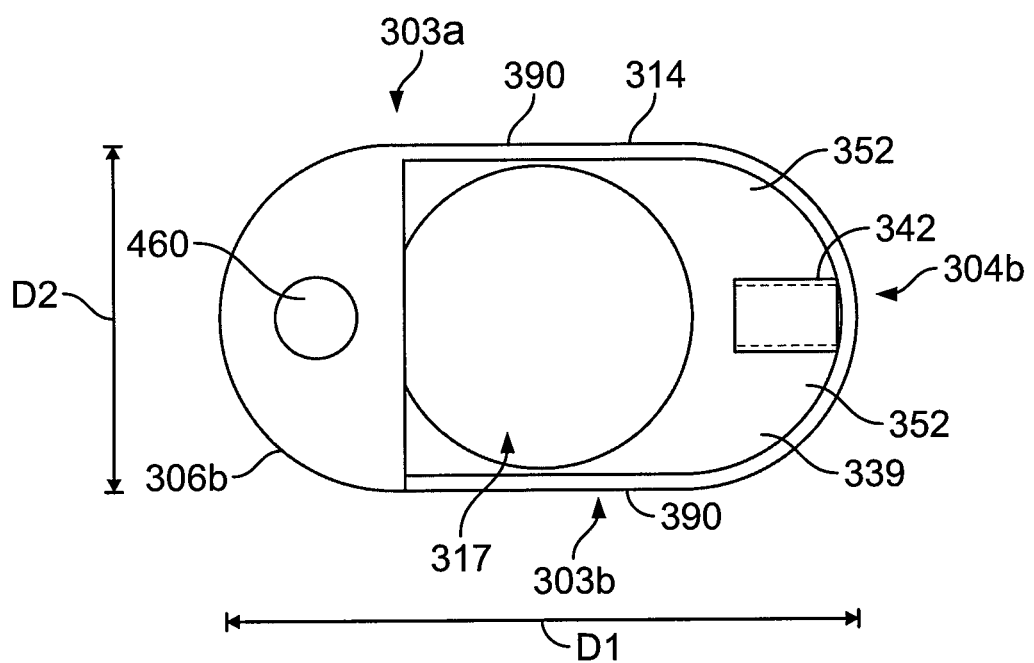
FIG. 12 is a top plan view of the upper member of the artificial disc device of FIGS. 1 and 2 showing a generally racetrack peripheral configuration and a projection at the leading end of the upper member.
Figure 13:
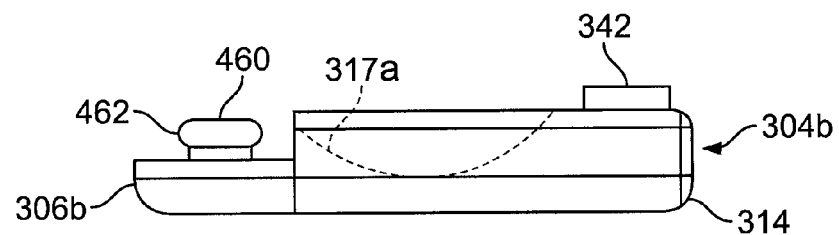
FIG. 13 is a side elevational view of the upper member showing an arcuate recess and a grip post for securing with the inserter tool during implantation.
Figure 14:
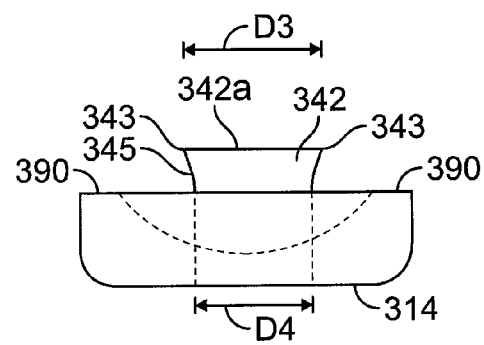
FIG. 14 is a side elevational view of the upper member showing the dove-tail configuration of the projection of the trailing end of the upper member.
Figure 15:
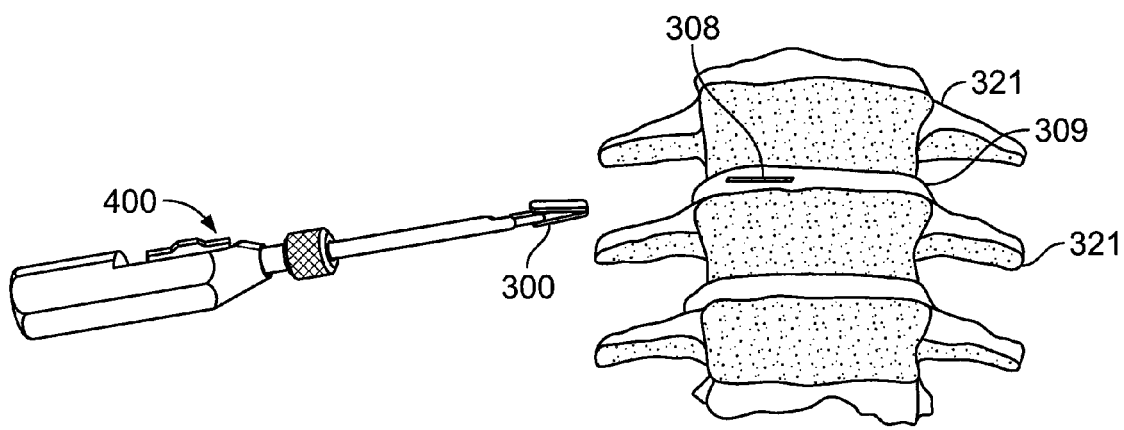
FIG. 15 is a view of the artificial disc device secured to the inserter tool in the insertion configuration and a spinal section including an annulus of a spinal disc having an incision made therein.
Figure 16:
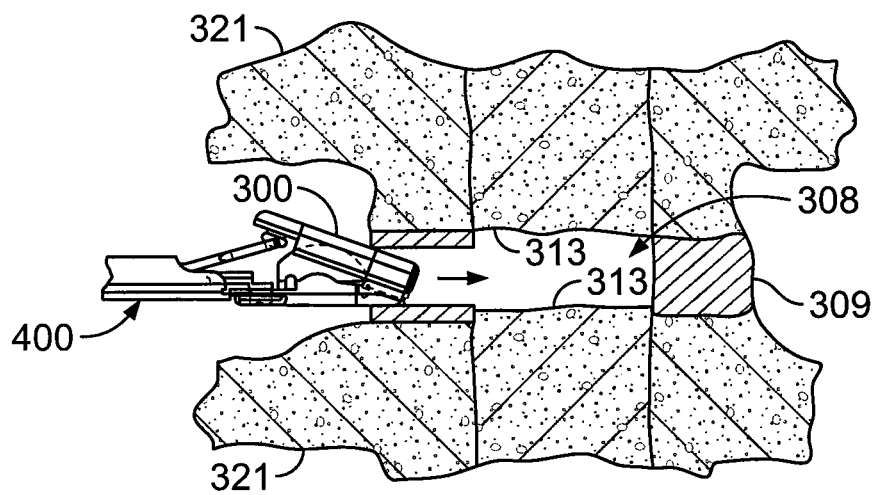
FIG. 16 is a partial cross-sectional view of the spinal section of FIG. 15 showing the artificial disc device in the insertion configuration being inserted through the annulus.
Figure 17:
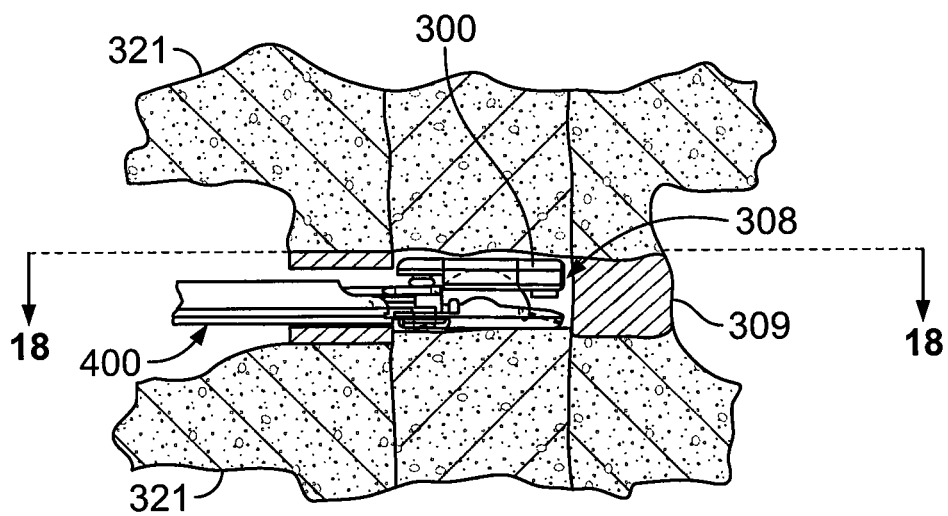
FIG. 17 is a partial cross-sectional view corresponding to FIG. 16 showing the members released and in the operable configuration in the nuclear space.
Figure 18:
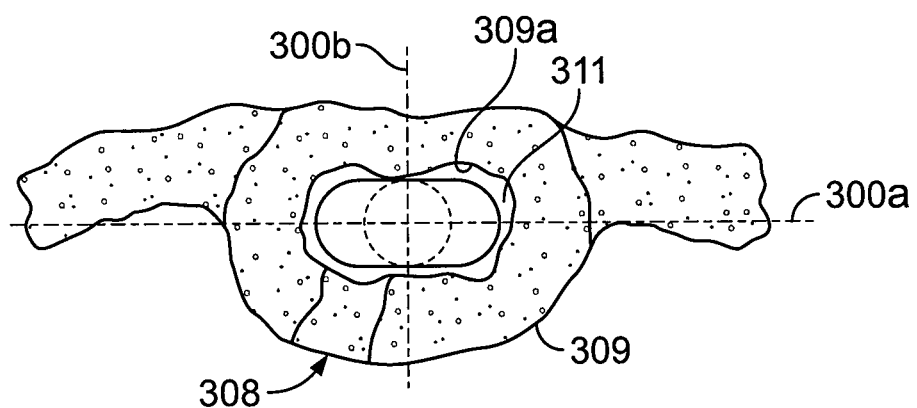
FIG. 18 is a cross-sectional view taken along the line 52-52 of FIG. 17 showing the artificial disc device turned to an implanted orientation from the insertion orientation.

More specifically, the trailing end 306a of the bottom shell 312 includes a lip wall portion 436 projecting rearwardly at the trailing end 306a of the bottom shell 312. The lip portion 436 extends beyond a shoulder 440 therebelow near the trailing end 306a. The shoulder 440 is scalloped to define a continuous surface including sequential, arcuate, concave surface portions 444. A middle arcuate surface 444b is aligned centrally with the longitudinal axis 312a of the shell 312. The grip shaft tip 434 is contoured to include a convex surface 434a that matches the curve of the middle arcuate surface 444b. Accordingly, the shaft tip 434 and the middle arcuate surface 444b mate in a pre-determined orientation, as shown in FIG. 10.

To the sides of the middle arcuate surface 444b are side arcuate surfaces in the form of secondary arcuate surfaces 444a, 444c, which are generally identically curved to each other and are angled outward from the middle arcuate surface 444b, and of tertiary arcuate surfaces 444d, 444e which are also generally identically curved and are angled outward from the secondary arcuate surfaces 444a, 444c. As an example, the total angle between the middle arcuate surface 444b and the left side arcuate surfaces 444a, 444c, or right side arcuate surfaces 444d, 444e may be approximately 90-95°. However, the side arcuate surfaces 444a, 444c, 444d, 444e do not require a precise orientation for engaging the shaft tip 434. In this manner, when the shaft tip 434 is engaged against any side arcuate surface 444a, 444c, 444d, 444e, the bottom shell 312 may shift in its orientation against and along the side surface 444a, 444c, 444d, 444e. The grip shaft 432 further includes a shell recess 446 located above the shaft tip 434 and in between the shaft tip 434 and the base grip 420 positioned within the grip shaft 432. The arcuate surfaces 444 may be machined into the PEEK bottom shell 312 or formed during a molding operation.

The bottom shell 312 is secured to the inserter 400 by the grip shaft 432 and the base grip 420. To do so, the grip shaft 432 is partially retracted against the spring bias so that the shaft tip 434 is moved a distance away from the boss 422. The boss 422 is then inserted into recess 424 of the bottom shell 312, and the wall portion 436 is inserted into the shell recess 446. The grip shaft 432 is then allowed to shift towards the bottom shell 312 such that the shaft tip 434 mates with the middle arcuate surface trial spacer. In this manner, the bottom shell 312 is clamped by the bias force of the grip shaft 432, and its longitudinal axis 312a is aligned with the elongate base grip 420 and grip shaft 432. The dimensions of the bottom shell 312, including the wall portion 436, shoulder 440 and recess 446 are such that the clamping force imparted on the bottom shell by the inserter does not cause significant deformation of the PEEK material bottom shell 312. The wall portion 436, shoulder 440 and vertical sidewall of recess 446 provide strong, rigid surfaces that can withstand sufficient force from the inserter required to insert the implant 300 into the annular space.

In the preferred embodiment, the grip shaft 432 may be mechanically tightened or secured so that accidental retraction against the bias does not occur. In the present embodiment, this is achieved by including a biased-forward securement sleeve 470 having an internal bore 472 such that the securement sleeve 470 is positioned around the grip shaft 432, as well as partially within the handle 412. The grip shaft 432 has a widened portion 474 having external threads 475 forming a shoulder 477, while the securement sleeve 470 has a butt shoulder 478 at its proximal end, a shoulder 479 within its internal bore 472, and threads 471 within the bore 472. A spring 480 is located between the butt shoulder 478 and a shoulder 476 formed in the handle 412, while the shoulders 477, 479 are generally in contact by force of the spring 480. Therefore, retraction of the grip shaft 432 causes its shoulder 477 to press against the shoulder 479 of the securement sleeve 470 so that both retract together.

However, the securement sleeve 470 may retract relative to the grip shaft 432 by compressing the spring 480, as well as may rotate independent of and relative to the grip shaft 432. More specifically, the securement sleeve threads 471 mate with the grip shaft threads 475. In a normal position, the spring 480 biases the securement sleeve threads 471 away from the grip shaft threads 475. When the securement sleeve 470 is retracted against the spring 480, the securement sleeve threads 471 move to a position where they may engage the grip shaft threads 475. The securement sleeve 470 may be rotated by a knurled knob 490 so that the securement sleeve is threaded onto the grip shaft 432. Eventually, the knob 490 comes into contact with the handle 412 such that the securement sleeve 470 is tightened thereagainst, along with the grip shaft 432 threaded into the securement sleeve 470. In this manner, the grip shaft 432 is unable to retract, and the bottom shell 312 is locked between the secured grip shaft 432 and the fixed base grip 420.

The inserter 400 may also secure the top shell 314 for insertion. To do so, the inserter 400 includes a third grip member in the form of a metallic yoke grip 450, and the top shell 314 is provided with a grip post 460 received by the yoke grip 450. The yoke grip 450 includes an elongate shaft 454 also generally positioned within the grip shaft 432, and a pair of yoke arms 452 at a distal end 450a. Each yoke arm 452 includes a cup- or hemispherical-shaped recess 456 on an interior surface such that the cup recesses 456 of the respective yoke arms 452 are generally oriented toward and facing each other.

The grip post 460 of the top shell 314 includes an exterior surface 462 for engaging within the cup recesses 456. To insert the grip post 460 within the yoke arms 452, the yoke arms 452 may flex outwardly slightly. The grip post 460 may also compress slightly. In this manner, the grip post 460 is snap or interference fit within the yoke arms 452 and releasably secured therein. Unlike the securement of the bottom shell 312, which has a rigid orientation with the inserter 400 in the initial position, the top shell 314 is allowed to pivot around its grip post 460 within the yoke arms 452, such as like a ball joint. The grip post 460 is preferably provided as a relatively small, integral projection of top shell 314 formed of the same PEEK material as the shell 314. As such, the grip post 460 may be of a relatively small cross sectional diameter example size while still having sufficient strength to function as a pivot axis for the yoke arms 452 and to withstand the lateral force imparted by the yoke arm 452 when the implant 300 is inserted into the annular space. By providing the grip post 460 as an integral portion of the PEEK upper shell 314, the number of components of the implant 300 are minimized and its overall design simplified.

The shells 312, 314 may be secured to form the dove-tail joint 340 prior to being secured to the inserter 400. Alternatively, the shells 312, 314 may be provided with the insertion orientation after being secured to the inserter 400. For this, as the top shell 314 is pivotable, manual pressure is simply applied to force the dove-tail 342 and recess 344 together. As an additional alternative, the inserter 400 may secure to the top shell 314 such that the top surface 322 is provided with a specific angle, and the shells 312, 314 then are provided with the wedge-angle ω and the insertion configuration.

Once releasably secured to the inserter 400 and in the insertion configuration, the implant 300 is ready to be inserted into and through the annulus 309 and into the nuclear cavity 311. As discussed above, the force of insertion experience by the implant 300 causes the implant 300 to shift from the insertion configuration to the operable configuration. As also noted, the inserter 400 may be used to rotate the implant 300 to orient and align the larger, longitudinal dimension D1 with the incision 308 in the annulus 309. During insertion and rotation, the implant 300 may contact an inner surface 309a of the annulus such that the contact guides the implant 300 into the nuclear cavity 311 and guides the rotation of the implant 300 therewithin. The implant 300 and inserter 400 may be used in a variety of surgical approaches or techniques, including a lateral approach, antero-lateral approach and postero-lateral approach.

Once the implant 300 has shifted to the operable configuration, the top shell 314 is generally not free to move. That is, despite being secured to the inserter 400 by a ball joint type securement in the form of the grip post 460 and yoke arms 452, the top shell 314 is constrained from significant movement by the annulus 309 and vertebral endplates 313, as well as the articulating bearing member 30 formed between the shells 312, 314. Accordingly, the top shell 314 generally follows the bottom shell 312.

The bottom shell 312 remains generally fixed relative to the inserter 400 until the surgeon selects otherwise. When a determination is made that the implant 300 has been advanced within the annulus 309 and nuclear cavity 311 a sufficient amount that the rigidity is no longer necessary, or that the implant is in a position that it needs to be rotated, the grip shaft 432 may permit the bottom shell 312 to shift or pivot around the boss 422 to one of the side arcuate surfaces 444a, 444c, 444d, 444e. The bias of the grip shaft 432 may then shift the grip shaft 432 into an abutting relationship with one of 444a, 444c, 444d, or 444e. Accordingly, the top shell 314 also pivots with the bottom shell 312 around the grip post 460. As the side arcuate surfaces 444a, 444c, 444d, 444e are angled from the middle arcuate surface 444b, the surgeon may direct the implant 300 into the nuclear cavity 311 in a direction transverse to the insertion direction such as in the lateral direction (orthogonal to the anterior-posterior insertion direction, for example) when the shaft tip 434 is secured in one of the side arcuate surfaces 444a, 444c, 444d, 444e.

Once the implant 300 is inserted sufficiently into the incision, the grip shaft 432 may be completely retracted. Because of the pressure and constraint provided by the superior and inferior endplates 313, coupled with the yoke arms 452 and the grip shaft boss 422, the bottom and top shells 312, 314 are still held by the inserter tool 400, though they are able to pivot. In this manner, the surgeon may pivot and manipulate the implant 300 within the nuclear cavity 311, for instance, until a desired position is achieved while the grip shaft 432 is still biased by the spring in a confronting relationship with the surfaces 444.

To withdraw the inserter 400, the implant 300 must be released therefrom. In the preferred embodiment, the yoke grip 450 is selectively reciprocable by a slide 490. To secure the top shell 314 thereto, the yoke grip 450 is advanced relative to the grip shaft 432 by advancing the slide 490 relative to the handle 412. The slide 490 includes a post 492 received within a recess 494 in the yoke grip shaft 454 within the handle 412. To release the implant 300, the top shell 314 is released by retracting the slide 490, thereby retracting the yoke grip 450. As the shell members 312, 314 are mated, such retraction should allow the yoke arms 452 to separate from the top shell 314. Alternatively, such retraction may draw the yoke arms 452 towards and within the cylindrical grip shaft 432 such that a trailing end 306b of the top shell 314 contacts a forward edge 498 of the grip shaft 432. Continued retraction of the yoke grip 450 forces the top shell 314 to be released from the yoke arms 452. As a further alternative, retraction of the yoke grip 450 may force the top shell 314 against a portion, such as post 500, of the base grip 420, thereby causing the top shell 314 to be released from the yoke arms 452. The grip shaft 432 may then be retracted, and the boss 422 may be lifted out of the recess 424.

The proximal end 400b of the handle 412 includes an opening 510 in which a release 512 is secured and spring-biased in the proximal direction. When the bias is overcome and the release 512 is pushed into the handle 412, a pin 514 is shifted from a secure position to a release position. In the secure position, the pin 514 is received in a recess 516 and secures the base grip 420 in a generally fixed position. In the release position, with the pin 514 shifted out of the recess 516, the base grip 420 may be removed, as well as the yoke grip 450 and the slide 490. In this manner, the inserter 400 may be disassembled for cleaning and sterilization post-procedure.

FIGS. 21-27 show upper and lower implant members 500 and 502, respectively, for an alternative intervertebral implant. The articulating implant members 500 and 502 are similar to the previously described articulating implant members 312 and 314 with the main difference residing in the provision of symmetrical features on the implant members 500 and 502 so that an insertion tool can operatively engage the members 500 and 502 at either of the ends thereof. The other difference of note is that the implant members 500 and 502 do not have a releasable connection therebetween that holds the implant members 500 and 502 in a wedge configuration for insertion. Rather, an insertion tool can be utilized for this purpose as described in application Ser. No. 60/822,027, incorporated by reference as if reproduced in its entirety herein.

The implant member 500 has a dome bearing portion 504 including convex bearing surface 505 thereof. At either longitudinal end of the implant member 500, respective recesses 506 are provided in end plate portions 508 thereof. The recesses 506 open upwardly for receiving a small, mating boss at the end of an insertion tool. As can be seen in FIG. 24, the recesses 506 create an underlying thin wall portion 510 at the ends of each of the end plate portions 508.

Additionally, similar to the previously described implant member 312, an arcuate engagement surface 512 is formed at the end of the end plate portion 508 adjacent the recess 506. The arcuate recess 512 is indented inwardly toward the dome bearing portion 504, as best seen in FIG. 23. As such, the surface 512 also is on a thin wall portion 514 at the end of the end plate portion 508 extending upwardly from the wall portion 510, as can be seen in FIG. 22. In addition, a thin wall lip projection 516 projects outwardly from the end plate portion 508 above the arcuate surface 512. In each instance, the implant member 500 including the various thin wall portions 510, 514, and 516 thereof benefit from being of a PEEK material like the bearing surface 505. More particularly, with the wall portions 510 and 514 that operatively engage with metallic insertion tool components, the enhanced strength thereof is such that these PEEK wall portions 510 and 514 typically will not fail during implant insertion.

In addition, the dome bearing portion 514 has an undercut recess 518 toward the bottom thereof, as shown in FIG. 24. A metallic disc of the insertion tool fits into the recess 518 for insertion of the implant member 500 into the intervertebral space 500. In this instance, the PEEK material bearing portion 504 still is able to provide the high wear resistance and strength in a manner similar to the previously-described implant 300 including implant member 312 thereof despite having a portion thereof removed for the undercut recess 518. Also, the dome bearing portion 319 of implant member 312 is truncated at one end; and, in a similar manner, the dome bearing portion 504 is truncated but at both ends thereof.

Figure 25:
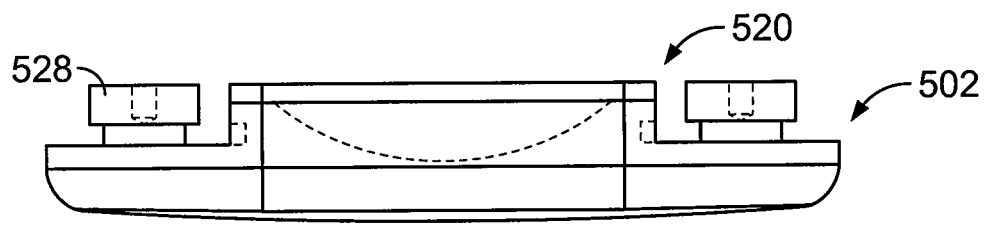
FIG. 25 is a side elevational view of an upper, articulating member of the alternative intervertebral implant device showing symmetrically oriented posts at either end for cooperating with an insertion tool.

FIGS. 24-26 show the upper articulating implant member 502 including recessed bearing portion 520 having a raised square-shape configuration from end plate portions 522 on either side thereof. The bearing portion 520 has a concave surface 524 preferably having the same curvature as the convex surface 505 of the dome bearing portion 504 so that the surfaces 505 and 524 form a smooth bearing interface therebetween for articulation of the implant members 500 and 502. With the concave surface 524 formed in the square-shaped recess portion 520, an annular thin wall portion 526 is formed in the recessed bearing portion 520 with the concave surface 524 formed thereon. Even with the thin wall portion 526 supporting the loads during articulation of the implant members 500 and 502, it is anticipated that having the implant members 500 and 502, and particularly the bearing surfaces 505 and 525 thereof, be of a PEEK-type material, desirable strength or wear properties will be imparted thereto sufficient for their use as a motion preservation intervertebral implant device, as described herein. It is believed that it is the strength and wear resistance of the PEEK material as identified for the implants described herein that allows for the bearing portions to be formed with thin wall portions or have sections removed without compromising the performance thereof.

In addition, the end plate portions 522 include narrow post projections 528 that cooperate with the insertion tool for advancing the implant member 502 into the intervertebral space along with the implant member 500 bearing thereagainst. In this regard, it is anticipated that the strength of the PEEK-type material used for forming the implant member 502 will provide beneficial strength characteristics to the small post projections 528 when experiencing the forces applied thereto by the insertion tool during implant insertion.

Wear tests were performed to assess the clinical viability of providing the articulating bearing surfaces of weight bearing orthopedic joint arthroplasty devices in the form of surfaces made of PEEK material. These evaluations were performed of a two-piece articulating nucleus replacement implant substantially similar to the embodiment of FIG. 1-18 described above. The wear testing was performed using intervertebral disc simulators, with test regimes including reciprocating motion, multidirectional motion and multidirectional motion profiles with frequency shifting. Dynamic compressive loads representing the range of physiological loadings believed to be supported by nucleus supporting were utilized in all testing methodologies. Details of this testing and the test results are described in more detail below.

Test A: Flexion/Extension

A sample size of six artificial nucleus implants made of PEEK in general accordance with the embodiments of FIGS. 1-18 were tested in a multi-specimen spine simulator. The bottom component of the implant was retained in a specimen cup, and the top component was retained in a specimen post. These specimen fixtures were manufactured from UHMWPE obtained from McMaster-Carr. The modulus of the UHMWPE was approximately 0.70 GPa, which is within the typical range of the modulus of the cancellous bone of vertebral endplates of about 0.10-0.80 GPa. The method for mounting the components in the test chambers did not compromise the accuracy of the assessment of specimen mass loss. The superior sample was constrained in three-dimensional space. The inferior sample was allowed to rotate in the direction of testing only, without translations. The recesses in the fixtures for receiving the implant components matched the footprint of the implant, but allowed for slight micro motion of the implant components to simulate that which could potentially occur in vivo.

Testing fluid that approximates the physiological environment was retained in the specimen cup. The testing fluid consisted of 55 g/L protein content, triple 0.1 μm filtered, sterile newborn calf serum (Hyclone Labs) diluted with phosphate buffered saline to a final protein content of 20 g/L. EDTA (Fisher Labs) was added to the serum at a concentration of 20 mM to bind the calcium ions present in the serum and to act as a preservative. The final test fluid was filtered through a 0.22 μm filter. The test fluid temperature was kept at 37±3° C. The pH of the testing fluid ranged from 7.4 to 8.56 during testing. The testing environment was considered physiological and in general conformed with the existing literature. Each specimen fixture was isolated to prevent cross-contamination of the test specimens. To prevent excessive evaporation of the testing fluid, plastic bags were used to seal the fixturing. The specimens were pre-soaked in the test fluid until an asymptotic point in the moisture uptake curve was observed.

The geometry and surface finish of the opposed dome and recessed articulating surfaces of the two-piece nucleus device used in this study are set forth in the following table.

TABLE 1

Surface finish and geometry of specimen bearing surfaces

|  | Radius (in) | Sphericity | Surface Finish (Ra) |
| --- | --- | --- | --- |
| Top Shell | 0.2575 ± 0.0004 | 0.0006 ± 0.0001 | 9.08 ± 1.30 μin |
| Bottom Shell | 0.2496 ± 0.0001 | 0.0004 ± 0.0001 | 23.00 ± 3.34 μin |

The samples were sterilized using gamma radiation with a minimum dose of 29.3 kGy and a maximum dose of 37.3 kGy.

A flexion/extension profile of ±7.5° with cyclic compressive loads of 225-1024 N up to 10 million cycles was used. Peak compression occurred at peak rotation with a cyclic compressive load frequency of 4 Hz and a rotational frequency of 2 Hz. In this manner, two cycles of compression are applied with one cycle of flexion/extension rotation. A full cycle of rotation means that the disc implant rotates from full flexion to full extension then back to full flexion. During this full cycle of rotation the compressive load changes from peak load at full flexion to minimal load at zero rotation then to peak load again at full extension. In this half cycle of flexion/extension rotation, the disc implant completes one full cycle of compressive loading. The flexion/extension profile of ±7.5° represents a sagittal motion close to the representative physiological extreme. The cyclic compressive load of 225-1024 N represents the range of loading the implant is expected to undergo in vivo based on the nucleus supporting one-half to two-thirds of the compressive load during walking. A frequency of 2 Hz approximates a brisk walking rate. It should be noted that clinical retrievals of disc arthroplasty devices provide evidence that simulator testing of these devices may be 5-10 times too severe, and therefore the loading and kinetic parameters discussed above may go beyond those that the device would normally be exposed to in vivo.

The test was stopped at every 500,000 cycles and all components cleaned and the specimens weighed. The test fluid was also changed at this time. A mass loss assessment was carried out in general agreement with ASTM F 2025-00. The humidity and the temperature were monitored throughout the mass loss measurements, with no perceived changes that would affect the mass loss assessment. A non-loaded soak control was also used in the current study to take into account weight changes caused by any fluid absorption by the PEEK specimens. Such weight changes were found to be negligible.

The results of the test showed an average total mass loss of 2.79±0.14 mg at 10.35 million cycles. The corresponding average wear rate was 0.28±0.07 mg/million cycles. This corresponds to an average total mass loss of 2.13±0.11 mm$^3$ at 10.35 million cycles and an average wear rate of 0.21±0.05 mm$^3$/million cycles. The wear rate was relatively constant throughout the test, although slightly greater during a wear in period up to about 4 million cycles.

The wear rate and mass loss compares well or is superior to other published values in the literature of disc arthroplasty systems. It is also much lower than conventional hip (3 Mrads of gamma radiation) wear rates and comparable to the current cross-linked (5-10 Mrads gamma radiation) UHMWPE in vivo and in vitro hip wear rates using 28 mm head sizes. The wear rate is also superior to conventional UHMWPE in vitro knee wear rates.

The results of the light microscopy of the bearing surfaces of the test specimens showed that the wear pattern was in the direction of articulation. During the early periods of articulation, a macroscopic abrasive wear mechanism occurred. This macro adhesive wear mechanism generally is confined to the wear-in period where any machining marks on the components are worn away. This was confined mainly to the anterior-posterior bearing regions of both upper and lower implant shells, and consisted of plowing and micro cutting of the articulating surfaces. The lateral portions of the concave and convex articulating surface features underwent a brief macroscopic abrasive wear period, followed by a microscopic abrasive wear period. This microscopic wear mode was analogous to polishing of the articulating surface.

After the initial wear in period, no perceived changes in the wear mechanism were observed. For example, a comparison of wear pattern of the concave articulating surface of the top component of one representative specimen at 2.6 M cycles and 10.3 M cycles, respectively, revealed no notable change in the wear mechanism occurring. A comparison of the wear pattern of the convex articulating surface of the bottom component of the same sample at 2.6M cycles and 10.3 M cycles also showed no notable change in the wear mechanism.

Test B: Lateral Bending

Figure 48:
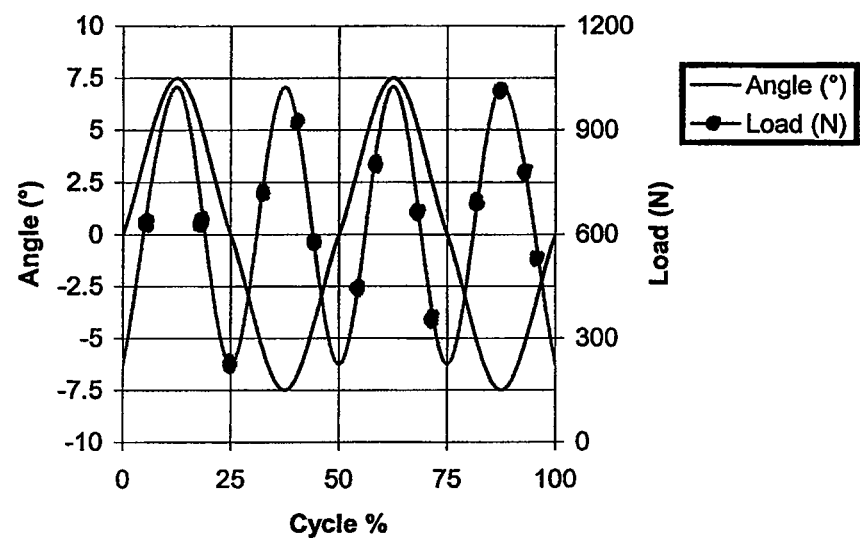
FIG. 48 is a graph of the kinematic and loading profile for lateral bending simulation of an artificial nucleus implant.

To allow for a more comprehensive assessment of their wear and mechanical durability, after an initial 10.35 million cycles of flexion-extension wear, the devices of Test A were shifted laterally 90° in the simulator chambers to simulate a lateral bending profile for an additional 10.12 million cycles. The test regime consisted of lateral bending over a of ±7.5° range of motion at dynamic axial compression of 225-1024 N at a compression frequency of 4 Hz and a rotation frequency of 2 Hz. The kinematic and loading profile is depicted in FIG. 48.

Six specimens were tested to 6.1 million cycles of lateral bending. Two specimens were lost at this point due to a machine malfunction. Therefore, four specimens were tested to 10.12 million cycles of lateral bending. A non-loaded soak control was also used in the current study to take into account any fluid absorption by the test specimens.

The results of the lateral bending test showed an initial wear in period up to 0.63 million cycles, with an associated wear rate of 0.90±0.41 mg/million cycles. After this wear in period, the wear rate adjusted to 0.27±0.09 mg/million cycles up to 6.11 million cycles. This corresponded to a total average mass loss of 1.03±0.28 mm$^3$ at 6.11 million cycles and an average wear rate of 0.21±0.07 mm$^3$/million cycles. At 6.11 million cycles, the six specimens showed an average mass loss of 1.98±0.36 mg. For the four remaining specimens, the average total mass loss was 0.96±0.22 mg from 6.11 million cycles to 10.12 million cycles. The average wear rate was 0.25±0.11 mg/million cycles. This corresponded to an average mass loss of 0.74±0.17 mm$^3$ and an average wear rate of 0.19±0.09 mm$^3$/million cycles. The total mass loss was 5.54 mg or 4.29 mm$^3$ at 20.47 million cycles for both the flexion/extension and lateral bending tests.

The results of this study indicate that the wear rate of the artificial nucleus device is insensitive to the change in direction of articulation, as evidenced by the near consistent wear rate of Test A and Test B. The wear rates still compare well or are superior to other known published values in the literature for weight bearing joint arthroplasty systems.

Light microscopy of the samples demonstrated that the same abrasive wear mechanism occurred, but in the direction of articulation and perpendicular to the previous wear pattern caused by the initial flexion/extension profile conducted in the Test A. The predominant mechanism in the early stages of articulation appeared to be macroscopic plowing mode. This was especially noted on the central aspects # of the articulating surfaces of the top and bottom components. The lateral portions of the articulating surface features had already undergone a microscopic abrasive wear mode (polishing) during the previous flexion/extension test, and were not subject to the macroscopic plowing mode as seen on the central aspects of the top and bottom articulating surfaces. The initial wear pattern caused by the initial test gradually was worn away, resulting in the surface becoming more polished. In all, as the test progressed, the surfaces developed a more burnished appearance. Throughout the test duration, no perceived change in the wear mechanism occurred.

This further testing demonstrated that the PEEK bearing surfaces of the disclosed nucleus device are insensitive to independent biaxial motion and provide a wear rate that compares well, or is superior to, other disc, hip and knee arthroplasty devices that have published wear simulator data and/or published clinical use data. Full device functionality was maintained with no gross deformation, delaminations or cracks.

Test C: Multidirectional Coupled Motion with Constant Frequency

Multidirectional testing of the nucleus implant described in the embodiment of FIGS. 1-18 was conducted according to the ISO standard 18192-1 for wear testing of total disc replacements. This consisted of all the physiological motions of flexion/extension, lateral bending and axial rotation coupled together at the same frequency.

A sample size of six nucleus replacement implants were evaluated. The samples were similar to those evaluated in Tests A and B, and were representative of those that would be applicable to a clinical setting. Two sets of six nucleus replacements were pre-soaked in the test lubricant for approximately 28 weeks. The second set of six was used as a weight control for the testing to compensate for moisture uptake. The weight of the test specimens was shown to be largely unaffected by moisture uptake.

The samples were evaluated using a six-station spine wear simulator (EndoLab GmbH, Rosenheim, Germany). This apparatus applies three rotations, flexion-extension rotation, lateral bending and internal-external rotation, as well as vertical loading to each station and sample. The rotational degrees-of-freedom (DOF) were mechanically linked; each axis was driven through a lever arm by an individual hydraulic actuator. Identical vertical loading was applied to each station by hydraulically coupling the actuators. Each DOF was closed-loop controlled.

The specimen fixtures used to hold the implant components within each simulator chamber were identical to those used in Tests A and B. Each chamber of the simulator contained 100 ml testing lubricant. The test lubricant consisted of the same phosphate buffered saline and EDTA mixed with bovine serum to a final protein content of 20 g/l. The temperature of the chambers was controlled at 37±1° C. The testing environment was considered physiological.

Figure 49:
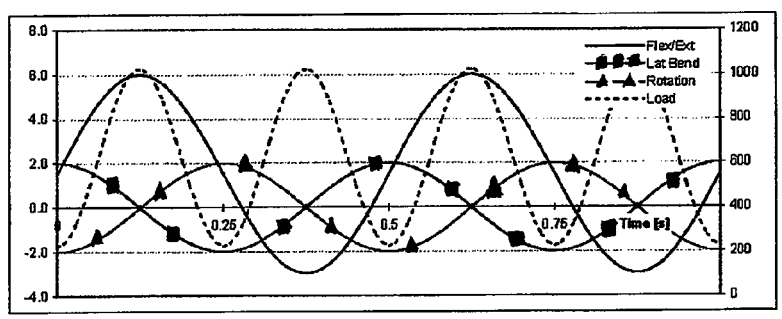
FIG. 49 is a graph of input parameters for multidirectional testing of a nucleus implant.

The test parameters consisted of +6/−3° of flexion/extension, and ±2° of lateral bending and axial rotation. Lateral bending was 90° out of phase with flexion/extension and axial rotation was 180° out of phase with lateral bending. Peak compression occurred at peak flexion/extension. The rotational frequency was conducted at 2 Hz. A dynamic compressive load of 225-1024 N was used. The vertical load profile magnitude was altered from ISO 18192-1 to consider the load sharing characteristics between the artificial nucleus and the annulus fibrosis in-vivo. The input parameters are summarized in Table 2 and further depicted in FIG. 49.

TABLE 2

Test C Kinematic and Loading Profile

| Kinematic Profile | Profile | Frequency |
| --- | --- | --- |
| Flexion/Extension | ISO 18192-1 | 2 Hz |
| Lateral Bending | ISO 18192-1 | 2 Hz |
| Int./Ext. Rotation | ISO 18192-1 | 2 Hz |
| Vertical Compression | Sine (225N . . . 1024N) | 4 Hz |

At every 500,000 cycles, the test was stopped and all components cleaned and the specimens weighed. The test fluid was also changed at this time. The test was then re-started for the next 500 k cycles. The overall test ran for 10 million cycles. Wear-in behavior was observed on all specimens up to about 1.0 million cycles. Subsequently, all components developed constant wear generation. The wear rate of both superior plus inferior components was 0.51±0.04 mg/million cycles in average. The unloaded soak samples experienced no trend in weight change over the 10.0 million cycles, which shows that the weight of the loaded samples was not affected by uptake of the test lubricant.

Photographic surface examinations revealed polishing as the main wear pattern. Before testing, the manufacturing related machining marks were clearly visible. After the first 500 k cycles, these marks were partly polished away, and from 2.5 million cycles on the surface was entirely polished in the contact area. Furthermore, instances of elliptical scratches were observed, indicating trapped particles that imprinted the motion pattern onto the surface.

The results of this test showed that the wear rate was approximately the summation of the wear rates for the two principle motions of flexion/extension and lateral bending as measured in Tests A and B. Together with the similar wear rates measured in Test A and Test B, this suggests that the increase in the wear rate for this test is more of a function of the travel distance rather than an effect of coupled multidirectional motion. The measured wear rate for coupled multidirectional motion in this test was still similar or favorable to other disc arthroplasty devices that had undergone wear testing under similar or less rigorous conditions.

Test D: Multidirectional Coupled Motion with Frequency Shifting

Figure 50:
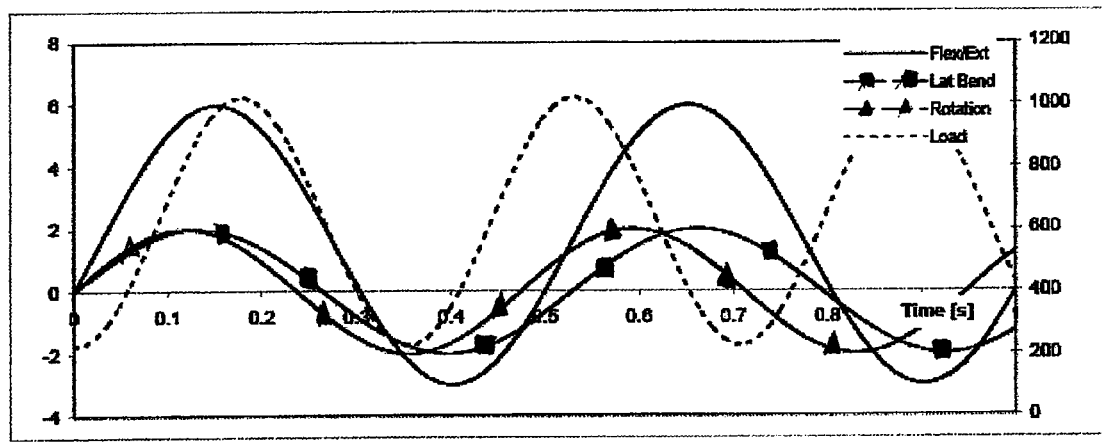
FIG. 50 is a graph of input parameters for multidirectional testing of a nucleus implant with a non-repetitive load path.

A further simulation evaluation was performed using the protocol of Test C, but with non-matching frequencies for each degree-of-freedom. The sample size was six specimens of the same nucleus implant evaluated in Tests A-C. Unlike the periodic sinusoidal motions and load specified in ISO 18192-1 and used in Test C, this next test comprised a different frequency for every degree-of-freedom and thus a non-repetitive load vector path. Thus, the input curves to the controller each had different frequencies. In general, unmatching frequencies assure that no repetitive motion pattern is applied. The load vector moves over the entire contact area and the input profile thus serves as a worst-case situation with respect to cross-shear motion. The vertical load profile magnitude was also altered from ISO 18192-1 to consider the load sharing characteristics between the artificial nucleus and the annulus fibrosis in-vivo. The input parameters are summarized in Table 3 and further depicted in FIG. 50.

TABLE 3

Test D Kinematic and Loading Profile

| Kinematic Profile | Profile | Frequency |
| --- | --- | --- |
| Flexion/Extension | ISO 18192-1 | 2.00 Hz |
| Lateral Bending | ISO 18192-1 | 1.90 Hz |
| Int./Ext. Rotation | ISO 18192-1 | 2.11 Hz |
| Vertical Compression | Sine (225N . . . 1024N) | 2.84 Hz |

The test protocol was identical to that of Test C with the exception of the input profiles. The study did not include loaded or un-loaded soak control specimens because Test C demonstrated that the gravimetric amount of fluid uptake is negligible compared to the weight loss due to wear. The specimens were subjected to 10 million cycles of flexion-extension motion. This resulted in approximately 14.2 million cycles of dynamic compressive loading due to the higher frequency.

Wear-in behavior was observed on all specimens up to about 1.0 million cycles. Subsequently, all components developed a constant wear rate of 0.59±0.01 mg/million cycles in average for both, the superior plus inferior components, corresponding to a wear rate of 0.45±0.01 mm$^3$/million cycles. Photographic surface examinations revealed polishing as the main wear pattern. This wear rate is approximately double that of the non-coupled motion observed in Tests A and B, and is slightly greater than that for the coupled motion with matched frequencies of Test C. The wear rate was still similar to those reported for other low wear material combinations such as metal on metal from tests of less extreme loadings and kinematics. The wear rate was still generally more than an order of magnitude lower than conventional UHMWPE on metal total disc replacement devices. In wear testing including cross-shearing motion similar to the tests described herein, implants having bearing surfaces of CoCr alloy on UHMWPE had reported wear rates of 17.46±1.0 mm$^3$/million cycles and 20.37±1.22 mm$^3$/million cycles, or 39 and 45 times higher than the implant 300 herein having PEEK-on-PEEK bearing surfaces 317a and 319a. Whereas the implant 300 herein has shown to be substantially insensitive to cross-shear action in terms of its wear rate, the CoCr alloy and UHMWPE bearing couples reported 351 and 1033-fold increases in their respective wear rates when evaluated under curvilinear or unidirectional motion profiles or those with limited cross-shear against a test regime that employs frequency shifted cross-shear motion profiles similar to Test D described above.

Test E: Axial Static Compressive Strength and Axial Dynamic Fatigue Evaluation

Six specimens of a nucleus replacement implant made in accordance with the embodiments of FIGS. 1-16 were also tested for axial static and dynamic fatigue strength characteristics. The height of the specimens with upper and lower components assembled was 8.0 mm as measured between respective outer surfaces 320 and 322 with the implant 300 in the neutral position, as shown in FIG. 2. The specimens tested were representative of the smallest true contact stress area for all current designs.

A sample size of six specimens were tested for axial static and dynamic fatigue characteristics. The samples used in this test were sterilized using gamma radiation with a minimum dose of 29.3 kGy and a maximum dose of 37.3 kGy. The articulating surfaces were visually inspected prior to the test using light microscopy to verify surface integrity. The test equipment to perform the tests consisted of a MTS Servo Hydraulic System #1 with a 15 kN axial load cell. The implants were attached to each MTS Servo Hydraulic System using two 150-291 1-14 UNS Adaptors.

Data collection software (MTS 793 Operating System V3.4B TestWorks 4 SH V4.08A) was used to collect the Load (N), Displacement (mm), Extension at Peak Load (mm), Peak Load (N), Stiffness (N/mm), Offset Yield Load (2%) for the static tests. The specimens were placed in the center of their respective fixtures, and were subjected to an axial load causing displacement at ramp rate off 2.0 mm/min until breaking or permanent deformation. The tests were conducted in ambient conditions.

The results showed that the axial static load at offset yield ranged from 10102 N to 11099 N, with a mean value of 10427 N. The mean displacement at offset yield was 0.627 mm. The peak axial compressive load ranged from 13978 N to 14026 N with a mean peak load of 14001 N. These results are summarized in the following table.

TABLE 4

Axial Static Compressive Load To Failure

| Specimen # | Peak Load (N) | Load At Offset Yield (N) | Slope (N/mm) | Displacement At Offset Yield (mm) | Offset Yield Displacement (mm) | Displacement at Peak (mm) |
|---|---|---|---|---|---|---|
| 1 | 13978.314 | 11099.191 | 27473.5 | 0.656 | 0.160 | 1.777 |
| 2 | 14020.613 | 10248.458 | 26666.2 | 0.631 | 0.160 | 2.104 |
| 3 | 13985.671 | 10637.817 | 27293.3 | 0.619 | 0.160 | 1.866 |
| 4 | 14006.015 | 10302.007 | 26558.2 | 0.621 | 0.160 | 2.051 |
| 5 | 13991.389 | 10102.161 | 26178.2 | 0.621 | 0.160 | 2.117 |
| 6 | 14026.424 | 10169.789 | 26616.9 | 0.615 | 0.160 | 2.039 |
| Mean | 14001.404 | 10426.570 | 26797.7 | 0.627 | 0.160 | 1.992 |
| Std. Dev. | 19.479 | 378.275 | 488.6 | 0.015 | 0.000 | 0.139 |
| Maximum | 14026.424 | 11099.191 | 27473.5 | 0.656 | 0.160 | 2.117 |
| Minimum | 13978.314 | 10102.161 | 26178.2 | 0.615 | 0.160 | 1.777 |

The test equipment for the dynamic fatigue tests consisted of a MTS Servo Hydraulic System #1 or #2 with a 15 kN axial load cell. Six additional specimens were tested in axial dynamic fatigue mode. The fatigue load was applied at a frequency of 10 Hz with a sine waveform. The same software was used to collect the Load (N), Displacement (mm) and Cycles for the dynamic fatigue tests.

Two specimens achieved 10 million cycles at a peak compressive load of 8342 N without failure. Two other specimens achieved 10 million cycles at a peak compressive load of 9384 N without failure. These loadings represented 80% and 90% of the mean offset yield compressive load, respectively. The final two specimens were tested at 10427 N, which represents the average axial compressive load at offset yield determined in the static compressive load tests. One specimen achieved 10 million cycles without failure. The other failed immediately as a result of excessive plastic deformation of the top shell 314 at the thin wall portion 317 including the concave bearing surface 317*a* thereof. Additional tests using a 9.0 mm height specimen which includes a corresponding thickening of thin wall portion 317, performed at alternating frequencies of 1 Hz and 10 Hz, demonstrated that fatigue performance was not significantly affected by the load frequency or the thickness of the thin wall portion 317. Thus, the results are equally applicable to physiological load frequencies in the range of about 1 Hz. All of these were conducted in ambient conditions.

It has been reported that compression fractures of the human vertebrae can occur from cyclic loads of up to 3995 N in as little as 200 cycles to a maximum of 1.25 million cycles, and that the fatigue strength of the vertebrae can range from ~600 N to ~950 N when normalized to age and disc degeneration, respectively. The results of these axial static compressive test show that the above-described nucleus implant 300, comprising PEEK material forming upper and lower shells 314 and 312 having thin outer endplate portions and a central dome bearing portion 319 for mating with a thin walled convex bearing portion 317, can withstand static loads well beyond the static failure strength of the human vertebral body or endplate. The results of the dynamic axial fatigue test shows that the device also has excellent dynamic fatigue strength for use as a nucleus replacement. There was no specimen failure at 80% (8342 N) and 90% (9384 N) of the average static offset yield load of 10,427 N. In dynamic testing at the 10,427 N average static offset yield load, one of two specimens withstood 10 million cycles without failure. This loading is well beyond the expected physiological loads the device would be subjected to. It also greatly exceeds the dynamic fatigue strength performance requirements commonly accepted for vertebral body replacement (VBR) devices or fusion cages, which is 5 million cycles at a compressive load of 3,000 N. Therefore, the device may advantageously be formed of PEEK material without risk of failure in either static axial compression or dynamic axial compression in vivo.

Thus, evaluations of the mechanical strength and wear properties of an artificial nucleus device in accordance of the embodiment of FIG. 1-18 demonstrate the viability of all polymer PEEK on PEEK material articulating weight bearing joint replacements. A reciprocating wear test of 10 million cycles of flexion/extension followed by 10 million cycles of lateral bending showed a relatively low wear rate that was virtually constant in a two piece articulating nucleus implant formed of PEEK. Coupled multidirectional testing revealed a relatively small increase in the wear rate, which can be deduced to be due to the increase in travel distance versus that of reciprocating motion. Multidirectional wear testing with frequency shifting results in an approximately constant wear in period, and a relatively small increase in the wear rate over the prior constant frequency multidirectional wear testing.

The studies reported herein also demonstrate the viability of various other articulating orthopedic weight bearing devices having primary structural components and bearing surfaces formed of PEEK material. As discussed above, metal on metal bearing couples have been shown to provide exceptionally good wear resistance and mechanical strength in both vertebral disc arthroplasty and other weight bearing joint applications such as hip and knee replacements. These favorable strength and wear properties have led to continued usage of metallic components in such devices despite other drawbacks such as stress shielding, potential metal ion toxicity, and obstruction of tissue imaging associated with metals. Unexpectedly, it has now been found that the PEEK-on-PEEK nucleus implants described herein are extremely durable with wear rates similar to those of metal on metal devices used for nucleus and total disc replacement when tested under relatively extreme conditions. The wear rates also compare favorably to those of other accepted disc couplings such as UHMWPE on metal in weight bearing applications. It has also been found that bearing surfaces formed of PEEK material undergo minimal strain hardening under physiological coupled motion, a phenomenon that has proved detrimental to UHMWPE and ultimately has led to the use of other material combinations and the need for further processing as by cross-linking. The performance of the PEEK on PEEK nucleus replacement disclosed herein, relative to other known bearing couples for disc arthroplasty such as metal on metal and polymer on metal, also demonstrates the viability of this bearing couple for other articulating orthopedic weight bearing arthroplasty devices where these alternative couplings have also been utilized.

Many of the benefits described in the above paragraphs also apply to replacement of weight bearing joints such as the hip, knee, ankle or facet joint.

An artificial knee joint typically comprises a femoral component, a plastic articular component, and a metal base plate. The tibial plateau under the knee joint is replaced with the metal base plate, to which the plastic articular component is attached. A femoral component, usually made of metal, covers or replaces the femoral condyles at the distal end of the femur, and engage the plastic articular component, which is configured to pivotably receive the femoral component.

An improved artificial knee joint may comprise a PEEK material femoral component which articulates directly on a PEEK material articular surface wherein the PEEK material articular surface is separate from the baseplate or the components are integrated into a PEEK component serving as both the articular surface and the baseplate. Similarly, the femoral implant portion may be constructed of PEEK material or simply of an outer PEEK material layer. For example, the femoral implant may be constructed of a biocompatible metal such as a titanium alloy or stainless steel with a layer of PEEK formed over the metallic portion facing the opposing PEEK surface. In this case, the metallic portion preferably includes an osteoconductive surface such as a titanium spray or other coating such as hydroxyapatite to help secure the implant to the bone. Alternatively, the entire metal portion of the femoral implant may be encased in PEEK. The articulating surface is machined for smooth low wear movement, whereas the bone facing surfaces are prepared for adhering to the bone with an osteoconductive surface. An artificial knee cap (patella) may also be provided and comprised of PEEK material, so that three articulating components (femoral cup, tibial member, patella) all have PEEK material articulating surfaces.

Figure 28:
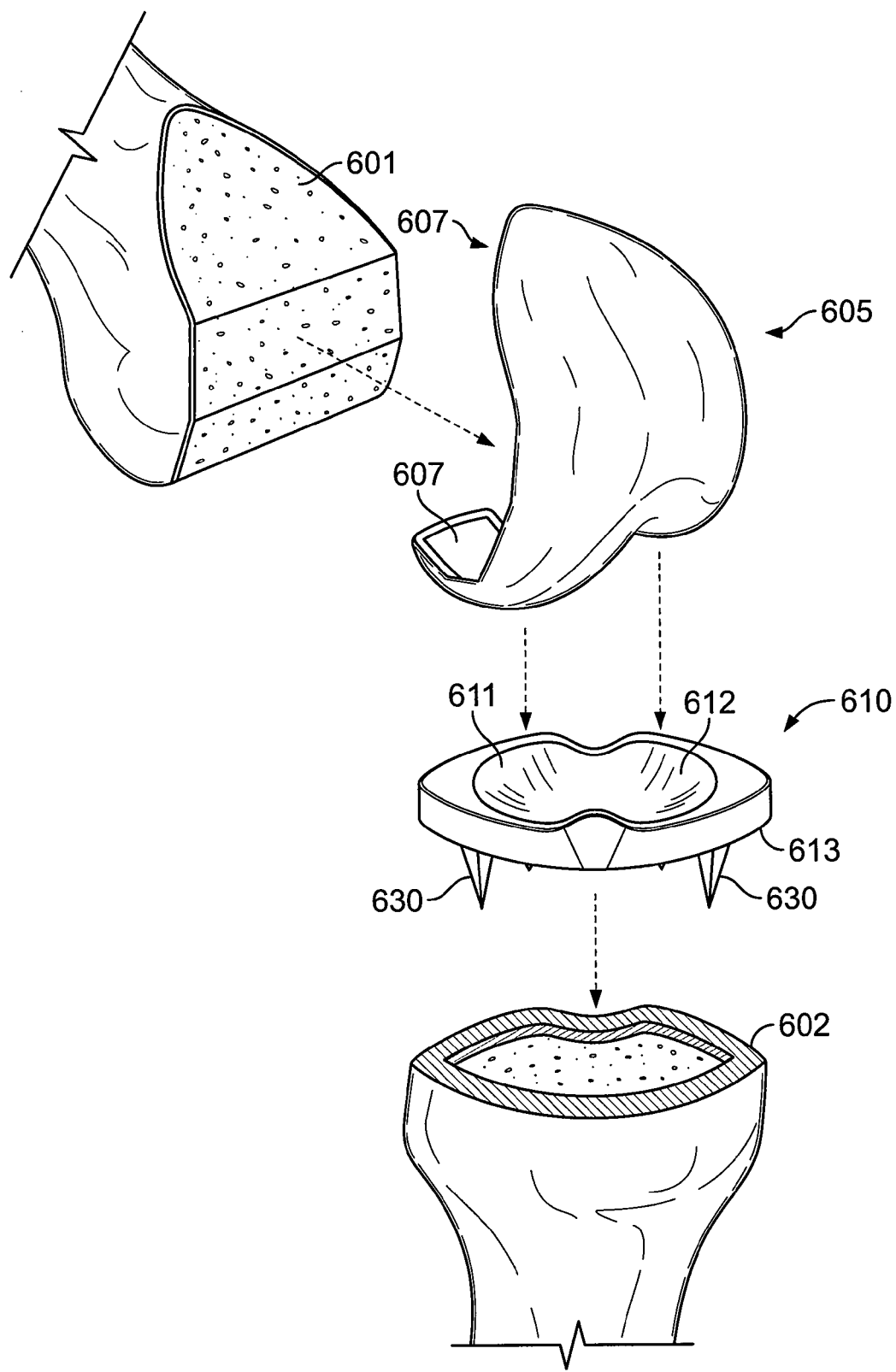
FIG. 28 is an exploded view of a knee prosthesis with a one-piece tibial tray.

An example of an improved knee arthroplasty implant is shown in FIG. 28 comprising a femoral end cap 605 comprised of PEEK material and a tibial plate member 610 comprised of PEEK material, which may be the same or a different type of PEEK material as that used to form the femoral end cap 605. In order to prepare the femur to receive the end cap prosthesis, the femoral condyles are shaved off, filed, or cut into and sufficient bone is removed to configure the distal end of the femur for engagement with the PEEK material femoral end cap. The femoral end cap may be equipped with surface protrusions extending from an engagement surface 607 of the cap 605 in order to mount the cap to the distal end of the femur 601. For instance, spikes, elongate keels, teeth, or ridges may be provided on the engagement surface, either formed integral with the end cap or mounted thereto, to grip the prepared surface of the femur. The end cap may also include openings or throughbores to receive fixation devices such as pins or screws that may be used to secure the femoral cap to the femur. In addition, or in the alternative, a biocompatible cement or adhesive may be used to mount the femoral cap to the prepared surface of the femur. Osteoconductive porous coatings may further be added to assist in integrating the end cap to the femur over time.

Figure 30:
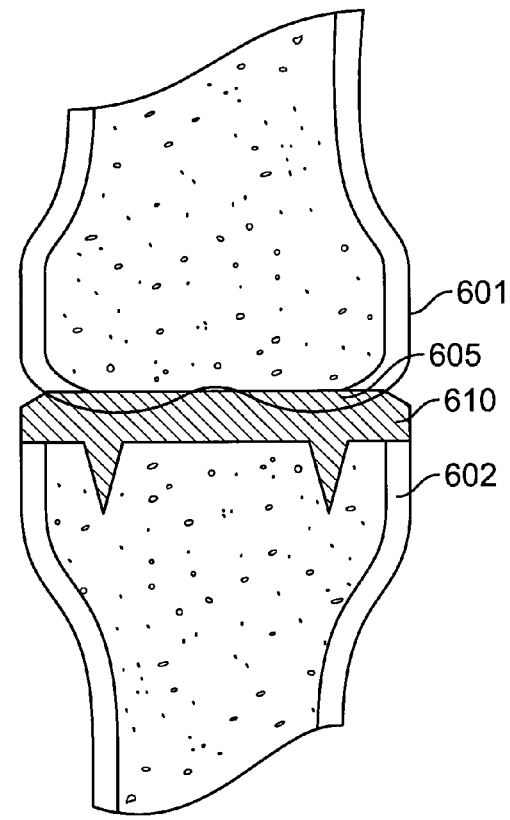
FIG. 30 is a cross sectional view of the knee prosthesis in FIG. 28.
Figure 32:
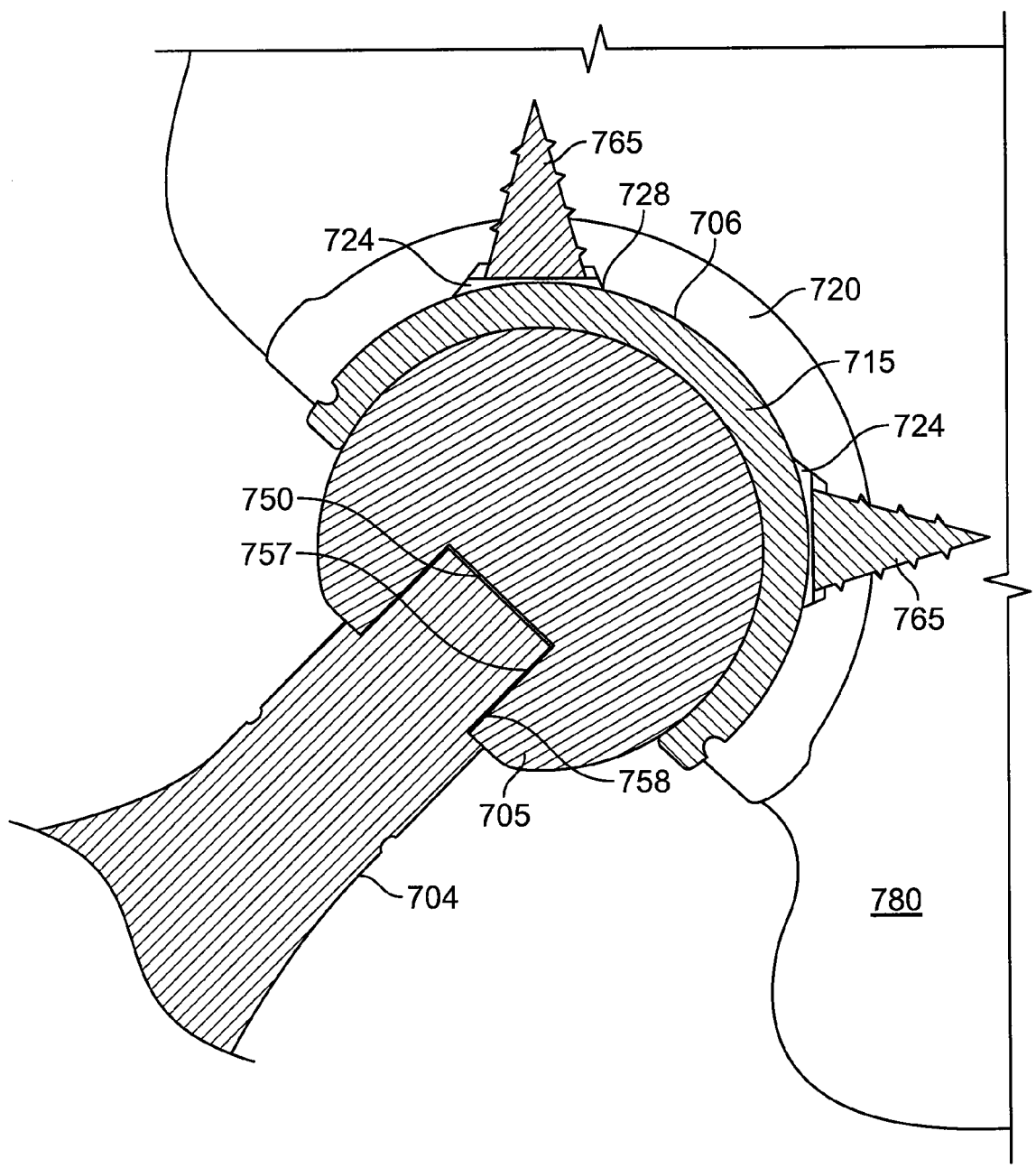
FIG. 32 is a cross sectional view of a hip prosthesis.

FIG. 28 further illustrates a one-piece tibial plate 610 comprised of PEEK material. An upper articulation surface of the tibial plate member is configured to pivotably receive the condyles of the femoral endcap, as best illustrated in FIG. 30. To this end, the superior surface of the artificial tibial plate contains two adjacent depressions 611 and 612 forming a seat for the femoral end cap 605. The inferior surface 613 of the tibial plate has anchor elements 630 extending therefrom to secure the plate to the proximal end of the tibia 602, which may be shaved or filed so that the plate member sits flush on the proximal end of the tibia. The anchor elements 630 may be formed integral with the plate or attached thereto, and may comprise one or more spikes, teeth, threads, elongate keels or fins, screw-like projections, and/or other surface features that assist in securing the plate to the tibial bone. In the alternative, the plate may be secured to the tibia 602 by screws mounted to the bone through openings in the tibial plate member, by plates mounted to both the tibial plate member and the tibia by screws or pins, or any other known method of fixation. In addition, cements, adhesives, and biological agents may be used to assist in securing the tibial plate member to the adjacent bone, and osteoconductive porous coatings may be applied to the inferior surface of the plate member to fuse the plate member to the bone.

Figure 29:
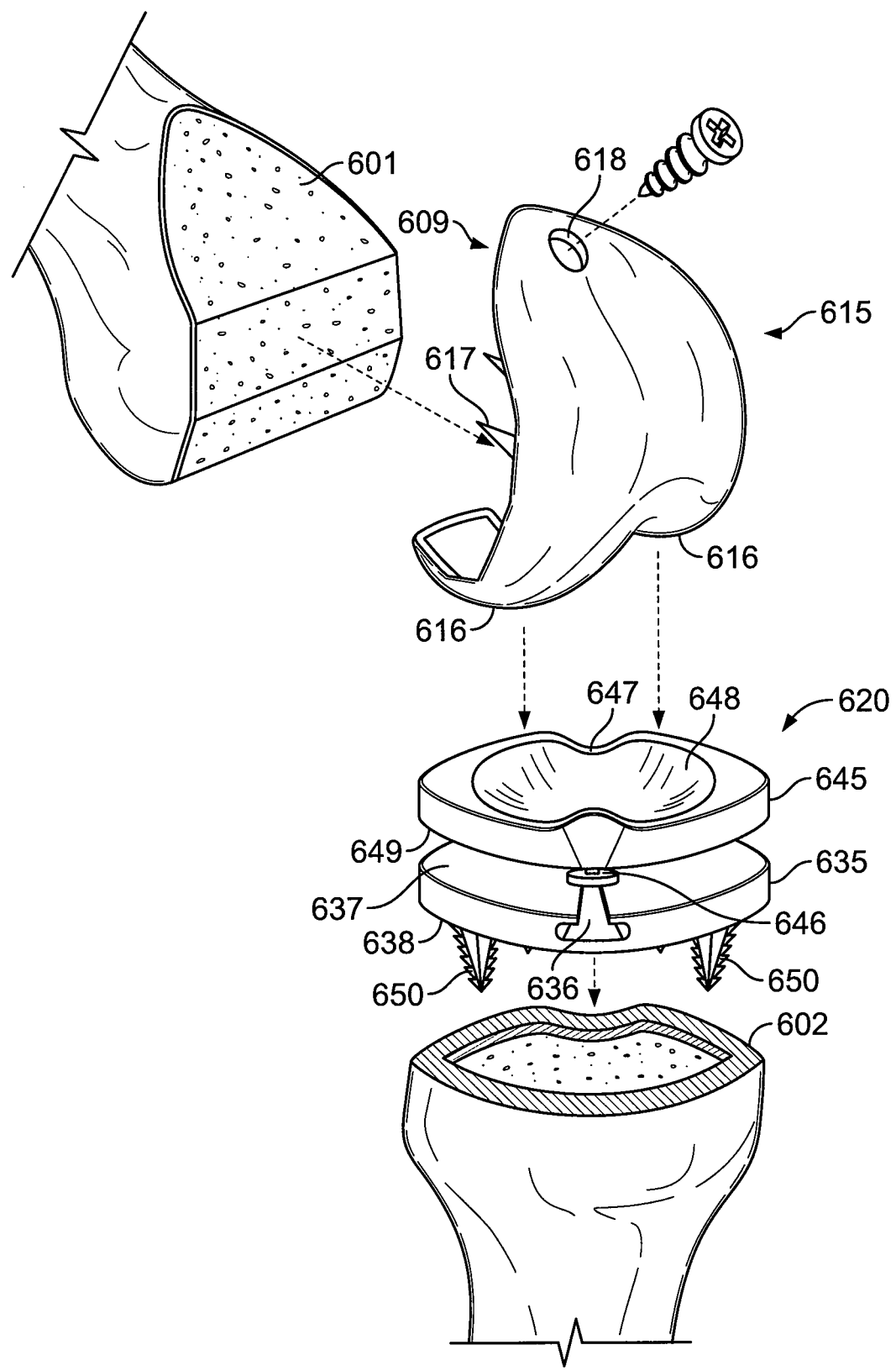
FIG. 29 is an exploded view of a knee prosthesis with a two-piece tibial tray.
Figure 31:
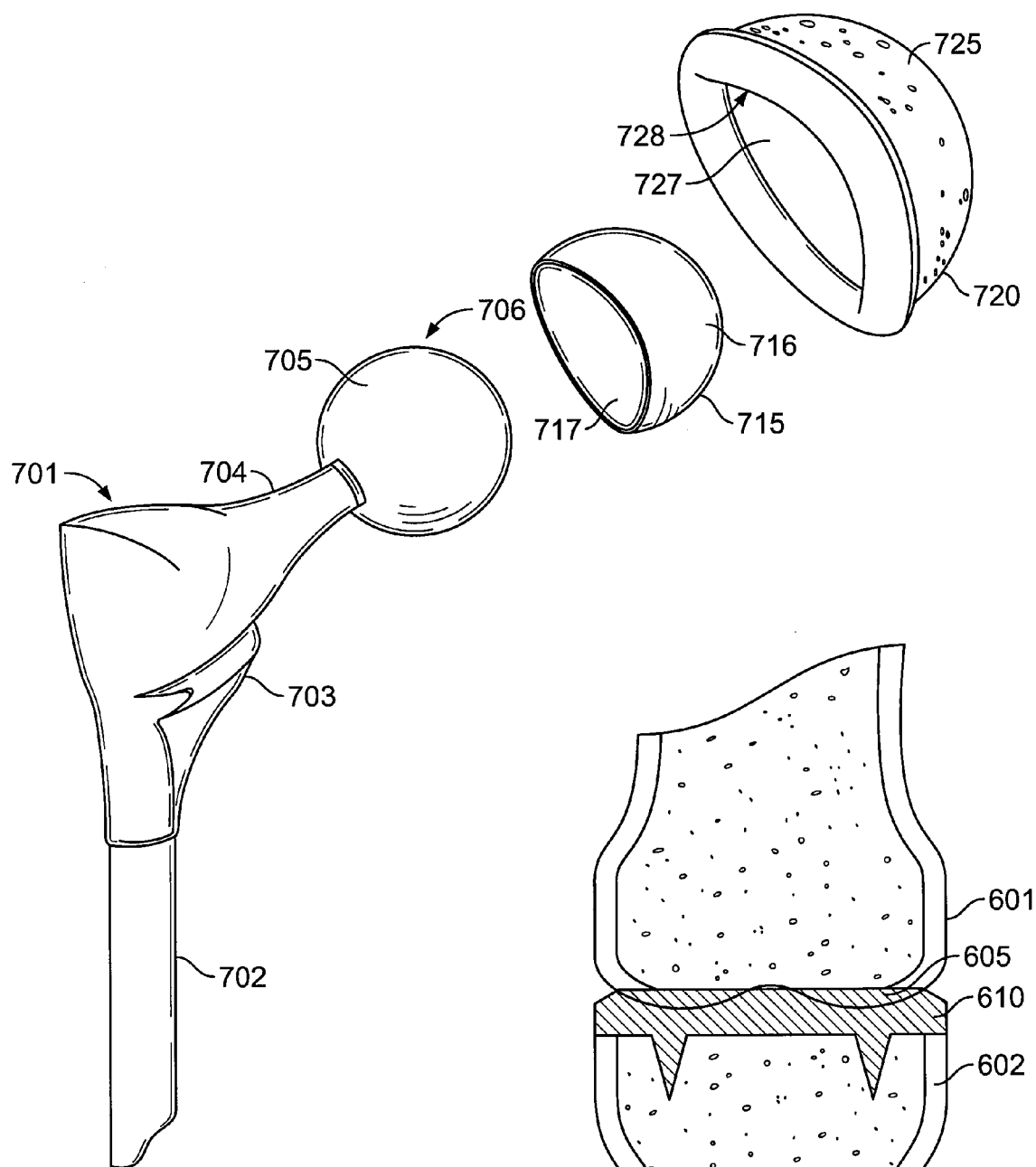
FIG. 31 is an exploded view of a hip prosthesis.

Another form of knee arthroplasty is illustrated in FIG. 29, which in many respects is similar to the implant system shown in FIG. 31. Therefore, only differences between the two implants will be described in detail. The form of implant shown in FIG. 29 comprises a femoral end cap 615 made from a PEEK material and a two-part tibial plate 620. The femoral end cap 615 illustrated contains spikes 617 for engaging the bone of the femur 601, as well as an opening 618 for receiving a screw to be mounted to the femur. The spikes 617 may be formed as integral portions of the femoral end cap 615, or may be separately formed and fixed to the engagement surface 619. The screw may be formed of PEEK material or a biocompatible metal.

The lower portion 635 of the tibial plate 620 may be comprised of a biocompatible metal or a PEEK material, and the upper portion 645 of the tibial plate is an articulation member comprised of a PEEK material for articulation against the PEEK material of the femoral end cap. An upper articulation surface 647 of the plate upper portion 645 forms a seat 648 with two adjacent depressions for pivotably receiving the condyles 616 of the femoral endcap 615. The inferior surface 649 of the plate upper portion 645 contains an elongate flange 646 depending therefrom for engaging the lower plate portion 645.

The plate lower portion 635 may be formed of PEEK material or a biocompatible metal. The superior surface 637 of the lower plate portion 635 contains a slot 636 or track for receiving the flange 646 of the upper plate portion 645 to secure the two portions to one another. The slot 636 may be provided with a hard stop or closed end that abuts the flange of the upper plate portion when the upper and lower plate portions are aligned. Detents may be provided on the flange and/or slot in order to secure the flange within the slot and thereby maintain the upper and lower plate portions in a mating relationship. The inferior surface 638 of the plate lower portion has fixation members 650 protruding therefrom in the form of serrated or barbed spikes, which may be inserted into the bone with relative ease but that will resist removal. It will be recognized that other methods of fixing the plate members to the tibial bone may also be used. In addition coatings may be applied to the spikes to promote bone growth and/or fusion between the lower plate member and the tibia.

Again, the components of the artificial knee may be comprised entirely of PEEK or other ether keytone family polymer. Alternatively, the tibial articular surface and/or femoral cap may be PEEK or another ether keytone polymer mounted, adhered, or otherwise mated with a baseplate of a biocompatible metal. The metal baseplate portion may be partially or entirely encased in PEEK or other ether ketones from this family.

In another form, an improved hip arthroplasty implant having PEEK on PEEK articulation surfaces may be provided. A typical artificial hip joint comprises a stem, a femoral head, a polyethylene liner, and an acetabular shell. An improved artificial hip joint may comprise at least a PEEK material femoral head and PEEK material liner.

Such a basic hip prosthesis is shown in FIG. 31 comprising a stem 701, a ball member forming an artificial femoral head 705, a cup-shaped liner 715 for receiving the ball member, and an acetabular shell 720 for receiving the liner.

The acetabular shell 720 is anchored in the pelvic bone to provide a socket in which the femoral head may articulate. In order to secure the acetabular shell to the pelvic bone, the exterior 725 of the shell 720 may be fitted with one or more fixation means, such as spikes; teeth; threads; keels; pores; screw-like projections; means for receiving fixation devices, such as throughbores for receiving screws or pins; and/or other surface features that assist in holding the shell in place in the pelvic bone. Other means for fixing the shell 720 to bone may also be used, either alone or in combination with the aforementioned means, such as osteoconductive porous coatings of hydroxyapatite (HA), tricalciumphosphate (TCP), and other chemical agents that promote bone growth and/or provide porous surfaces that allow bone ingrowth and osteointegration; cement agents; various biological agents; and combinations thereof. The shell 720 contains a recess 727 that is larger than the femoral head 705 and preferably forms a concave, partially spherical cavity. The acetabular shell 720 may be formed of a biocompatible metal or a PEEK material, and should be of sufficient strength for bearing loads between the femur and pelvis.

The liner 715 is a cup-shaped component that has an exterior surface 716 complementary to the interior cavity 727 of the acetabular shell 720, as well as an interior cavity 717 complementary to the femoral head 705. The liner 715 is sized and configured to cover the interior surface of the concave recess in the acetabular shell 720 in order to provide an articulation surface for the femoral head 705. In order to properly bear the weight of the body upon the hip joint and avoid breakage, the exterior surface 716 of the liner 715 should be flush with the interior cavity 727 surface of the shell 720 when positioned therein. The liner 715 may be formed as a coating in the interior shell 720, or may be formed as a separate component that may be press fit, snap fit, cemented, or otherwise received and held within the interior recess of the shell. The liner 715 should be made of a material that provides desired wear characteristics when articulating against the material that forms the femoral head 705, and is preferably constructed of a PEEK material. The interior cavity 717 of the liner 715 should be polished to form a smooth concave articulation surface complementary to the femoral head. If the acetabular shell 720 is formed of PEEK, the liner 715 may be eliminated and the shell cavity 727 sized and configured to directly receive the femoral head 705.

The femoral head 705 is formed as a spherical or partially spherical member for smooth rotation and pivoting within the acetabular shell 720 and/or liner 715, and is preferably made of PEEK material. The head is connected to a stem portion by a neck 704. The neck portion 704 may be inserted into a blind bore in the head 705 so that the head is seated freely on the neck 704. The head 705 in this situation may rotate and glide on the neck portion 704. Alternatively, the neck portion 704 may be attached to the head 705, for instance by press fitting the neck into a bore of the head. Other means of securing the head 705 to the neck 704 may also be used. As another alternative, the neck 704 and head 705 may be formed integrally as a single component.

The neck portion 704 connects the head 705 to a stem body 703, which supports and positions the femoral head. The stem body 703 is attached to the proximal end of the femur, and is equipped with an elongate anchor portion 702 that extends lengthwise into the femur to secure the stem body thereto. The anchor portion may be press fit into the femur or fixed therein with a cement composition. Other means for fixing the stem to the bone of the femur may also be used, either alone or in combination with the aforementioned means, such as osteoconductive porous coatings of hydroxyapatite (HA), tricalciumphosphate (TCP), and other chemical agents that promote bone growth and/or provide porous surfaces that allow bone ingrowth and osteointegration; various biological agents; and combinations thereof.

The liner 715 may be of a PEEK material and the shell of either a PEEK material or of a biocompatible metal as described previously. A metallic acetabular shell 720 may be alternatively coated or completely encased in a PEEK material with an osteoconductive surface facing the bone. The acetabular shell and the liner may also be integrated into a single component and formed of PEEK material. Likewise the stem 701 and the femoral head 705 may be integrated into a single component formed of PEEK. Alternatively, the stem 701, neck 704, and anchor 702 may remain as one or more separate components but made of metal or PEEK material and configured for attachment with a PEEK femoral head component 705. As a further alternative, a PEEK femoral head 705 may be utilized in combination with a biocompatible metallic stem 701 and neck 704 component. Alternatively, the stem 701 and/or neck 704 may be a PEEK coated component on only the articulating surfaces or the articulating and bone facing surfaces with the bone facing surfaces having an osteoconductive surface such as a hydroxyapatite coating. As a further alternative, the femoral head 705 may be a biocompatible metallic component with a smooth PEEK coating or layer smoothly articulating with the neck and the acetabular implant.

In all cases, the articulating joint surfaces are a combination of a PEEK material articulating on another PEEK material. Although it is preferred that these plastic components are substantially comprised of PEEK, it is contemplated that any number of plastics from the family of ether ketones may be utilized such as PEK in any variety of articular surface combinations.

Boney integration of these implants may benefit from prepared osteoconductive surfaces or coatings described elsewhere herein.

When implanted, the stem 701 is disposed at the proximal end of the femur and holds the femoral head at an angle for receipt in the liner 715 (if any) and acetabular shell 720, which is secured to the pelvic bone. The weight of the body will be borne in the joint at the interface between the upper surface 706 of the femoral head 705 and the upper surface 728 of the cavity 727 in the acetabular shell 720, shown in FIGS. 29 and 30. In the embodiment shown in FIG. 29, the femoral head 705 and liner 715 are comprised of PEEK material for articulation against one another. The femoral head is mounted to a neck portion 704 of a stem body which fits into a blind bore 750 in the femoral head. In the device shown, the acetabular shell 720 is mounted to the pelvic bone 780 using bone screws 765 that are threaded into the bone through openings 724 in the acetabular shell 720. The bone screws, as well as the acetabular shell, may be comprised of PEEK material or a biocompatible metal. The PEEK material liner is held within an outer acetabular shell by detents that allow the liner to snap lock into the shell. As previously mentioned, however, other methods may be used to secure the acetabular shell to the pelvic bone, and to secure the liner to the acetabular shell. The PEEK material liner covers the heads of the bone screws and the openings in the acetabular shell, providing a smooth concave articulation surface within the cavity of the acetabular shell, and also preventing the bone screws from reverse threading.

Figure 33:
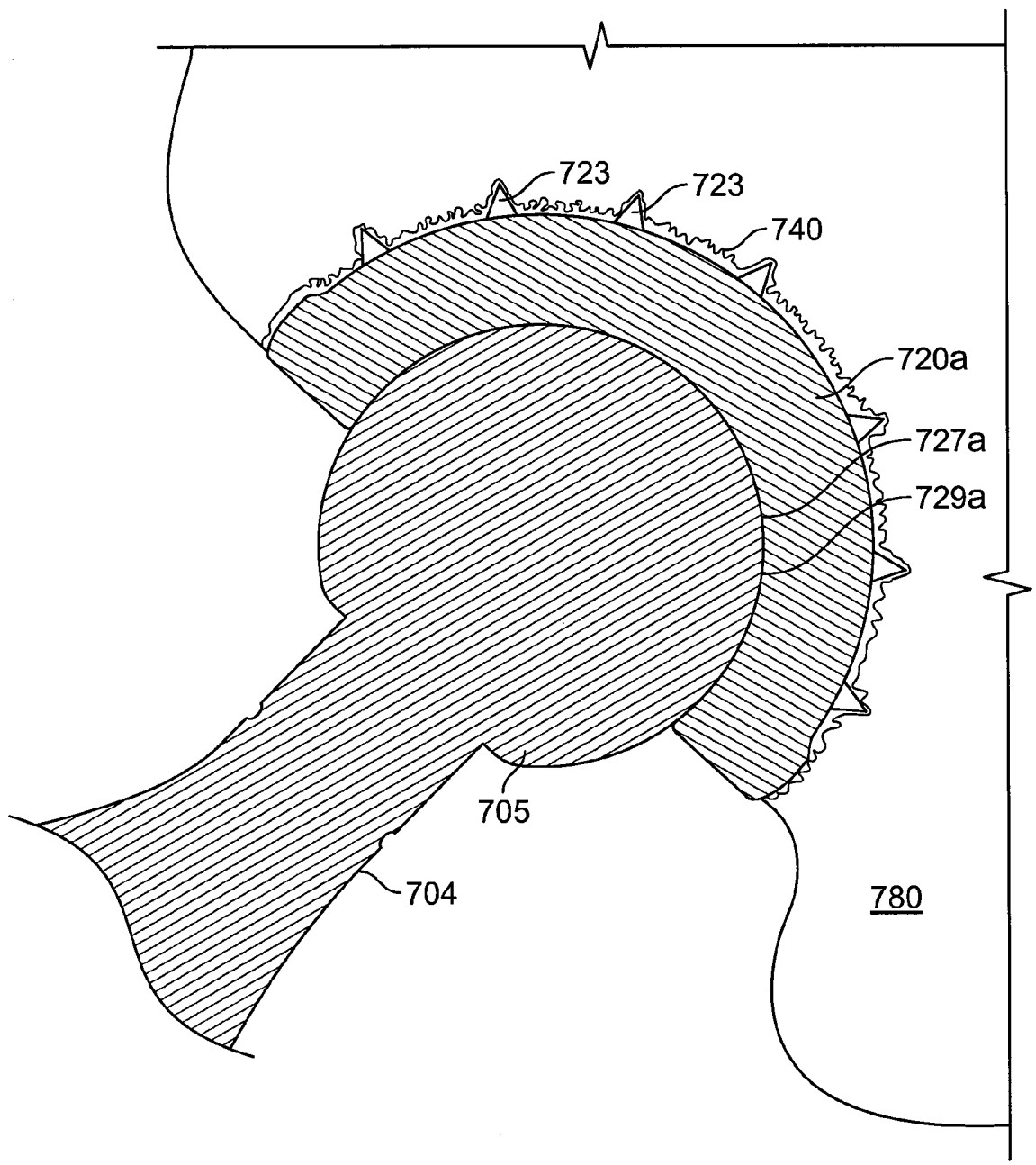
FIG. 33 is a cross sectional view of another form of hip prosthesis.

In another form, as shown in FIG. 33, the femoral head 705 and stem 701, including the neck 704 and stem body, are comprised of PEEK material, with the head 705 configured for articulation within a one-piece acetabular shell 720a also comprised of PEEK material. In the implant illustrated in FIG. 33, the acetabular shell 720a is secured to the pelvic bone 780 with a series of spikes 723 formed on the outer surface, and a porous coating 740 comprised of an osteoconductive material such as hydroxyapatite or tricalcium phosphate. By forming the acetabular shell 720a of PEEK material, a separate liner is not necessary (although one may be used if desired), and therefore the inner surface 729a of the cavity 727a in the acetabular shell 720a contains a concave spherical surface sized to receive the femoral head directly.

Figure 34:
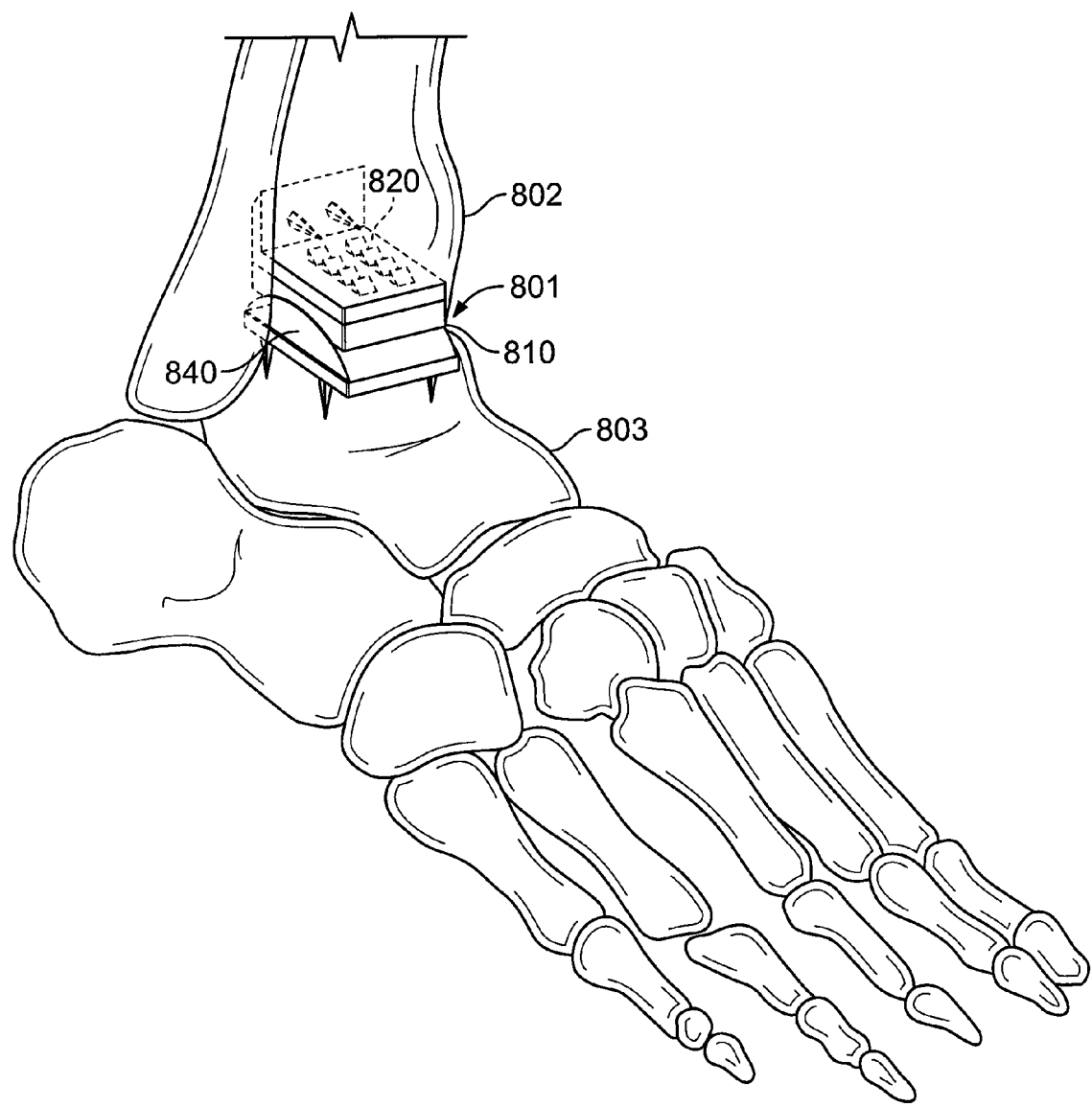
FIG. 34 shows an ankle joint with an artificial ankle prosthesis.

FIGS. 34-37 illustrate other improved arthroplasty devices in the form of ankle implants 801. As best shown in FIG. 34, the illustrated devices are designed for insertion into the tibiotalar joint, between the distal end of the tibia 802 and the superior surface of the talus 803, although other positioning is possible in order to maintain some degree of movement of the ankle. An articulation joint 810 is provided between upper 820 and lower 840 members of the device. The joint comprises at least one cylindrical, spherical, or other curved surface for articulating against another surface. In the illustrated embodiments of FIGS. 34-37, the upper member 820 contains an inferior surface 822 having a concave configuration, while the lower member 840 contains an upper convex surface 842 for articulation against the concave surface 822 of the upper member 820. Of course, the implant may be configured so that the lower member 840 contains a concave surface and the upper member 820 contains a convex surface. If desired, the curvature and profiles of the convex/concave surfaces may be selected to allow more movement in a first direction than in a second direction in order to more closely mimic the natural movement of the ankle joint.

The distal end of the tibia 802 and the superior surface of the talus 803 may be shaved or cut away in order to provide complementary surfaces for mounting the upper articulating member 820 and lower articulating member 840, respectively, as shown in FIG. 34. Spikes or other anchor elements may be provided to fix the articulating members to the bone. The spikes or other anchor elements may be formed of PEEK material as integral parts of the implant, may be made of a PEEK material or biocompatible metal attached to the implant, or may be made of a biocompatible metal molded into the body of the PEEK material implant.

Figure 35:
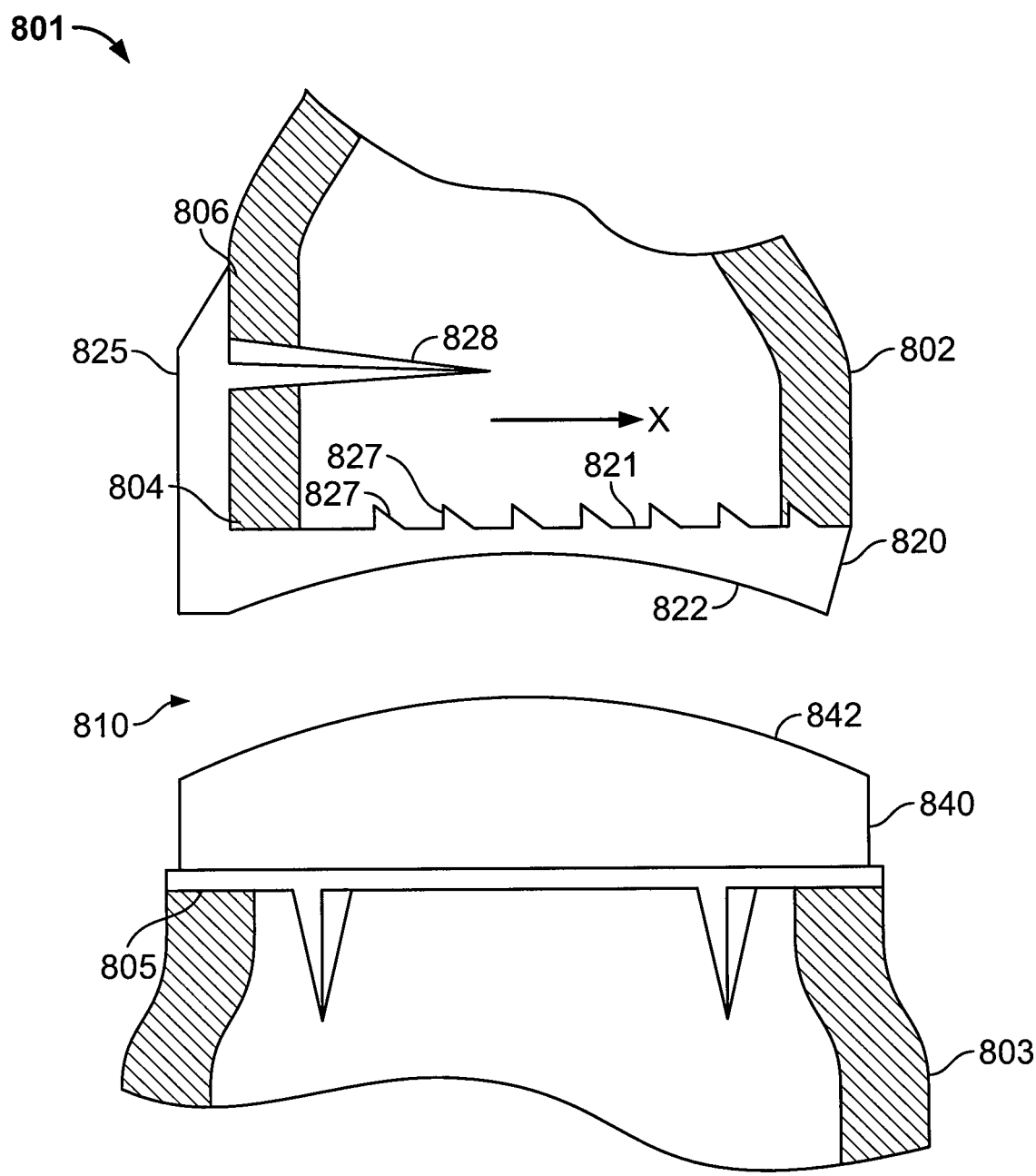
FIG. 35 is a cross sectional view of the ankle prosthesis in FIG. 34.
Figure 36:
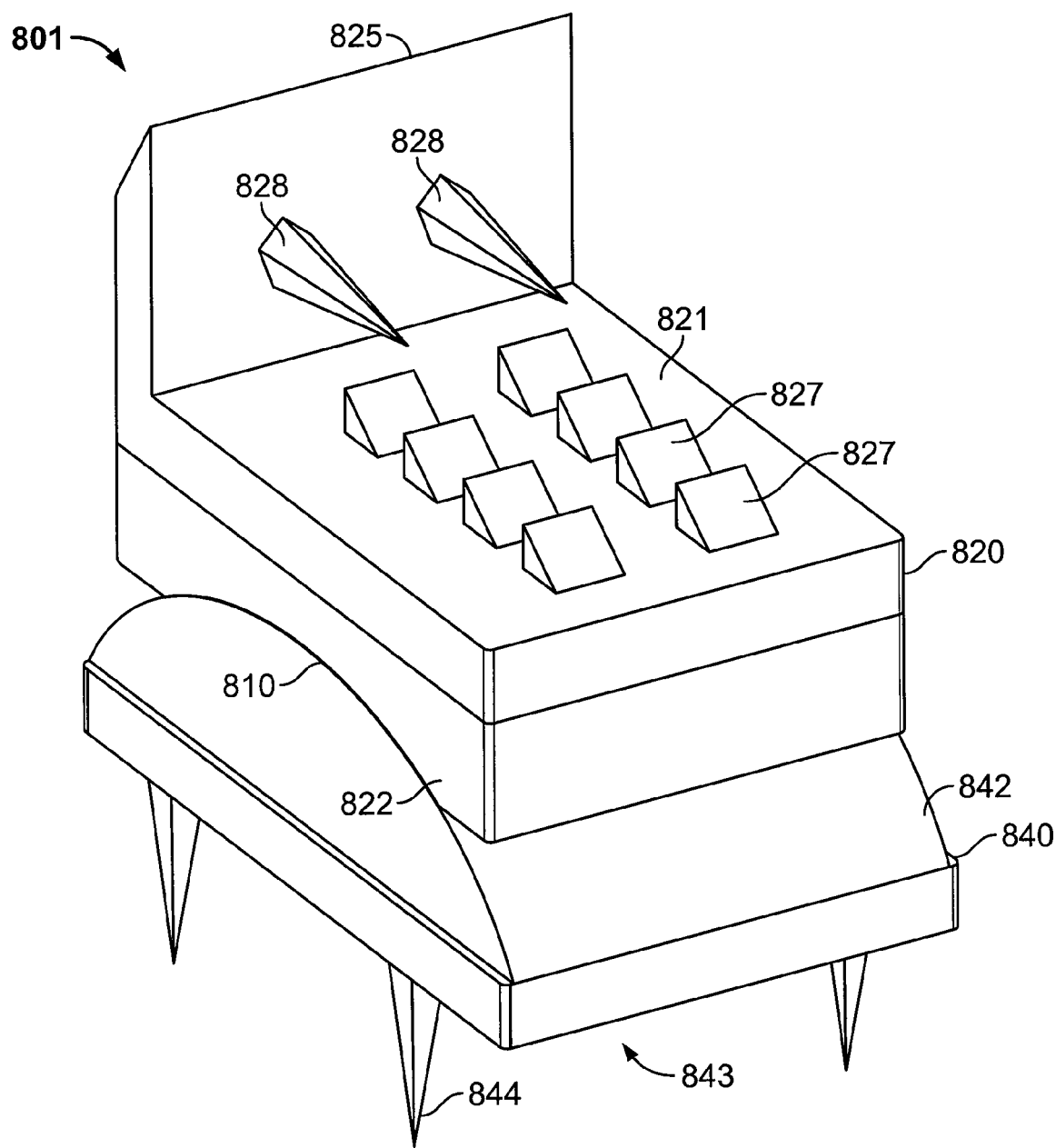
FIG. 36 is a perspective view of an ankle prosthesis.

For instance, the upper articulation member 820 may contain teeth 827 and/or spikes 828 on its superior surface 821 for fixation to the tibia 802, as shown in FIG. 35. In one form, a series of inclined teeth 827 may be provided to prevent movement of the upper member 820 along the plane of the tibial end surface 804. The upper member 820 may also be provided with one or more fixation elements such as spikes 828 that are essentially parallel, or at least non-orthogonal, to the superior surface 821 in order to prevent vertical movement of the upper member 820 away from the tibia 802. In the illustrated implant of FIG. 35, the teeth 827 on the superior engagement surface 821 of the upper member 820 are angled such that they may move with relative ease in a direction X during implantation, but will resist backward movement. In addition, the upper member 820 contains a rear plate 825 having one or more spike-like projections 828 thereon. The rear plate 825 provides a hard stop that limits movement during implantation in a direction X. The combination of teeth 827 and rear plate 825 therefore cooperate to fully prevent movement along the plane of the tibial end 804 after implantation, since the teeth 827 prevent movement away from direction X, while the rear plate 825 prevents further movement in direction X by abutting a side surface 806 of the tibia 802. Lateral movement, as well as movement orthogonal to the plane of the tibial end, is prevented by the spike-like protrusion 828 extending through the side surface 806 of the bone. Such a configuration advantageously allows the entire upper articulation member 820 with associated fixation elements to be manufactured as a unitary body from a single piece of a PEEK-type material.

Figure 37:
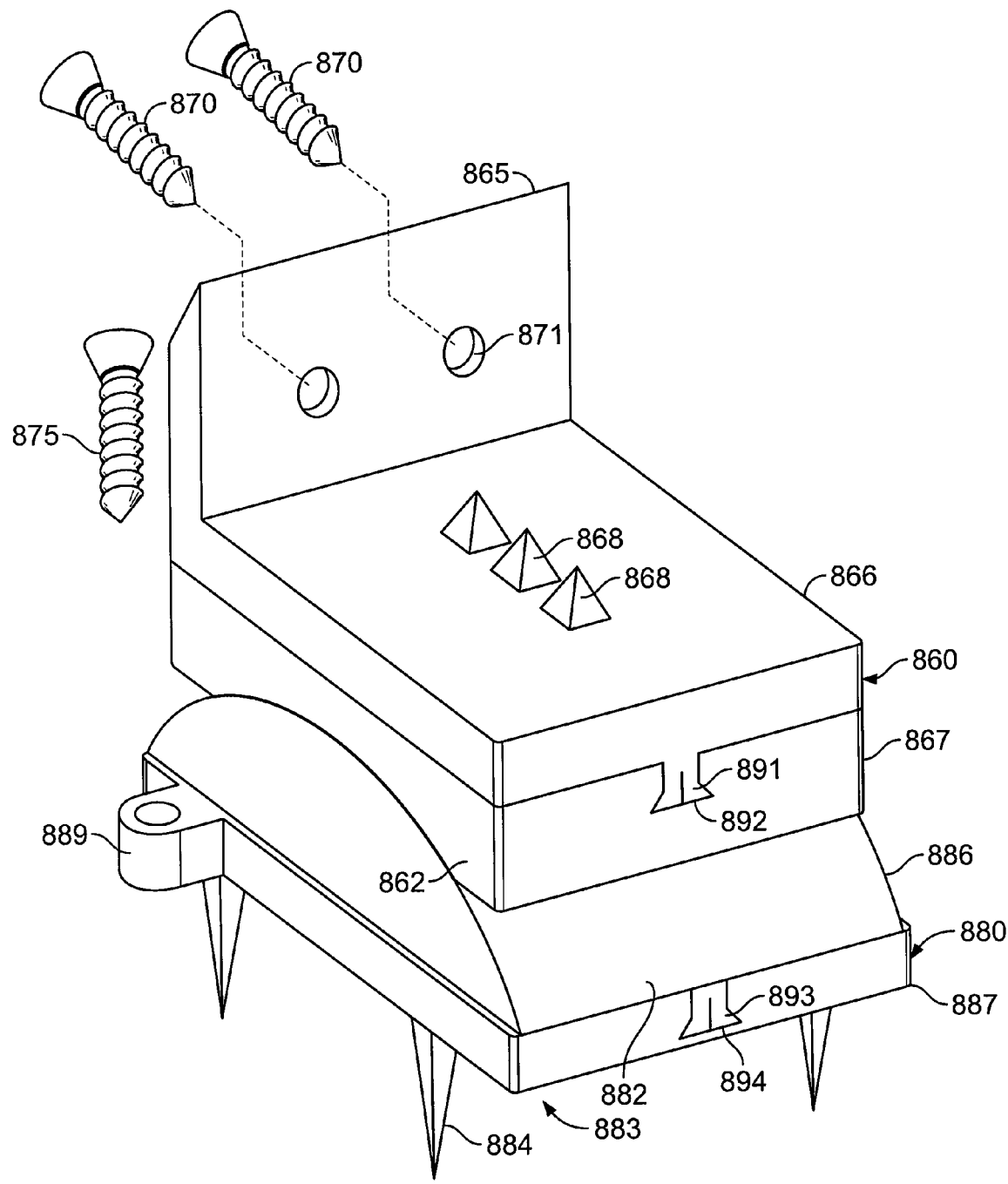
FIG. 37 is a perspective view of another type of ankle prosthesis.

Alternatively, as shown in FIG. 37, the articulation members may be configured to receive separate fixation members 870 and 875 for securing to the bone. As shown in the illustrated embodiment, the rear plate of the upper articulation member contains openings 871 for receiving bone screws 870 that are used to secure the rear plate 865 to the tibia. The upper articulation member 860 also contains spikes 868 that further prevent movement and stabilize the upper member 860 against the tibia. To attach the upper member to the tibia, the spikes 868 are first driven axially upward into the lower surface of the tibia, and then bone screws 870 are inserted through the holes 871 in the rear plate 865 and into bone. Bone screws 875 may also be provided to secure the lower articulation member 880, such as the screws inserted through collars 889 formed on lateral surfaces of the lower member 880.

Referring back to FIG. 36, the lower articulation member 840 has a superior articulation surface 842 complementary to the inferior articulation surface 822 of the upper member 820, and forming a convex cylindrical surface. A spherical or otherwise curved surface may alternatively be provided. The opposite inferior surface 843 of the lower articulation member 840 forms an engagement surface that may be provided with fixation elements 844 in order to secure the lower member 840 to the upper surface of the talus. These fixation elements may be provided in the form of spikes or other protrusions that may be driven downward into the surface of the talus, although other fixation elements are also contemplated, such as teeth; threads; elongate keels; screwlike projections; means for receiving fixation devices, such as throughbores for receiving screws or pins; and the like. Other means for fixing the lower member to the bone of the talus may also be used, such as osteoconductive porous coatings of hydroxyapatite (HA), tricalciumphosphate (TCP), and other chemical agents that promote bone growth and/or provide porous surfaces that allow bone ingrowth and osteointegration; cements; adhesives; various biological agents; and combinations thereof.

The articulation surfaces 822 and 842 of the upper and lower members should be polished in order to provide smooth gliding movement against one another with minimal particulate formation due to wear. Both articulation surfaces may be made of PEEK-type material. Each of the articulation members may be made entirely of PEEK-type materials to form two unitary articulation bodies, but one or both members may also be formed in part of a biocompatible metal coated or encased at least partially in a PEEK material, or may be formed as a baseplate for securing to the tibia or talus with a surface configured to receive a PEEK articulation surface in the form of a liner. For instance, as shown in FIG. 37, the upper articulation member 860 may be comprised of an upper mounting plate 866 formed of metal or PEEK material and removeably secured to a first PEEK articulation portion 867 by corresponding flanges 891 and slots 892 or other known connection means. Likewise, the lower articulation member 880 may comprise a lower mounting plate 887 made of metal or PEEK material and removeably secured to a second PEEK articulation portion 886 by corresponding flanges 893 and slots 894 or other known connection means.

Figure 38:
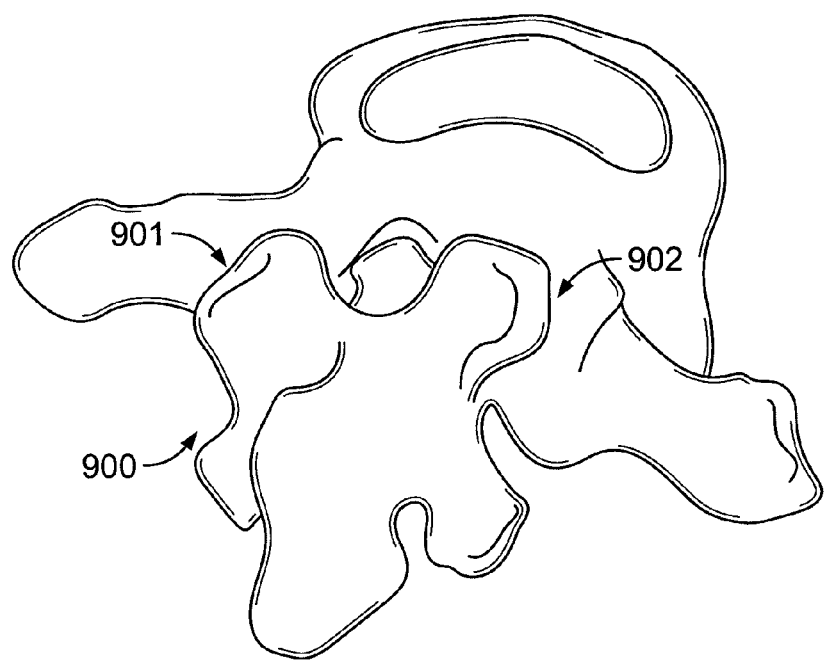
FIG. 38 is a perspective view of a vertebra displaying the facet joints thereof.
Figure 39:
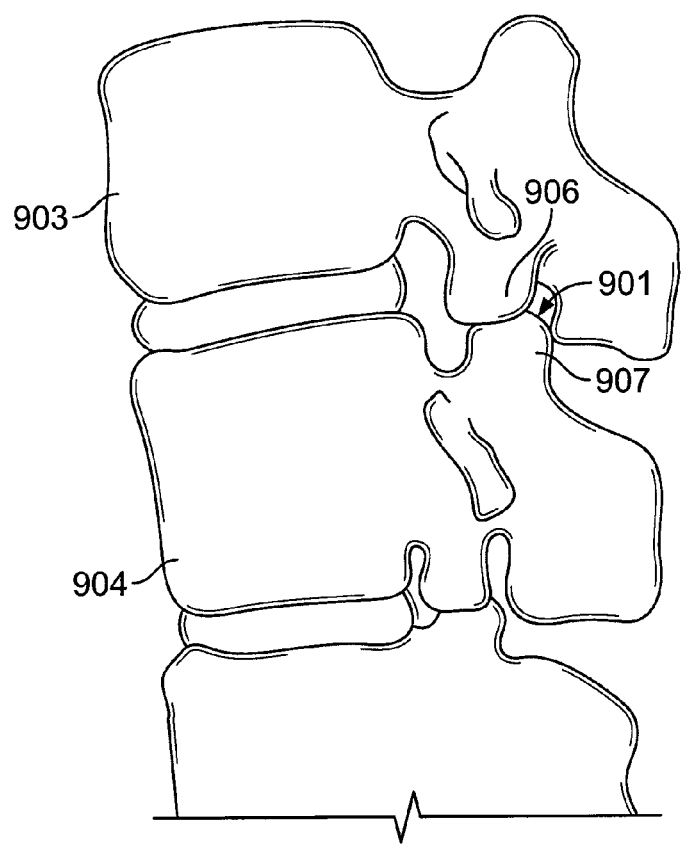
FIG. 39 is a side view of a portion of the vertebral column.
Figure 40:
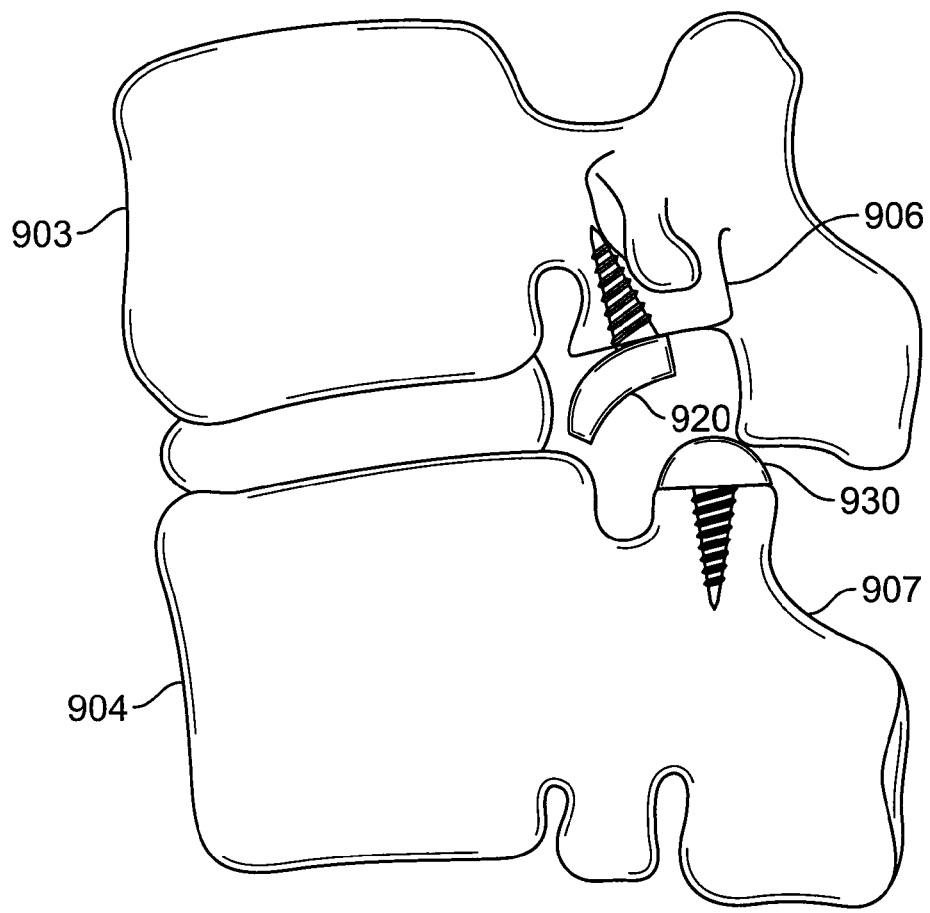
FIG. 40 is a side view of a portion of the vertebral column fitted with an artificial facet prosthesis.

In another form, an artificial facet joint is formed from two PEEK material implants. The natural facet joints 901 and 902 of the spinal column, shown in FIGS. 38 and 39, are synovial joints on the posterior or dorsal side of the spinal column 900 where an inferior bony protrusion 906, or facet, of one vertebra 903 moves against a superior bony protrusion 907 of an adjacent vertebra 904. When these facets must be replaced due to breakage or disease, it is preferred that the implant replacement mimic the natural articulation of the facet joint as closely as possible in order to permit flexion, extension, and rotation of the spine. In one aspect, and as illustrated in FIG. 40 articulating members 920 and 930 are mounted to the spine in order to replace cut away portions of the superior articular facet 907 of one vertebra and the inferior articular facet 906 of an adjacent, rostral vertebra 903. The articulating members 920 and 930 are configured for sliding past one another during flexion and extension of the spine. For instance, the articulating members may form one convex articulation surface 921 and one concave articulation surface 931, such as the trough-like formation of the inferior facet member 920 and the spherical surface 931 of the superior facet member 930 shown in FIGS. 40 and 41. Alternatively, the implants may form other shapes, such as fins approximating the natural vertebral facets. If large sections of the vertebra must be removed, larger plates may be used to replace extensive portions of the spinous process, transverse process and facets in order to protect the spinal column.

Figure 41:
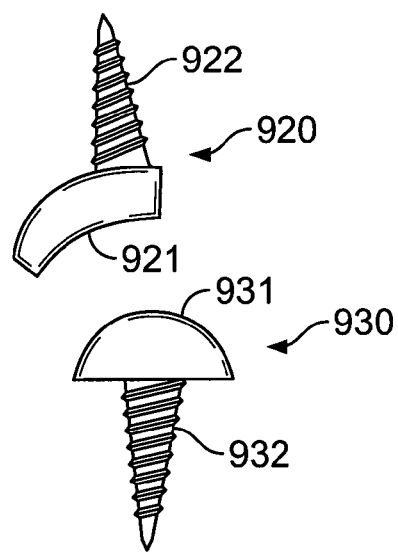
FIG. 41 is a view of two components of an artificial facet prosthesis.

The trough-like inferior member 920 is implanted in the lower side of the spinal process of a rostral vertebra 903, while the spherical superior member 930 is implanted in the upper side of a caudal vertebra 904, as shown in FIG. 41. As illustrated, the articulation surfaces are formed of PEEK material, each with a respective anchor member in the form of a screw shank 922 and 932 formed integrally therewith to anchor the articulation member to the spine. The anchor members may alternatively comprise spikes or other known means for securing a member to bone, with or without cements, adhesives, or biological agents. The anchor members may have osteoconductive porous coatings of hydroxyapatite (HA), tricalciumphosphate (TCP), and other chemical agents that promote bone growth and/or provide porous surfaces that allow bone ingrowth and osteointegration may also be used to assist in fixing the members to the spine. Also, the anchor members 922 and 932 may form separate components made of metal or PEEK materials to mount the PEEK articulation members 920 and 930 to the bone.

Figure 42:
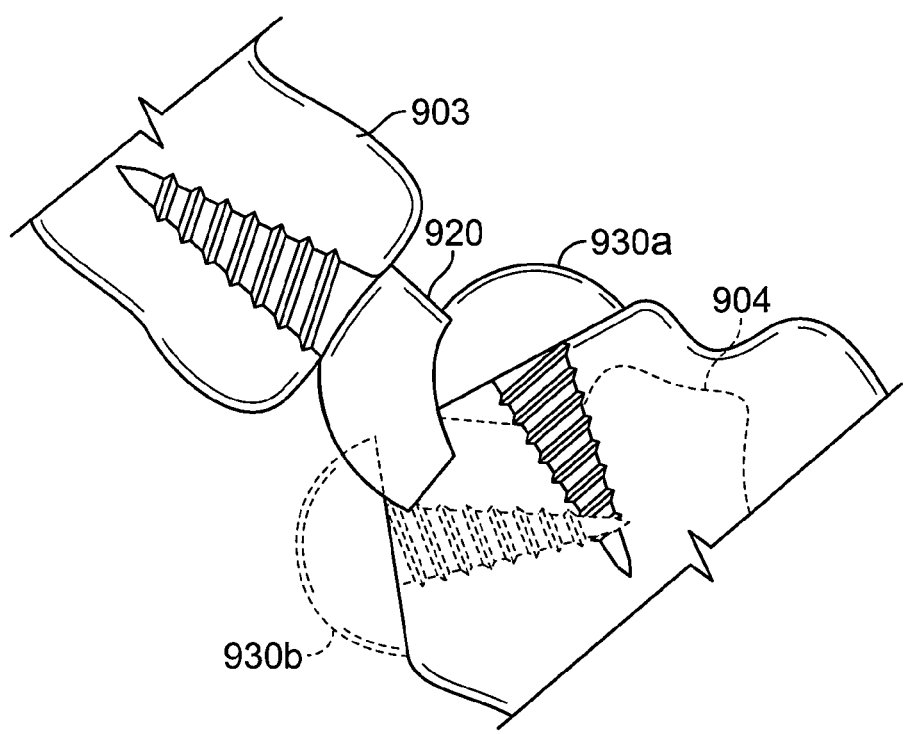
FIG. 42 illustrates articulation of an artificial facet prosthesis.

The convex 931 and concave 921 surfaces are able to slide past one another during flexion and extension of the spine. As shown in FIG. 42, as the caudal vertebra 904 moves with respect to the rostral vertebra 903 during extension, the superior articulation member 930 slides from a first position 930a to a second position 930b along the inferior articulation member 920.

Other forms of an artificial fact joint comprising PEEK articulation surfaces are also possible in accordance with the teachings herein.

Figure 43:
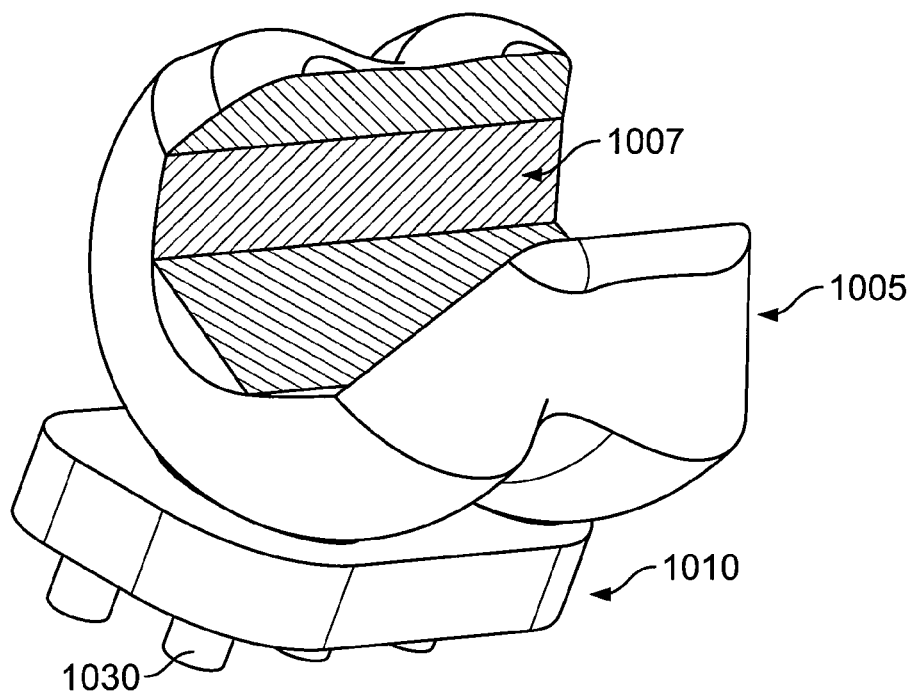
FIG. 43 is a perspective view of another alternative knee joint with a one-piece femoral cap and one-piece tibial plate.
Figure 44:
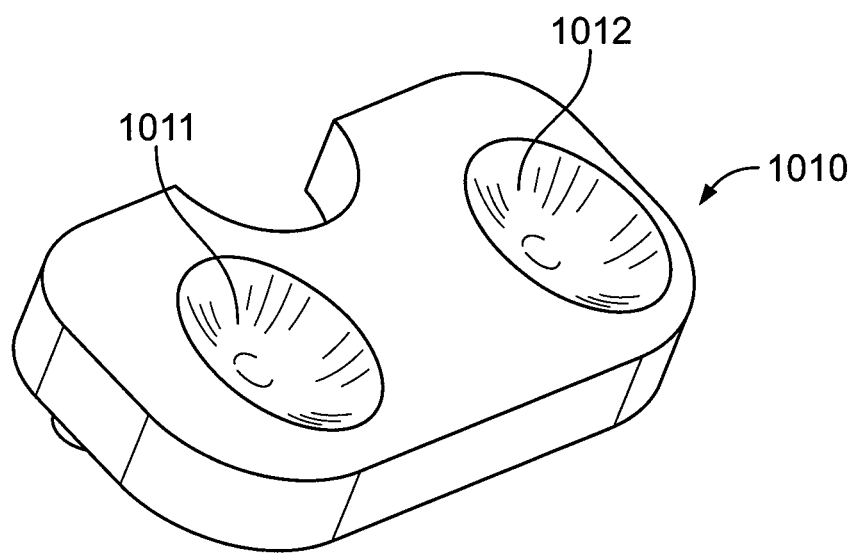
FIG. 44 is a perspective view of the tibial plate from the embodiment shown in FIG. 43
Figure 45:
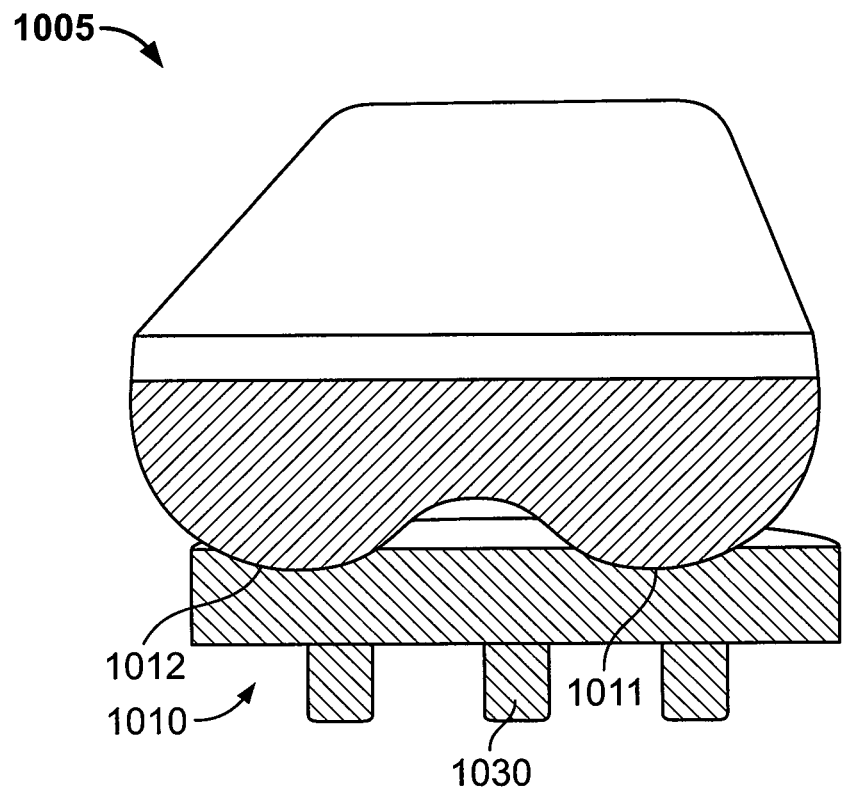
FIG. 45 is a cross sectional view of the knee joint in FIG. 43 displaying the articulating interface of the two prosthesis portions.

Another alternative knee prosthesis is shown in FIGS. 43-45. The function and structure, including materials, are generally similar to that described in 28-30. As shown in FIG. 43, the femoral cap 1005 is attached at an attachment surface 1007 to the femur and operates to articulate against tibial tray 1010, which is secured to the tibia by anchor elements. The femoral cap 1007 and tibial tray 1010 may be formed entirely of PEEK materials, or may contain a PEEK coating at the articulation surfaces. The anchor elements 1030 may be formed of PEEK, or may alternatively comprise a biocompatible metal molded into the tibial tray portion 1010. As shown in FIGS. 44 and 45, the tibial tray 1010 contains two articulating recesses 1011 and 1012 which are configured to receive the femoral cap 1005 for articulation therein.

Figure 46:
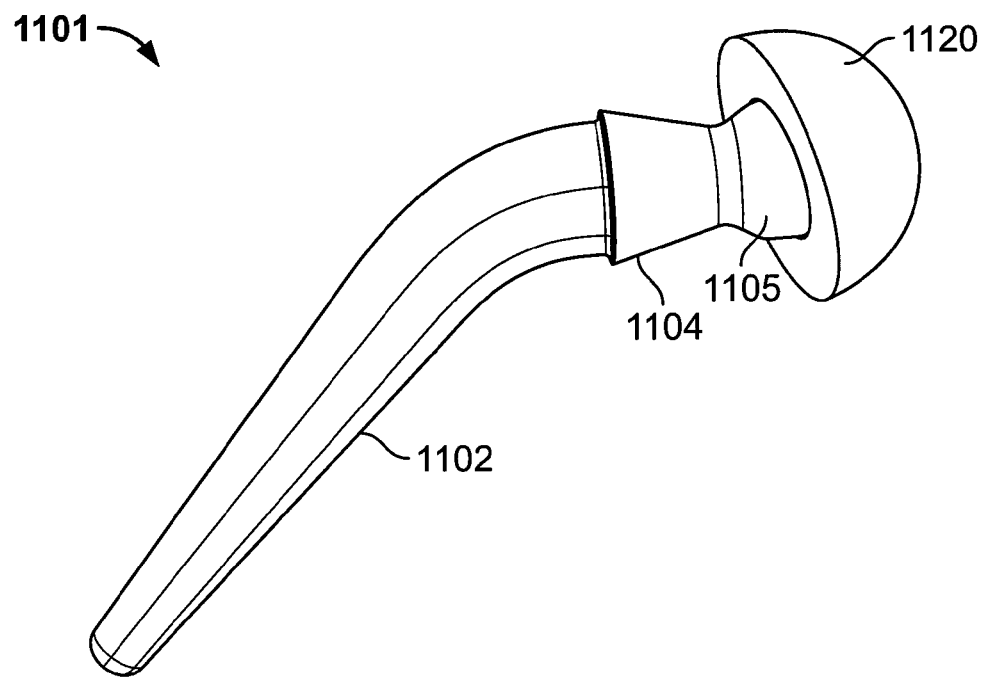
FIG. 46 is another alternative hip replacement device comprising a one-piece acetabular cup.
Figure 47:
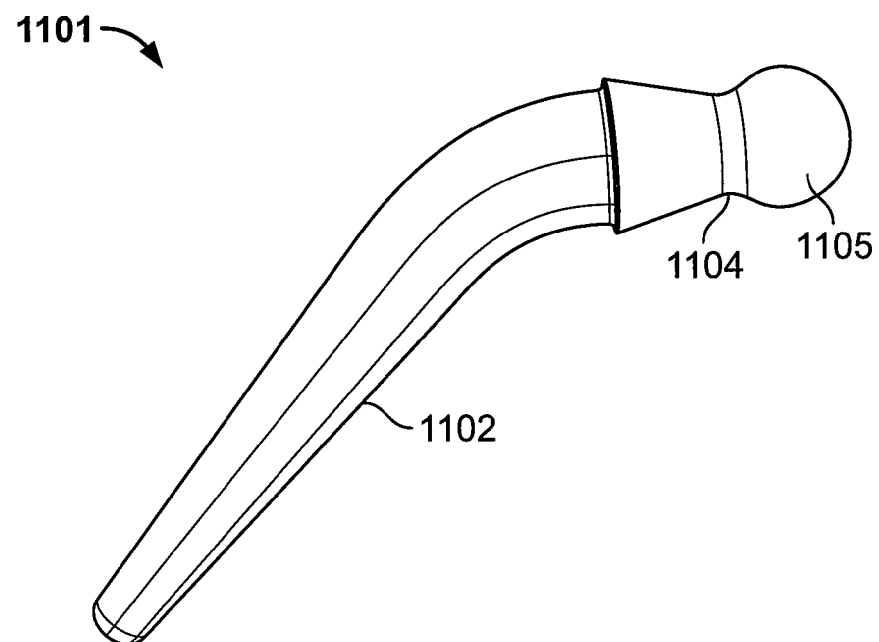
FIG. 47 is a view of the stem and head portions of the hip replacement device in FIG. 46 without the acetabular cup.

Another alternative hip replacement device is shown in FIG. 46, comprising an elongate anchor portion 1102 for anchoring the device into the femur and a head portion 1105 configured for articulation in an acetabular cup 1120. Since the acetabular cup 1120 is made of PEEK material, no liner is needed. The head 1105 is made of PEEK material and connected to the stem 1101 by a neck portion 1104. The stem 1101 and head 1105 portions are shown in FIG. 47 without the acetabular cup. The device operates in the manner described above as to FIGS. 31 and 33, and may be made with a number of variations as described.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A two-piece intervertebral prosthesis comprising: a first weight bearing member being a first one of the two-pieces of the intervertebral prosthesis and having a unitary one-piece construction including a first prosthetic endplate having a first outer surface thereof adapted to engage a first vertebral body and a first interior bearing surface, and a second weight bearing member being a second one of the two-pieces of the intervertebral prosthesis and having a unitary one-piece construction including a second prosthetic endplate having a second outer surface thereof adapted to engage a second vertebral body and a second interior bearing surface, the first and second prosthetic endplates being adapted to maintain proper spacing between the first and second vertebral bodies, and the first and second interior bearing surfaces being configured to cooperatively engage each other to allow for physiological kinematics and loadings of the first and second vertebral bodies, wherein the first interior bearing surface comprises a recessed bearing portion having a substantially concave bearing surface and the second interior bearing surface comprises a dome bearing portion having a substantially convex bearing surface, and the recessed portion including the substantially concave bearing surface and the dome portion including the substantially convex bearing surface being of a PEEK type material and configured to cooperatively engage each other to provide a low friction, low wear and substantially non-deforming interface under physiological kinematics and loadings, the dome bearing portion of the second weight bearing member having an undercut recess therein so that there is an opening that is recessed in the dome bearing portion with a flat surface of the second end plate of the second weight bearing member extending into the undercut recess for receipt of a portion of an insertion tool therein, the opening having a narrow width with opposite ends adjacent to the second end plate flat surface so the narrow width opening extends along and adjacent to the second end plate flat surface and into the dome bearing portion with the dome bearing portion directly overlying the undercut recess therein, the dome bearing portion having an internal end surface portion of the undercut recess and an internal upper surface portion of the undercut recess that is spaced from the second end plate flat surface and interconnected thereto by the internal end surface portion.

2. The joint prosthesis of claim 1, wherein the first and second interior bearing surfaces are of substantially non-conforming shapes.

3. The intervertebral prosthesis of claim 1, wherein the first and second interior bearing surfaces allow for at least one degree of substantially translational motion of the first and second members.

4. The intervertebral prosthesis of claim 1, wherein the first and second interior bearing surfaces are substantially smooth for improved wear performance.

5. The intervertebral prosthesis of claim 4, wherein the first and second interior bearing surfaces have an average surface roughness of no more than 60 micro inches.

6. The intervertebral prosthesis of claim 1, wherein the first interior bearing surface and second interior bearing surfaces are each of PEEK and form a PEEK-on-PEEK bearing interface.

7. The intervertebral prosthesis of claim 1, wherein the first and second prosthetic endplates are entirely of a PEEK type material less any radiographic markers.

8. The intervertebral prosthesis of claim 1, wherein the first and second prosthetic endplates cooperate to form a prosthetic total disc device for replacing the annulus and nucleus of a spinal disc.

9. The intervertebral prosthesis of claim 8, wherein the first outer surface of the first prosthetic endplate and the second outer surface of the second prosthetic endplate include outer surface features for securing the prosthetic endplates to the adjacent vertebral bodies.

10. The intervertebral prosthesis of claim 9, wherein the outer surface features are adapted to secure the prosthetic endplates to the vertebral endplates of the adjacent vertebral bodies.

11. The intervertebral prosthesis of claim 10, wherein the first outer surface of the first prosthetic endplate and the second outer surface of the second prosthetic endplate are shaped to substantially match the surface profile of the natural vertebral endplate of the adjacent vertebral bodies.

12. The intervertebral prosthesis of claim 9, wherein the outer surface features are adapted to secure the prosthetic endplates to the adjacent vertebral bodies after removal of the vertebral endplates.

13. The intervertebral prosthesis of claim 1, wherein the first and second prosthetic endplates cooperate to form a prosthetic nucleus device for replacing a nucleus of a spinal disc and are sized to fit within and be retained by a natural annulus of the disc.

14. The intervertebral prosthesis of claim 13, wherein the first outer surface of the first prosthetic endplate and the second outer surface of the second prosthetic endplate are adapted to articulate against the adjacent vertebral bodies.

15. The intervertebral prosthesis of claim 13, wherein the first outer surface of the first prosthetic endplate and the second outer surface of the second prosthetic endplate are of a PEEK type material and comprise a substantially smooth outer surface finish to provide a low friction and low wear bearing interface at the adjacent vertebral bodies.

16. The intervertebral prosthesis of claim 1 wherein the dome bearing portion is truncated so that the convex bearing surface intersects with a flat surface extending transversely to the convex bearing surface and meeting the internal upper surface portion at the narrow width opening to the undercut recess.

17. A motion preservation implant sized for insertion into an intervertebral space, the implant comprising:

a pair of polymeric articulating members with each of the polymeric articulating members having a unitary one-piece construction;

polymeric bodies of the articulating members that are of identical polymeric material; and polymeric inner bearing surfaces of the polymeric articulating members that are of the identical polymeric material and are configured to allow for relative motion between the articulating members, the polymeric articulating members providing optimized wear resistance and avoiding strength loss due to strain hardening at the polymeric bearing surfaces thereof, wherein the polymeric inner bearing surfaces include a dome bearing portion having a convex bearing surface of one of the articulating members and a recessed bearing portion having a concave bearing surface of the other articulating member, the dome bearing portion being truncated so that the convex bearing surface intersects with a flat surface extending transversely thereto, and the dome bearing portion having an undercut recess therein so that there is an opening at the flat surface and that is recessed in the dome bearing portion for receipt a portion of an insertion tool therein with the dome bearing portion directly overlying the undercut recess therein and having facing upper and lower internal surface portions in the undercut recess that are rigidly fixed relative to each other.

18. The implant of claim 17 wherein the other articulating member includes an arcuate, thin wall portion at the concave surface thereof.

19. The implant of claim 17 wherein the articulating members have a predetermined wear rate that is approximately an order of magnitude lower than conventional UHMWPE on metal bearing couples when simulator tested with loading and kinematic profiles that are frequency shifted.

20. The implant of claim 17 wherein the polymeric material is a pure PEEK material that after manufacture does not require further processing for strength enhancement thereof.

21. The implant of claim 17 wherein the polymeric articulating members include narrow and high strength predetermined portions thereof that are of the polymeric material and configured for being engaged by an insertion tool to advance the members into the intervertebral space.

22. The implant of claim 21 wherein one of the predetermined portions includes a post for being gripped by a metallic arm of the insertion tool.

23. The implant of claim 21 wherein one of the predetermined portions includes arcuate surface portions generally adjacent a trailing end of one of the polymeric articulating members for being engaged by a metallic tip of the insertion tool.

24. The implant of claim 17 wherein the polymeric articulating members include polymeric outer bearing surfaces of the polymeric material configured for non-invasively bearing against respective adjacent vertebral bodies.

25. The implant of claim 17 wherein the polymeric material is PEEK so that the polymeric inner bearing surfaces are PEEK-on-PEEK inner bearing surfaces and wherein the articulating members have a predetermined wear rate comparable to wear resistant metallic bearing couples when simulator tested with loading and kinematic profiles that are frequency shifted.

* * * * *